(12) United States Patent
Blagg et al.

(10) Patent No.: US 12,030,867 B2
(45) Date of Patent: Jul. 9, 2024

(54) Hsp90β SELECTIVE INHIBITORS

(71) Applicants: University of Notre Dame du Lac, South Bend, IN (US); University of Kansas, Lawrence, KS (US)

(72) Inventors: Brian Blagg, Notre Dame, IN (US); Sanket Mishra, Notre Dame, IN (US)

(73) Assignees: University of Notre Dame du Lac, South Bend, IN (US); University of Kansas, Lawrence, KS (US)

( * ) Notice: Subject to any disclaimer, the term of this patent is extended or adjusted under 35 U.S.C. 154(b) by 744 days.

(21) Appl. No.: 17/055,980

(22) PCT Filed: May 30, 2019

(86) PCT No.: PCT/US2019/034672
§ 371 (c)(1),
(2) Date: Nov. 16, 2020

(87) PCT Pub. No.: WO2019/232223
PCT Pub. Date: Dec. 5, 2019

(65) Prior Publication Data
US 2021/0269418 A1 Sep. 2, 2021

Related U.S. Application Data

(60) Provisional application No. 62/730,402, filed on Sep. 12, 2018, provisional application No. 62/677,873, filed on May 30, 2018.

(51) Int. Cl.
| | | |
|---|---|---|
| C07D 401/14 | (2006.01) | |
| A61P 35/00 | (2006.01) | |
| C07D 401/04 | (2006.01) | |

(52) U.S. Cl.
CPC ............ C07D 401/14 (2013.01); A61P 35/00 (2018.01); C07D 401/04 (2013.01)

(58) Field of Classification Search
CPC .................................................. C07D 401/14
See application file for complete search history.

(56) References Cited

U.S. PATENT DOCUMENTS

| | | |
|---|---|---|
| 3,594,380 A | 7/1971 | Sulkowski |
| 7,208,630 B2 | 4/2007 | Blagg et al. |
| 7,608,594 B2 | 10/2009 | Blagg et al. |
| 8,143,274 B2 | 3/2012 | Hattori et al. |
| 8,569,323 B2 | 10/2013 | Ren et al. |
| 8,809,349 B2 | 8/2014 | Ren et al. |
| 9,457,045 B2 | 10/2016 | Gleave et al. |
| 9,481,667 B2 | 11/2016 | Genov et al. |
| 2008/0070935 A1 | 3/2008 | Huang et al. |
| 2012/0157454 A1 | 6/2012 | Papeo et al. |
| 2012/0252745 A1 | 10/2012 | Blagg et al. |
| 2019/0023666 A1 | 1/2019 | Pham et al. |

FOREIGN PATENT DOCUMENTS

WO    WO 2016/161145    * 10/2016

OTHER PUBLICATIONS

Bagatell et al., "Induction of a heat shock factor 1-dependent stress response alters the cytotoxic activity of hsp90-binding agents", Clinical Cancer Research : an official journal of the American Association for Cancer Research, vol. 6, 2000, pp. 3312-3318.
Barrott et al., "Hsp90, an Unlikely Ally in the War on Cancer", The FEBS Journal, vol. 280, 2013, pp. 1381-1396.
Bhat et al., Progress in the discovery and development of heat shock protein 90 (hsp90) inhibitors, J. Med. Chem., vol. 57, 2014, pp. 8718-8872.
Biamonte et al., "Heat shock protein 90: inhibitors in clinical trials", J. Med. Chem., vol. 53, 2010, pp. 3-17.
Butler et al., "Maximizing the Therapeutic Potential of HSP90 Inhibitors", Mol Cancer Res., vol. 13, 2015, pp. 1445-1451.
Chen et al., "The HSP90 family of genes in the human genome: insights into their divergence and evolution", Genomics, vol. 86, 2005, pp. 627-637.
Chiosis et al., "A Global View of Hsp90 Functions", Nature Structural & Molecular Biology, vol. 20, 2013, pp. 1-4.
Crowley et al., "Development of Glucose Regulated Protein 94-Selective Inhibitors Based on the Bnlm and Radamide Scaffold", J Med Chem., vol. 59, 2016, pp. 3471-3488.
Didelot et al., "Interaction of heat shock protein 90beta isoform (HSP90beta) with cellular inhibitor of apoptosis 1 (c-IAP1) is required for cell differentiation", Cell death and Differentiation, vol. 15, No. 5, 2008, pp. 859-866.
Duerfeldt et al., "Development of a Grp94 inhibitor", Journal of the American Chemical Society, vol. 134, 2012, pp. 9796-9804.
Garcia-Carbonero et al., "Inhibition of Hsp90 molecular chaperones: moving into the clinic", Lancet Oncology, vol. 14, 2013, pp. e358-e369.
Garg et al., "Anticancer Inhibitors of Hsp90 Function: Beyond the Usual Suspects", Adv Cancer Res, vol. 129, 2016, pp. 51-88.
Gewirth, "Paralog Specific Hsp90 Inhibitors—A Brief History and a Bright Future", Curr. Top. Med. Chem., vol. 16, 2016, pp. 2779-2791.
Hong et al., "Targeting the molecular chaperone heat shock protein 90 (HSP90): lessons learned and future directions", Cancer Treatment Reviews, vol. 39, 2013, pp. 375-387.
Jhaveri et al., "Advances in the clinical development of heat shock protein 90 (Hsp90) inhibitors in cancers", Biochim. Biophys. Acta., vol. 1823, 2012, pp. 742-755.
Jolly et al., "Role of the heat shock response and molecular chaperones in oncogenesis and cell death", J Natl Cancer Inst., vol. 92, 2000, pp. 1564-1572.
Karagoz et al., "Hsp90 interaction with clients", Trends Biochem. Sci, vol. 40, 2015, pp. 117-125.

(Continued)

*Primary Examiner* — Rei Tsang Shiao
(74) *Attorney, Agent, or Firm* — Michael Best & Friedrich LLP

(57) ABSTRACT

Described are compounds of formula (I), based on an isoquinolin-1(2H)-one backbone, that function as Hsp90β selective inhibitors. Also described are pharmaceutical compositions thereof and methods of treating cancer by administering compounds of formula (I).

29 Claims, 12 Drawing Sheets

(56) References Cited

OTHER PUBLICATIONS

Khandelwal et al., "Natural Product Inspired N-Terminal Hsp90 Inhibitors: From Bench to Bedside?", Medicinal Research Reviews, vol. 36, 2016, pp. 92-118.
Kim et al., "Development of a fluorescence polarization assay for the molecular chaperone Hsp90", Journal of Biomolecular Screening, vol. 9, 2004, pp. 375-381.
Lee et al., "Development of a mitochondria-targeted Hsp90 inhibitor based on the crystal structures of human TRAP1", J. Am. Chem. Soc., vol. 137, 2015, pp. 4358-4367.
Liu et al., "KU675, a Concomitant Heat-Shock Protein Inhibitor of Hsp90 and Hsc70 that Manifests Isoform Selectivity for Hsp90alpha in Prostate Cancer Cells", Mol. Pharmacol., vol. 88, 2015, pp. 121-130.
Miyata et al., "The therapeutic target Hsp90 and cancer hallmarks", Current Pharmaceutical Design, vol. 19, 2013, pp. 347-365.
Neckers et al., "Hsp90 molecular chaperone inhibitors: are we there yet?", Clinical Cancer Research, vol. 18, 2012, pp. 64-76.
Neckers et al., "Stressing the development of small molecules targeting HSP90", Clinical Cancer Research: an official Jurnal of the American Association for Cancer Research, vol. 20, 2014, pp. 275-277.
Panaretou et al., "ATP binding and hydrolysis are essential to the function of the Hsp90 molecular chaperone in vivo", EMBO J., vol. 17, 1998, pp. 4829-4836.
Patel et al., "Paralog-selective Hsp90 inhibitors define tumor-specific regulation of HER2", Nature Chemical Biology, vol. 9, 2013, pp. 677-684.
Peterson et al., "The hERG channel is dependent upon the Hsp90alpha isoform for maturation and trafficking", Mol Pharm, vol. 9, 2012, pp. 1841-1846.
Powers et al., "Inhibitors of the heat shock response: biology and pharmacology", FEBS Lett., vol. 581, 2007, pp. 3758-3769.
Prince et al., "Client Proteins and Small Molecule Inhibitors Display Distinct Binding Preferences for Constitutive and Stress-Induced HSP90 Isoforms and Their Conformationally Restricted Mutants", PloS one, vol. 10, 2015, pp. e0141786.
Rohl et al., "The Chaperone Hsp90: Changing Partners for Demanding Clients", Trends Biochem. Sci, vol. 38, 2013, pp. 253-262.
Breedhar et al., "Hsp90 isoforms: functions, expression and clinical importance", FEBS Lett., vol. 562, 2004, pp. 11-15.
Travers et al., "HSP90 Inhibition: Two-Pronged Exploitation of Cancer Dependencies", Drug Discovery Today, vol. 17, 2012, pp. 242-252.
Trepel et al., "Targeting the Dynamic HSP90 Complex in Cancer", Nature Reveiws Cancer, vol. 10, 201, pp. 537-549.
Vaughan et al., "Understanding of the Hsp90 Molecular Chaperone Reaches New Heights", Nature Structural & Molecular Biology, S17, 2010, pp. 1400-1404.
Whitesell et al., "HSP90 and Chaperoning of Cancer", Nature Reviews Cancer, vol. 5, 2005, pp. 761-772.
Zubriene et al., "Thermodynamics of radicicol binding to human Hsp90 alpha and beta isoforms", Biophys. Chem., vol. 152, 2010, pp. 153-163.
Zuehlke et al., "Hsp90 and co-chaperones twist the functions of diverse client proteins", Biopolymers, vol. 93, 2010, pp. 211-217.
Bermejo et al., "PAMPA—a drug absorption in vitro model 7. Comparing rat in situ, Caco-2 and PAMPA permeability of fluoroquinolones", European Journal of Pharmaceutical Sciences, vol. 21, 2014, pp. 429-441.
Ernst et al., "Identification of Novel HSPalpha/beta isoform Selective Inhibitors Using Structure-Based Drug Design. Demonstration of Potential Utility in Treating CNS Disorders such as Huntingtons Disease", Journal of Medicinal Chemistry, vol. 57, 2014, pp. 3382-3400.
International Preliminary Report on Patentability for Application No. PCT/US2019/034672 dated Dec. 1, 2020 (6 pages).
International Search Report and Written Opinion for Application No. PCT/US19/34672 dated Sep. 27, 2019 (10 pages).
PubchemID, CID 114517554, create date Jan. 29, 2016, 7 pages.
Murray et al., "Fragment-Based Drug Discovery Applied to Hsp90. Discovery of Two Lead Series with High Ligand Efficiency", J. Med. Chem., vol. 53, 2010, pp. 5942-5955.
Woodhead et al., "Discovery of (2,4-dihydroxy-5-isopropylphenyl)-[5-(4 methylpiperazin-1ylmethyl)-1,3-dihydroisoindol-2-yl]methanone (AT13387), a novel inhibitor of the molecular chaperone Hsp90 by fragment based drug design", J. Med. Chem., vol. 53, 2010, pp. 5956-5969.

\* cited by examiner

AT13387

KUNB31

Hsp90α: 9.55 ± 1.08 µM
Hsp90β: 0.18 ± 0.01 µM
Grp94: 8.48 ± 0.97 µM

Hsp90α: 4 nM
Hsp90β: 6 nM
Grp94: 484 nM
Trap1: 791 nM

Hsp90α: 5 nM
Hsp90β: 5 nM
Grp94: >10 μM
Trap1: >10 μM

Hsp90β SELECTIVE INHIBITORS

CROSS-REFERENCE TO RELATED APPLICATIONS

This application is a U.S. national stage entry of International Patent Application No. PCT/US2019/034672, filed on May 30, 2019, which claims priority to U.S. Provisional Patent Application No. 62/730,402, filed on Sep. 12, 2018 and U.S. Provisional Patent Application No. 62/677,873, filed on May 30, 2018, the entire contents of each of which are fully incorporated herein by reference.

STATEMENT REGARDING FEDERALLY-SPONSORED RESEARCH OR DEVELOPMENT

This invention was made with government support under grant number CA222894 awarded by National Institutes of Health. The government has certain rights in the invention.

TECHNICAL FIELD

The present disclosure relates to novel Hsp90β selective inhibitors and the use thereof in treating cancer.

BACKGROUND OF THE INVENTION

The molecular chaperone, heat shock protein 90 kDa (Hsp90), regulates cellular homeostasis by assisting in the maturation of nascent polypeptides, the refolding of denatured proteins, and the disaggregation of protein aggregates. Hsp90 modulates the conformation of more than 300 client protein substrates into their biologically active conformation. Many of these client proteins, such as signaling proteins, are drivers of cancer progression, initiation, and/or metastasis. In fact, Hsp90's clients are associated with all 10 hallmarks of cancer and, in principle, Hsp90 inhibition should mimic the effects of combination therapies. As a result, Hsp90 has emerged as a promising target for the development of anti-cancer agents.

Hsp90 as a chemotherapeutic target is further supported by its upregulation during tumor transformation, maintenance, and progression. Despite its abundance in normal tissue, Hsp90 can be targeted selectively in tumor cells due to increased levels of the Hsp90 heteroprotein complex that reside within cancer cells and possess greater than 200 fold higher affinity for ATP/inhibitors than the Hsp90 homodimer found in normal cells. Consequently, Hsp90 inhibitors accumulate in tumor cells at significantly higher concentrations than normal tissue, and exhibit a large therapeutic window. As a result, Hsp90 has been extensively sought after as a therapeutic target for the treatment of cancer, and ultimately led to the investigation of 17 clinical candidates. Unfortunately, the clinical evaluation of these inhibitors has highlighted a number of complications. Complications observed with current Hsp90 inhibitors include the lack of translational efficacy, induction of the heat shock response (HSR) that results in increased levels of Hsp90, and off-target toxicities amongst others. Therefore, there remains a need for new Hsp90 inhibitors that overcome these disadvantages and unwanted side effects yet provide efficacy as anti-cancer agents.

BRIEF SUMMARY OF THE INVENTION

In one aspect, disclosed are compounds of formula (I):

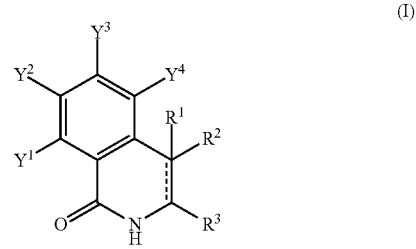

or a pharmaceutically acceptable salt thereof, wherein
the dashed line (-----) represents an optional double bond;
$R^1$ and $R^2$ are independently selected from hydrogen, halogen and cyano, with the proviso that $R^2$ is absent when the optional double bond is present;
$R^3$ is selected from $C_1$-$C_6$ alkyl, $C_3$-$C_8$ cycloalkyl, $C_1$-$C_6$ heteroalkyl, $C_3$-$C_8$ heterocycle, $C_1$-$C_6$ hydroxyalkyl, $C_2$-$C_6$ alkynyl, $C_2$-$C_6$ heteroalkynyl, $C_2$-$C_6$ alkenyl, $C_2$-$C_6$ heteroalkenyl, $C_1$-$C_6$ haloalkyl and alkylamino;
$Y^1$ is $C_1$-$C_6$ alkyl, $C_3$-$C_8$ cycloalkyl, $C_1$-$C_6$ heteroalkyl, $C_3$-$C_8$ heterocycloalkyl, halo, $C_1$-$C_6$ haloalkyl, —$NR^9R^{10}$ or —$SR^{11}$;
$R^9$ and $R^{10}$ are independently selected from hydrogen, $C_1$-$C_6$ alkyl, $C_3$-$C_8$ cycloalkyl, aryl, heteroaryl, $C_3$-$C_8$ heterocycle, $C_2$-$C_6$ alkenyl and $C_1$-$C_6$ heteroalkyl, wherein $R^9$ and $R^{10}$, together with the atoms to which they are attached, are optionally taken together to form an aryl, heteroaryl, cycloalkyl or heterocyclic ring;
$R^{11}$ is selected from $C_1$-$C_6$ alkyl, $C_3$-$C_8$ cycloalkyl, $C_1$-$C_6$ heteroalkyl, $C_3$-$C_8$ heterocycloalkyl, $C_1$-$C_6$ hydroxyalkyl, $C_2$-$C_6$ alkynyl, $C_2$-$C_6$ heteroalkynyl, $C_2$-$C_6$ alkenyl, $C_2$-$C_6$ heteroalkenyl, $C_1$-$C_6$ haloalkyl and aminoalkyl;
$Y^2$ is hydrogen, $C_1$-$C_6$ alkyl, $C_3$-$C_8$ cycloalkyl, $C_1$-$C_6$ heteroalkyl, $C_3$-$C_8$ heterocycle, halo, $C_1$-$C_6$ haloalkyl, amino or alkylamino;
$Y^3$ is $C_3$-$C_{14}$ heterocycle or $C_3$-$C_{14}$ heteroaryl;
$Y^4$ is hydrogen, $C_1$-$C_6$ alkyl, $C_1$-$C_6$ heteroalkyl, halo or $C_1$-$C_6$ haloalkyl; and
wherein each aryl, heteroaryl, cycloalkyl or heterocycle is independently unsubstituted or substituted with 1, 2, or 3 substituents independently selected from $C_1$-$C_4$ alkyl, hydroxy, $C_1$-$C_4$ alkoxy, halo, oxo, $C_1$-$C_4$ haloalkyl, and $C_1$-$C_4$ hydroxyalkyl.

In another aspect, the invention provides a pharmaceutical composition comprising a compound of formula (I), or a pharmaceutically acceptable salt thereof, and a pharmaceutically acceptable carrier.

In another aspect, the invention provides a method of inhibiting Hsp90 comprising contacting Hsp90 with an effective amount of a compound of formula (I).

In another aspect, the invention provides a method of treating a disease or disorder in a subject in need thereof, comprising administering to a subject in need thereof a therapeutically effective amount of the compound of formula (I), or a pharmaceutically acceptable salt thereof, or the pharmaceutical composition comprising a compound of formula (I). In some aspects, the disease or disorder may be cancer, a viral disease, an anti-inflammatory disease, an angiogenesis-related disease, a chemotherapy-induced toxicity or a protein misfolding or aggregation disease.

BRIEF DESCRIPTIONS OF THE DRAWINGS

FIG. 1A, FIG. 1B, FIG. 1C, and FIG. 1D are schematics of the network of water mediated hydrogen bonds in the Hsp90α of Hsp90β ATP-binding pockets. FIG. 1A shows the surface of the bottom of the Hsp90β ATP-binding pocket, demonstrating the depth of the exclusive Hsp90β pocket (PDB code: 1UYM). FIG. 1B shows the bottom of the Hsp90α ATP-binding pocket (PDB code: 2XAB). FIG. 1C shows the hydrogen bonding network at the bottom of the Hsp90β pocket (PDB code: 1UYM). FIG. 1D shows the hydrogen bonding network in the bottom of the Hsp90α binding pocket (PDB code: 2XAB).

Figure 10A:
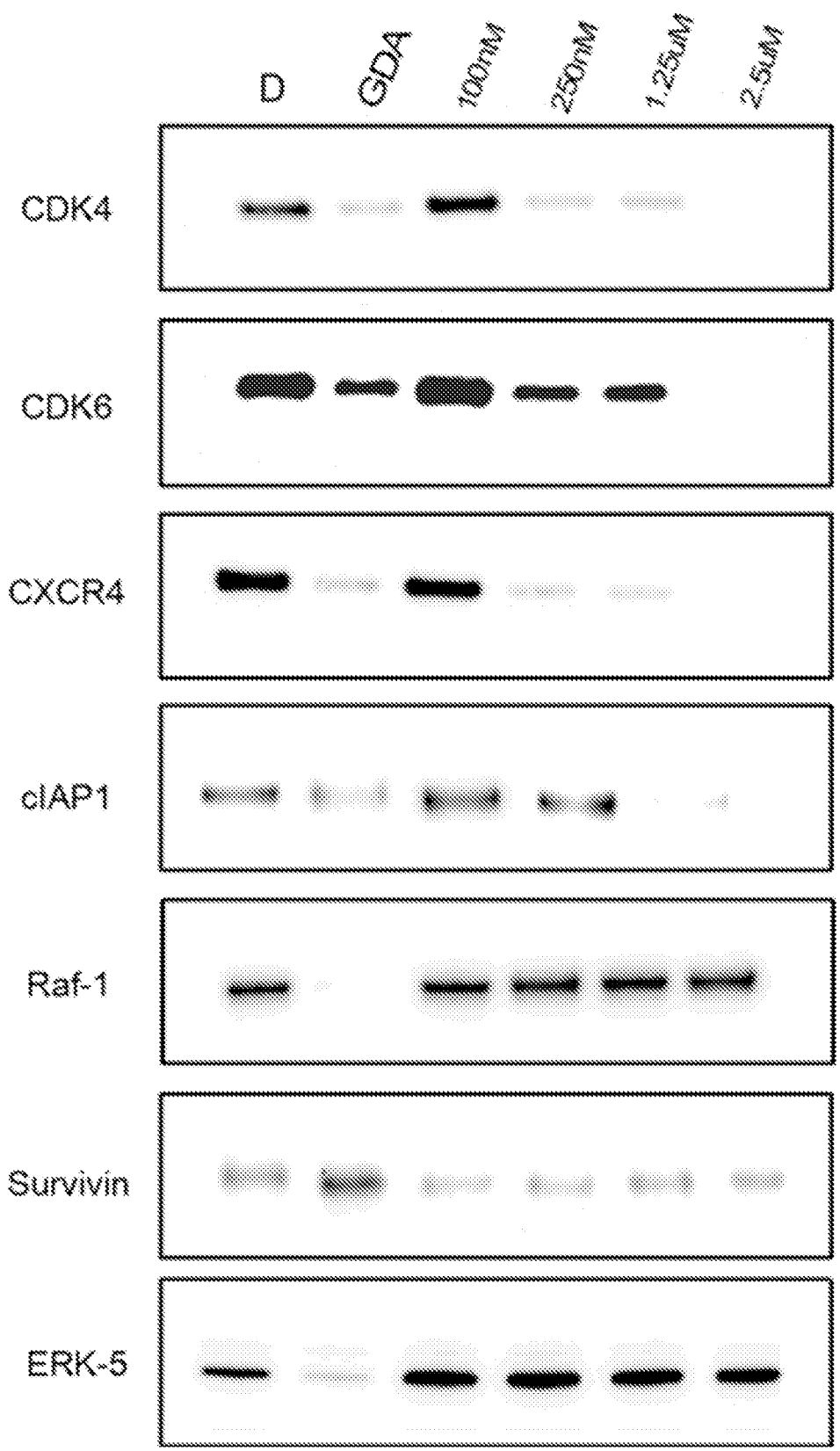
Figure 10B:
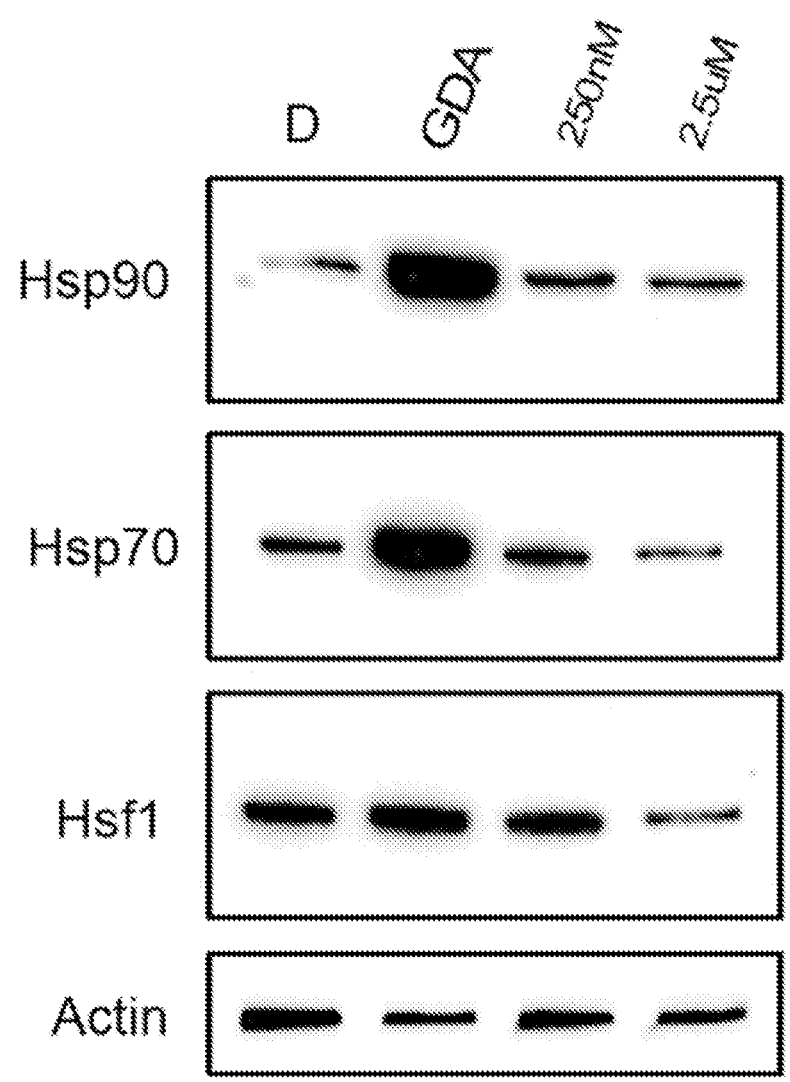
Figure 10C:
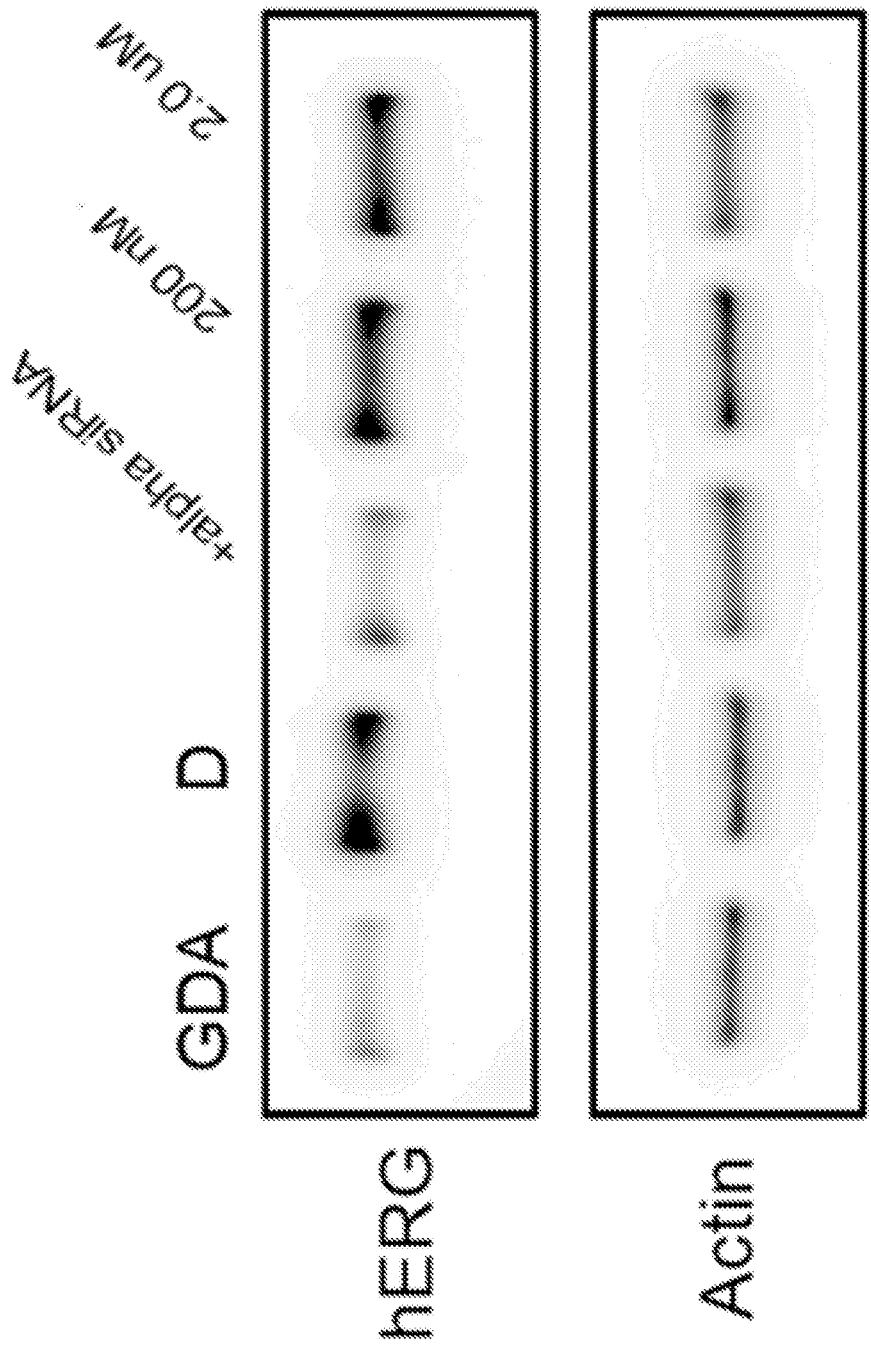

FIG. 10A, FIG. 10B, and FIG. 10C show the western blot analysis of cells treated with 6a. FIG. 10A and FIG. 10B show the western blot analysis following treatment of HCT-116 cells with 6a. 0.5 µM GDA was included as positive control and vehicle (D=DMSO) as negative control. FIG. 10C shows the Western blot analysis of hERG channel trafficking with 6a in hERG-HEK293 cells. Hsp90α siRNA was included as positive control and vehicle (lipofectamine) as negative control.

Figure 11:
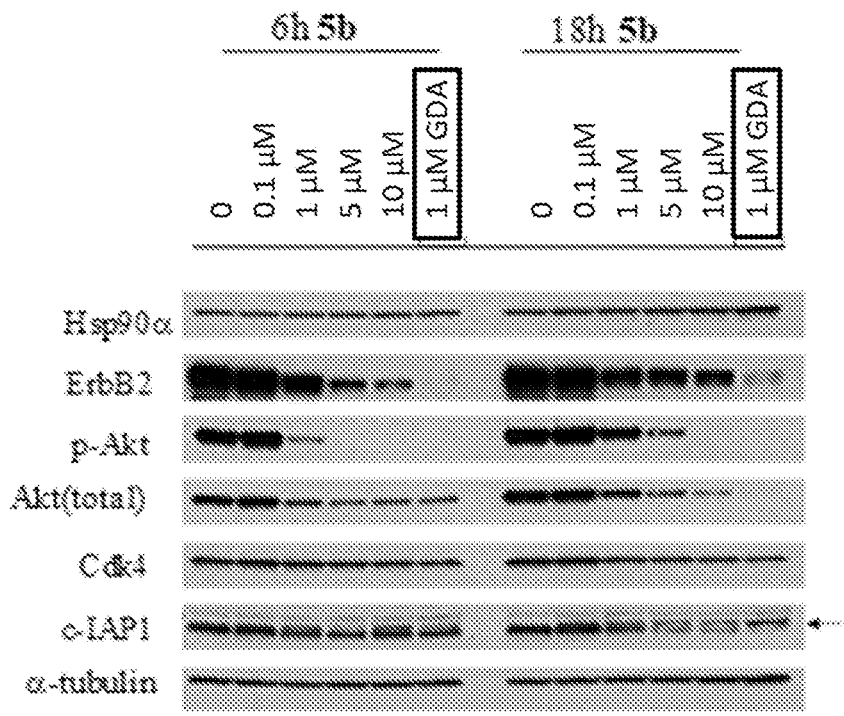
Figure 11:
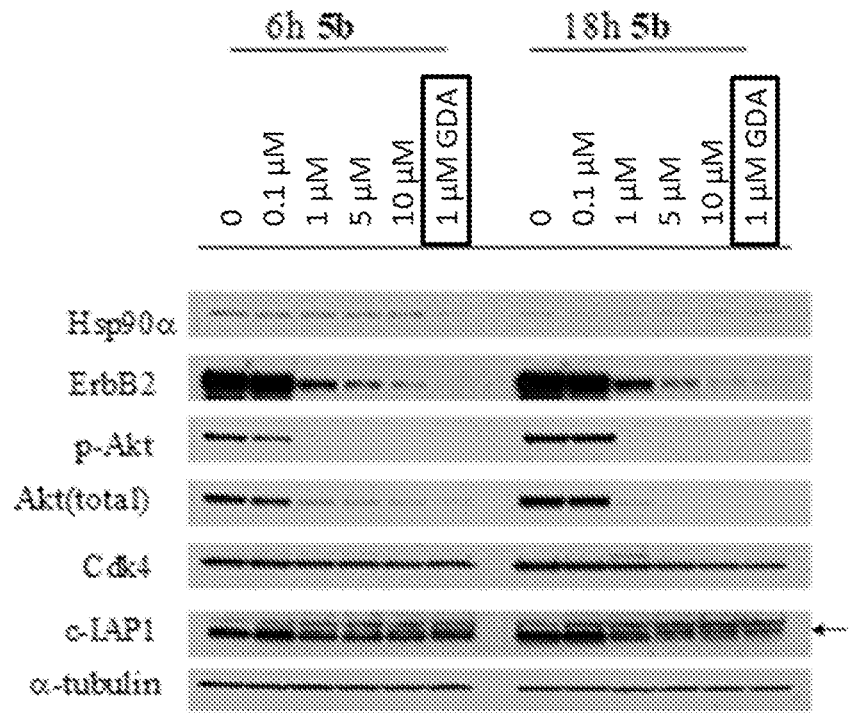

FIG. 11 shows the western blot analysis with 5b to study client protein degradation.

DETAILED DESCRIPTION OF THE INVENTION

Disclosed herein are compounds that are Hsp90β selective inhibitors, pharmaceutical compositions comprising the compounds, and methods of treating disease and disorders using the compounds and pharmaceutical compositions. The inhibitors are a series of isoquinolin-1(2H)-one compounds.

As disclosed herein, compounds of formula (I) provide increased affinity and selectivity for binding Hsp90β while also providing enhanced cellular efficacy over previously reported Hsp90 inhibitors. Compounds of formula (I) induced the degradation of Hsp90β-dependent clients without causing concomitant induction of Hsp90 and the pro-survival heat shock response. Additionally, compounds of formula (I) demonstrated selectivity towards cancer cell lines and can inhibit cancer at low nanomolar concentrations comparable to Hsp90 inhibitors undergoing clinical trials.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents, and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Definitions of specific functional groups and chemical terms are described in more detail below. For purposes of this disclosure, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched chain saturated hydrocarbon. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond and from 2 to 10 carbon atoms. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, means a divalent group derived from a straight or branched chain saturated hydrocarbon. Representative examples of alkylene include, but are not limited to, —CH$_2$—, —CH$_2$CH$_2$—, —CH$_2$CH$_2$CH$_2$—, —CH$_2$CH(CH$_3$)CH$_2$—, and CH$_2$CH(CH$_3$)CH(CH$_3$)CH$_2$—.

The term "alkylamino," as used herein, means at least one alkyl group, as defined herein, is appended to the parent molecular moiety through an amino group, as defined herein.

The term "alkynyl" or "alkyne" are interchangeable and refer to a hydrocarbon having at least one terminal triple bond. The term "alkynyl" may refer to a branched or an unbranched hydrocarbon group, or a substituted hydrocarbon chain, or as having further unsaturated bonds therein. In some embodiments, the alkynyl is n-propynyl, isopropynyl, n-butynyl, isobutynyl, t-butynyl, octynyl, decynyl and the like.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —NRxRy, wherein Rx and Ry may be hydrogen, alkyl, cycloalkyl, aryl, heteroaryl, heterocycle, alkenyl, or heteroalkyl. In the case of an aminoalkyl group or any other moiety where amino appends together two other moieties, amino may be —NRx-, wherein Rx may be hydrogen, alkyl, cycloalkyl, aryl, heteroaryl, heterocycle, alkenyl, or heteroalkyl.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl" as used herein, means a monovalent group derived from an all-carbon ring system containing zero heteroatoms as ring atoms, and zero double bonds. The all-carbon ring system can be a monocyclic, bicylic, or tricyclic ring system, and can be a fused ring system, a bridged ring system, or a spiro ring system, or combinations thereof. Examples of cycloalkyls include, but are not limited to, cyclopropyl, cyclobutyl, cyclopentyl, cyclohexyl, cycloheptyl and cyclooctyl. The cycloalkyl groups described herein can be appended to the parent molecular moiety through any substitutable carbon atom.

The term "cycloalkenyl," as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "cycloalkylene" as used herein, means a divalent group derived from an all-carbon ring system containing zero heteroatoms as ring atoms and zero double bonds, which attaches to the parent molecule at two different ring carbons atoms. The all-carbon ring system can be a monocyclic, bicylic, or tricyclic ring system, and can be a fused ring system, a bridged ring system, or a spiro ring system. Representative examples of cycloalkylene include, but are not limited to those derived from C3-10 rings, such as

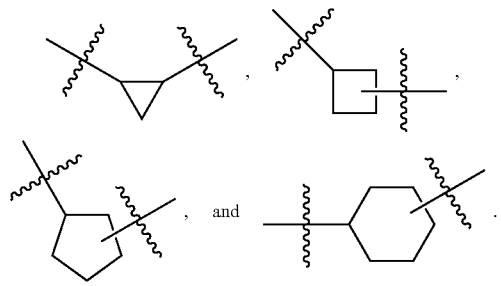

The term "halogen" or "halo" means a chlorine, bromine, iodine, or fluorine atom.

The term "haloalkyl," as used herein, means an alkyl, as defined herein, in which one, two, three, four, five, six, or seven hydrogen atoms are replaced by halogen. For example, representative examples of haloalkyl include, but are not limited to, 2-fluoroethyl, difluoromethyl, trifluoromethyl, 2,2,2-trifluoroethyl, 2,2,2-trifluoro-1,1-dimethylethyl, and the like.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroaryl," as used herein, means an aromatic heterocycle, i.e., an aromatic ring that contains at least one heteroatom selected from O, N, or S. A heteroaryl may contain from 5 to 12 ring atoms. A heteroaryl may be a 5- to 6-membered monocyclic heteroaryl, an 8- to 12-membered bicyclic heteroaryl or an 11- to 14-membered tricyclic heteroaryl. A 5-membered monocyclic heteroaryl ring contains two double bonds, and one, two, three, or four heteroatoms as ring atoms. Representative examples of 5-membered monocyclic heteroaryls include, but are not limited to, furanyl, imidazolyl, isoxazolyl, isothiazolyl, oxadiazolyl, oxazolyl, pyrazolyl, pyrrolyl, tetrazolyl, thiadiazolyl, thiazolyl, thienyl (thiophenyl), and triazolyl. A 6-membered heteroaryl ring contains three double bonds, and one, two, three or four heteroatoms as ring atoms. Representative examples of 6-membered monocyclic heteroaryls include, but are not limited to, pyridinyl, pyridazinyl, pyrimidinyl, pyrazinyl, and triazinyl. The bicyclic heteroaryl is an 8- to 12-membered ring system having a monocyclic heteroaryl fused to an aromatic, saturated, or partially saturated carbocyclic ring, or fused to a second monocyclic heteroaryl ring. Representative examples of bicyclic heteroaryls include, but are not limited to, pyrrolopyridinyl, pyrazolopyridinyl, 4,5,6,7-tetrahydro-1H-indolyl, 4,5,6,7-tetrahydro-1H-indazolyl, benzofuranyl, benzoxadiazolyl, 1,3-benzothiazolyl, benzimidazolyl, benzothienyl, indolyl, indazolyl, isoquinolinyl, naphthyridinyl, oxazolopyridine, quinolinyl, thienopyridinyl, and 5,6, 7,8-tetrahydroquinolinyl. The tricyclic heteroaryl is an 11- to 16-membered ring system having a monocyclic heteroaryl fused to at least two of an aromatic, saturated, or partially saturated carbocyclic ring or a second and third monocyclic heteroaryl ring, or one of an aromatic, saturated, or partially saturated carbocyclic ring and a second monocyclic heteroaryl ring. Representative examples of tricyclic heteroaryls include, but are not limited to, carbazolyl, tetrahydrocarbazolyl, carbolyl, tetrahydrocarbolyl, pyrroloquinolinyl, pyridoindolyl, quinoxalinyl, acridinyl, phenanthridinyl. The heteroaryl groups are connected to the parent molecular moiety through any substitutable carbon atom or any substitutable nitrogen atom contained within the groups.

The terms "heterocycle," "heterocyclic" or "heterocyclyl" refer generally to ring systems containing at least one heteroatom as a ring atom where the heteroatom is selected from oxygen, nitrogen, and sulfur. In some embodiments, a nitrogen or sulfur atom of the heterocycle is optionally substituted with oxo. Heterocycles may be a monocyclic heterocycle, a fused bicyclic heterocycle, a fused tricyclic heterocycle or a spiro heterocycle. The monocyclic heterocycle is generally a 4, 5, 6, 7, or 8-membered non-aromatic ring containing at least one heteroatom selected from O, N, or S. The 4-membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, homomorpholinyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The fused bicyclic heterocycle is a 7-12-membered ring system having a monocyclic heterocycle fused to a phenyl, to a saturated or partially saturated carbocyclic ring, or to another monocyclic heterocyclic ring, or to a monocyclic heteroaryl ring. Representative examples of fused bicyclic heterocycle include, but are not limited to, pyrrolopyridinyl, pyrazolopyridinyl, 4,5,6,7-tetrahydro-1H-indolyl, 4,5,6,7-tetrahydro-1H-indazolyl, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, 5,6,7,8-tetrahydroimidazo[1,2-a]pyrazinyl, and 1,2,3,4-tetrahydroquinolinyl. The fused tricycle heterocycle is an 11-14-membered ring system having a monocyclic heterocycle fused to at least two of: a phenyl, a saturated or partially saturated carbocyclic ring, another monocyclic heterocyclic ring, or a monocyclic heteroaryl ring. Representative examples of fused tricyclic heterocycle include, but are not limited to, 3,4,5,6,7,8-hexahydro-pyrido-indolyl, 1,2,3,4,5,6,7,8-octahydro-carbazole and 1,2,3,4-tetrahydro-carbazole. Spiro heterocycle means a 4-, 5-, 6-, 7-, or 8-membered monocyclic heterocycle ring wherein two of the substituents on the same carbon atom form a second ring having 3, 4, 5, 6, 7, or 8 members. Examples of a spiro heterocycle include, but are not limited to, 1,4-dioxa-8-azaspiro[4.5]decanyl, 2-oxa-7-azaspiro[3.5]nonanyl, 2-oxa-6-azaspiro[3.3]heptanyl, and 8-azaspiro[4.5]decane. The monocyclic heterocycle groups of the present invention may contain an alkylene bridge of 1, 2, or 3 carbon atoms, linking two nonadjacent atoms of the group. Examples of such a bridged heterocycle include, but are not limited to, 2,5-diazabicyclo[2.2.1]heptanyl, 2-azabicyclo[2.2.1]heptanyl, 2-azabicyclo[2.2.2]octanyl, and oxabicyclo[2.2.1]heptanyl. The monocyclic, fused bicyclic, and spiro heterocycle groups are connected to the parent molecular moiety through any substitutable carbon atom or any substitutable nitrogen atom contained within the group.

The term "hydroxyl" or "hydroxy," as used herein, means an —OH group.

The term hydroxyalkyl as used herein means an alkyl, as defined herein, in which a hydrogen atom is replaced by —OH. For example, representative examples of hydroxyalkyl include, but are not limited to those derived from $C_{1-6}$ alkyls, such as —CH$_2$OH, —CH$_2$CH$_2$OH, —CH$_2$CH$_2$CH$_2$OH, and the like.

Terms such as "alkyl," "cycloalkyl," "alkylene," "cycloalkylene," etc. may be preceded by a designation indicating the number of atoms present in the group in a particular instance (e.g., "$C_{1-4}$ alkyl," "$C_{1-4}$ alkylene"). These designations are used as generally understood by those skilled in the art. For example, the representation "C" followed by a subscripted number indicates the number of carbon atoms present in the group that follows. Thus, "$C_3$ alkyl" is an alkyl group with three carbon atoms (i.e., n-propyl, isopropyl). Where a range is given, as in "Ci-4," the members of the group that follows may have any number of carbon atoms falling within the recited range. A "$C_{1-4}$ alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

When a group is referred to as "unsubstituted" or not referred to as "substituted" or "optionally substituted", it means that the group does not have any substituents. If a group is described as being "optionally substituted", the group may be either (1) not substituted or (2) substituted. If a group is described as being optionally substituted with up to a particular number of non-hydrogen radicals, that group may be either (1) not substituted; or (2) substituted by up to that particular number of substituent groups or by up to the maximum number of substitutable positions on that group, whichever is less.

If substituents are described as being independently selected from a group, each substituent is selected independent of the other. Each substituent, therefore, may be identical to or different from the other substituent(s).

The term "≡" designates single bond (—) or a double bond (═).

The term

designates the point of attachment to the parent molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I. The structures also include zwitterionic forms of the compounds or salts of formula I where appropriate.

The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment).

As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

As used herein, "treat," "treating" and the like mean a slowing, stopping or reversing of progression of a disease or disorder when provided a composition described herein to an appropriate control subject. The terms also mean a reversing of the progression of such a disease or disorder to a point of eliminating or greatly reducing the cell proliferation. As such, "treating" means an application or administration of the compositions described herein to a subject, where the subject has a disease or a symptom of a disease, where the purpose is to cure, heal, alleviate, relieve, alter, remedy, ameliorate, improve or affect the disease or symptoms of the disease.

A "subject" or "patient" may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

As used herein, the terms "providing", "administering," and "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

2. COMPOUNDS

In some aspects, disclosed is a compound of formula (I):

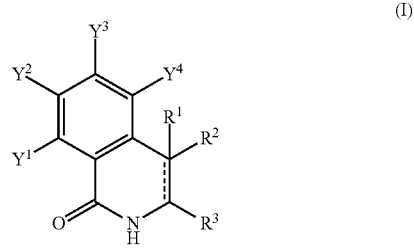

or a pharmaceutically acceptable salt thereof, wherein the dashed line ( ----- ) represents an optional double bond;

$R^1$ and $R^2$ are independently selected from hydrogen, halogen and cyano, with the proviso that $R^2$ is absent when the optional double bond is present;

$R^3$ is selected from $C_1$-$C_6$ alkyl, $C_3$-$C_8$ cycloalkyl, $C_1$-$C_6$ heteroalkyl, $C_3$-$C_8$ heterocycle, $C_1$-$C_6$ hydroxyalkyl, $C_2$-$C_6$ alkynyl, $C_2$-$C_6$ heteroalkynyl, $C_2$-$C_6$ alkenyl, $C_2$-$C_6$ heteroalkenyl, $C_1$-$C_6$ haloalkyl and alkylamino;

$Y^1$ is $C_1$-$C_6$ alkyl, $C_3$-$C_8$ cycloalkyl, $C_1$-$C_6$ heteroalkyl, $C_3$-$C_8$ heterocycloalkyl, halo, $C_1$-$C_6$ haloalkyl, —$NR^9R^{10}$ or —$SR^{11}$;

$R^9$ and $R^{10}$ are independently selected from hydrogen, $C_1$-$C_6$ alkyl, $C_3$-$C_8$ cycloalkyl, aryl, heteroaryl, $C_3$-$C_8$ heterocycle, $C_2$-$C_6$ alkenyl and $C_1$-$C_6$ heteroalkyl, wherein $R^9$ and $R^{10}$, together with the atoms to which they are attached, are optionally taken together to form an aryl, heteroaryl, cycloalkyl or heterocyclic ring;

$R^{11}$ is selected from $C_1$-$C_6$ alkyl, $C_3$-$C_8$ cycloalkyl, $C_1$-$C_6$ heteroalkyl, $C_3$-$C_8$ heterocycloalkyl, $C_1$-$C_6$ hydroxyalkyl, $C_2$-$C_6$ alkynyl, $C_2$-$C_6$ heteroalkynyl, $C_2$-$C_6$ alkenyl, $C_2$-$C_6$ heteroalkenyl, $C_1$-$C_6$ haloalkyl and aminoalkyl;

$Y^2$ is hydrogen, $C_1$-$C_6$ alkyl, $C_3$-$C_8$ cycloalkyl, $C_1$-$C_6$ heteroalkyl, $C_3$-$C_8$ heterocycle, halo, $C_1$-$C_6$ haloalkyl, amino or alkylamino;

$Y^3$ is $C_3$-$C_{14}$ heterocycle or $C_3$-$C_{14}$ heteroaryl;

$Y^4$ is hydrogen, $C_1$-$C_6$ alkyl, $C_1$-$C_6$ heteroalkyl, halo or $C_1$-$C_6$ haloalkyl; and wherein each aryl, heteroaryl, cycloalkyl or heterocycle is independently unsubstituted or substituted with 1, 2, or 3 substituents independently selected from $C_1$-$C_4$ alkyl, hydroxy, $C_1$-$C_4$ alkoxy, halo, oxo, $C_1$-$C_4$ haloalkyl, and $C_1$-$C_4$ hydroxyalkyl.

In some embodiments, $R^1$ and $R^2$ are hydrogen, with the proviso that $R^2$ is absent when the optional double bond is present. In some embodiments, the optional double bond is absent and $R^1$ and $R^2$ are hydrogen. In some embodiments, the optional double bond is present, $R^2$ is absent and $R^1$ is hydrogen.

In some embodiments, $R^3$ is $C_1$-$C_6$ alkyl, $C_1$-$C_6$ heteroalkyl, $C_2$-$C_6$ alkynyl or $C_1$-$C_6$ hydroxyalkyl. In some embodiments, $R^3$ is $C_1$-$C_6$ alkyl. In some embodiments, $R^3$ is $C_3$ alkyl. In some embodiments, $R^1$ and $R^2$ are hydrogen, the optional double bond is absent and $R^3$ is $C_3$ alkyl. In some embodiments, $R^1$ is hydrogen, the optional double bond is present, $R^2$ is absent and $R^3$ $C_3$ alkyl.

In some embodiments $Y^1$ is —$NR^9R^{10}$ wherein $R^9$ and $R^{10}$ are independently selected from hydrogen, $C_1$-$C_6$ alkyl, $C_3$-$C_8$ cycloalkyl, aryl, heteroaryl, $C_3$-$C_8$ heterocycle, $C_2$-$C_6$ alkenyl, $C_1$-$C_6$ heteroalkyl, or together with the atoms to which they are attached, are optionally taken together to form an aryl, heteroaryl, cycloalkyl or heterocyclic ring. In some embodiments, $Y^1$ is selected from the group consisting of

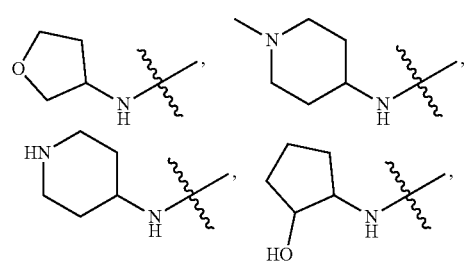

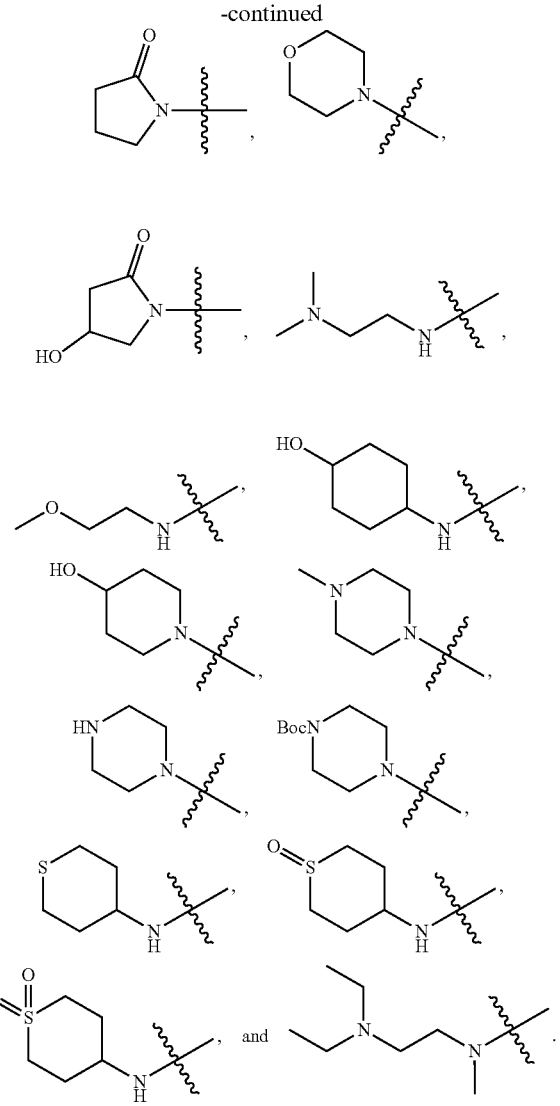

In some embodiments, $Y^1$ is

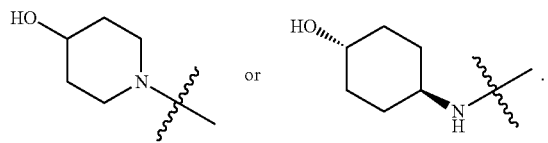 [SMILES: *N1CCC(O)CC1 ; *N[C@H]1CC[C@H](O)CC1]

In some embodiments, $Y^1$ is

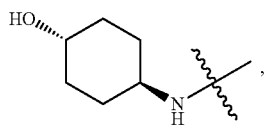 [SMILES: *N[C@H]1CC[C@H](O)CC1]

$R^1$ is hydrogen, the optional double bond is present, $R^2$ is absent and $R^3$ is $C_1$-$C_6$ alkyl, $C_1$-$C_6$ heteroalkyl or $C_1$-$C_6$ hydroxyalkyl. In some embodiments, $Y^1$ is selected from the group consisting of

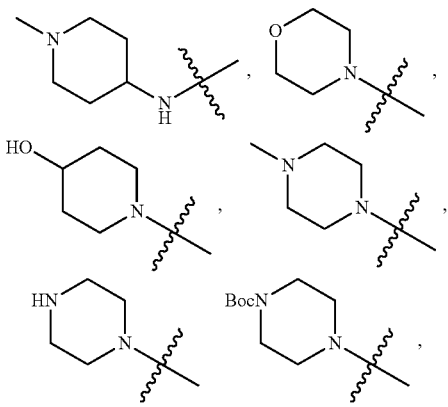

and R[1] is hydrogen, the optional double bond is present, R[2] is absent and R[3] is C₃ alkyl. In some embodiments, Y[1] is or

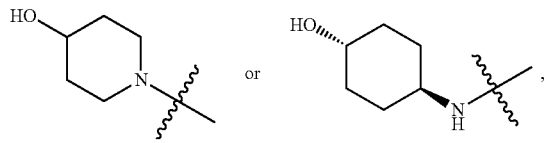 [SMILES: *N1CCC(O)CC1 ; *N[C@H]1CC[C@H](O)CC1]

R[1] and R[2] are hydrogen, the optional double bond is absent and R[3] is $C_1$-$C_6$ alkyl.

In some embodiments, Y[2] is hydrogen.

In some embodiments, Y[4] is hydrogen.

In some embodiments, Y[3] is selected from the group consisting of carbazole, tetrahydrocarbazole, indole, indazole, tetrahydroindole, tetrahydroindazole, pyrrolopyridine and pyrazolopyridine, wherein each aryl, heteroaryl, cycloalkyl or heterocyclic ring is independently unsubstituted or substituted with 1, 2, or 3 substituents independently selected from $C_1$-$C_4$ alkyl, hydroxy, $C_1$-$C_4$ alkoxy, halo, oxo, hydroxylamine, $C_1$-$C_4$ haloalkyl, and $C_1$-$C_4$ hydroxyalkyl. In some embodiments, Y[3] is

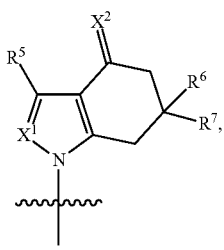

wherein X[1] is N or CR[4]; R[4] is hydrogen, $C_1$-$C_6$ haloalkyl, $C_1$-$C_6$ alkyl, or $C_1$-$C_6$ heteroalkyl; R[5] is hydrogen, $C_1$-$C_6$ alkyl, $C_1$-$C_6$ haloalkyl or COOR[1]; R[8] is $C_1$-$C_4$ alkyl; wherein R[4] and R[5], together with the atoms to which they are attached, are optionally taken together to form an aryl, heteroaryl, cycloalkyl or heterocyclic ring, wherein each aryl, heteroaryl, cycloalkyl or heterocycle is independently unsubstituted or substituted with 1, 2, or 3 substituents independently selected from $C_1$-$C_4$ alkyl, hydroxy, $C_1$-$C_4$ alkoxy, halo, oxo, $C_1$-$C_4$ haloalkyl, and $C_1$-$C_4$ hydroxyalkyl; X[2] is —O or —NOH; and R[6] and R[7] are independently selected from $C_1$-$C_4$ alkyl, $C_1$-$C_4$ haloalkyl and hydrogen, wherein

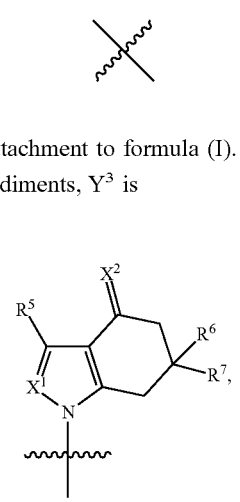

is the point of attachment to formula (I).

In some embodiments, Y[3] is

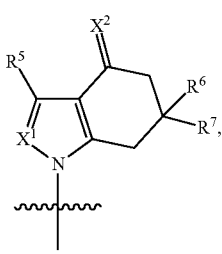

wherein R[6] and R[7] are independently selected from $C_1$-$C_4$ alkyl. In some embodiments, Y[3] is

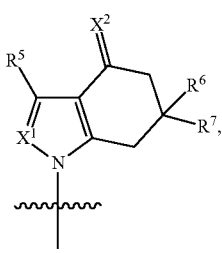

wherein R[6] and R[7] are methyl.

In some embodiments, Y[3] is

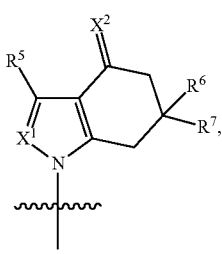

wherein X[2] is —O and R[6] and R[7] are methyl.

In some embodiments, Y[3] is wherein $R^5$ is hydrogen or $C_1$-$C_6$ alkyl. In some embodiments, $Y^3$ is

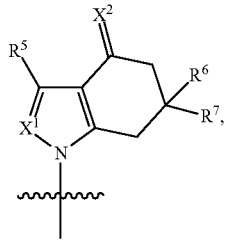

wherein $R^5$ is methyl. In some embodiments, $Y^3$ is

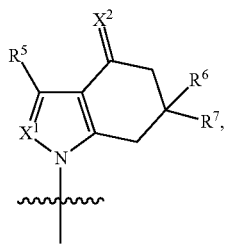

wherein $R^5$, $R^6$ and $R^7$ are methyl and $X^2$ is —O.
In some embodiments, $Y^3$ is

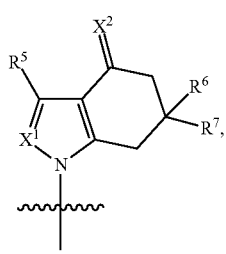

wherein $X^1$ is N. In some embodiments, $Y^3$ is

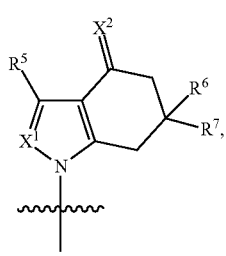

wherein $X^1$ is N, $R^5$, $R^6$ and $R^7$ is yare methyl and is —O.

In some embodiments, $Y^3$ is

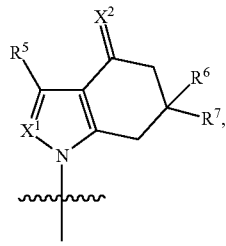

wherein $X^1$ is $CR^4$. In some embodiments, $Y^3$ is

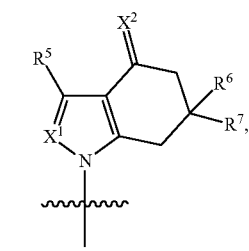

wherein $X^1$ is $CR^4$ and $R^4$ is hydrogen. In some embodiments, $Y^3$ is

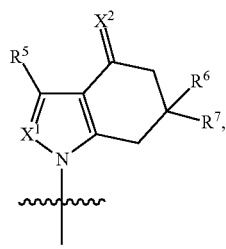

wherein $X_1$ is $CR^4$, $R^4$ is hydrogen, $R^5$, $R^6$ and $R^7$ are methyl and $X^2$ is —O. In some embodiments, $Y^3$ is

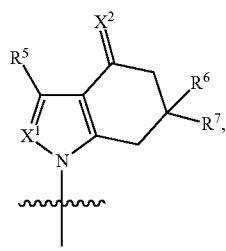

wherein $R^6$ and $R^7$ are methyl, $X^2$ is —O, $X^1$ is $CR^4$ and $R^4$ and $R^5$ are $C_1$-$C_6$ alkyl, or $C_1$-$C_6$ heteroalkyl and together with the atoms to which they are attached are taken together to form an aryl or heteroaryl ring.

In some embodiments, $Y^1$ is

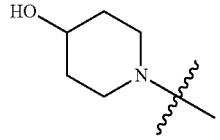 or 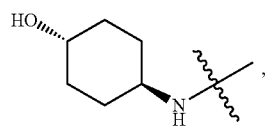, $R^1$ and $R^2$ are hydrogen, the optional double bond is absent, $R^3$ is $C_3$ alkyl, $Y^3$ is

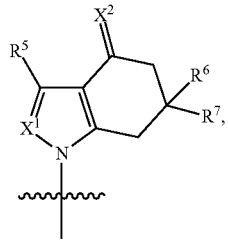

wherein $X^1$ is $CR^4$, $R^4$ is hydrogen, $R^5$, $R^6$ and $R^7$ are methyl, $Y^2$ and $Y^4$ are hydrogen and $X^2$ is —O.

In some embodiments, $Y^1$ is

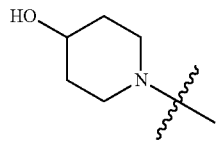 or 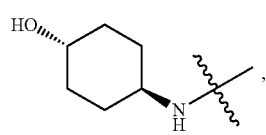, $R^1$ is hydrogen, the optional double bond is present, R is absent, $R^3$ is $C_3$ alkyl, $Y^3$ is

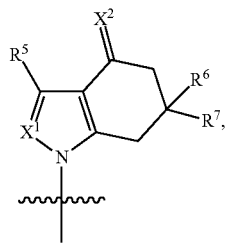

wherein $X^1$ is $CR^4$, $R^4$ is hydrogen, $R^5$, $R^6$ and $R^7$ are methyl, $Y^2$ and $Y^4$ are hydrogen and $X^2$ is —O.

In some embodiments, the compound of formula (I) is selected from the group consisting of:

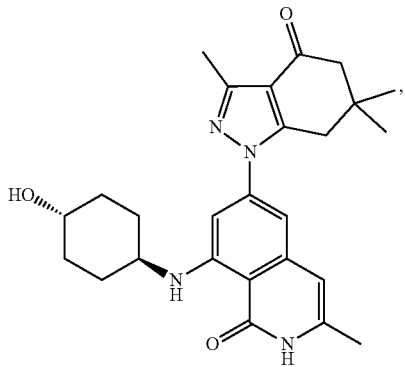

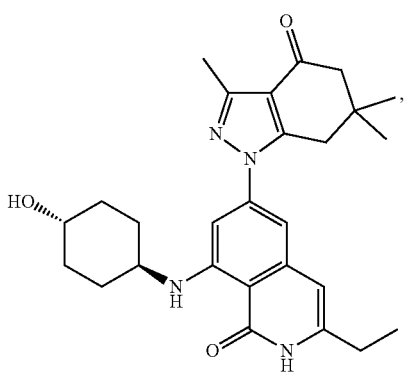

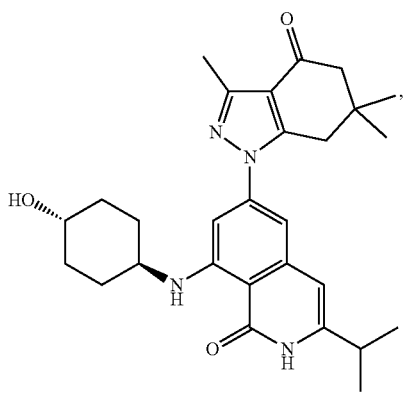

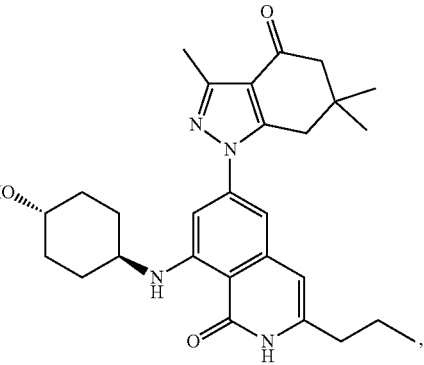

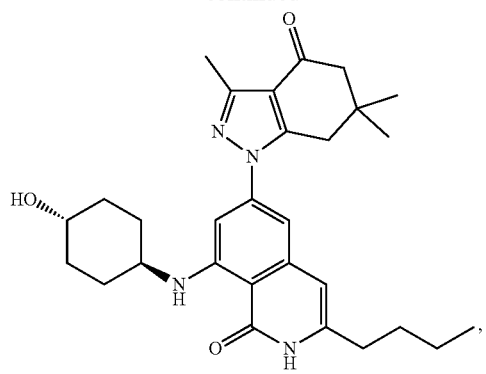
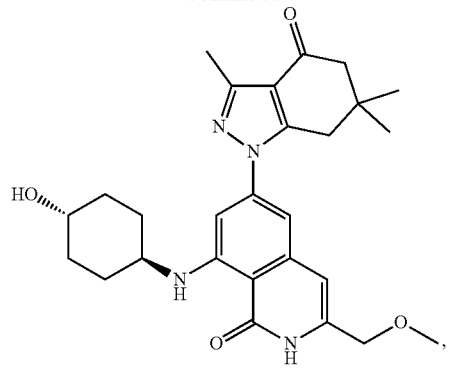
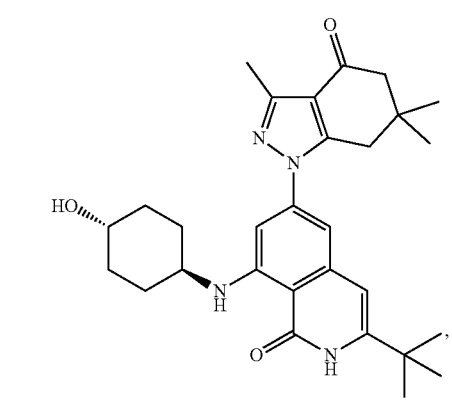
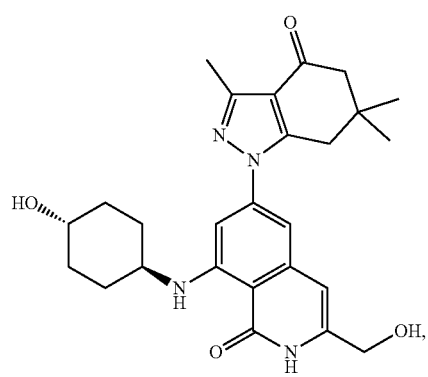
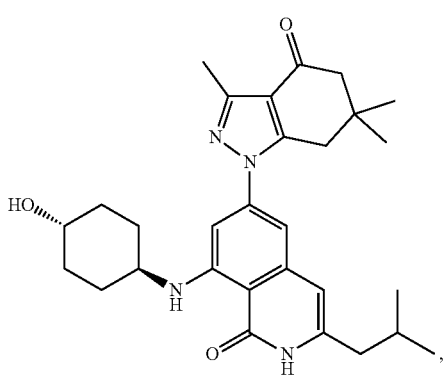
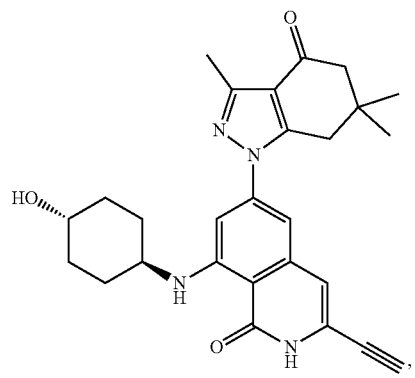
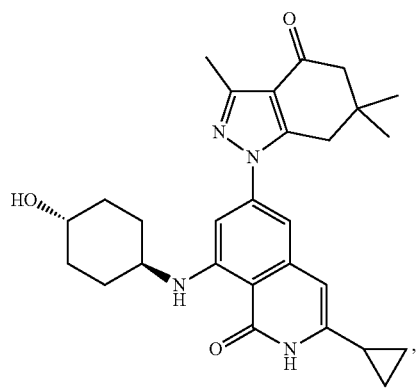
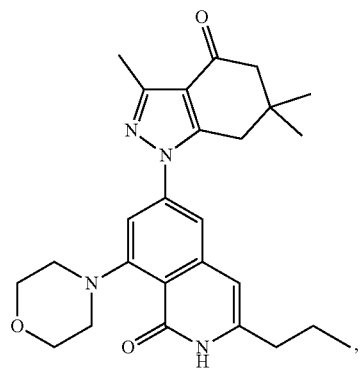

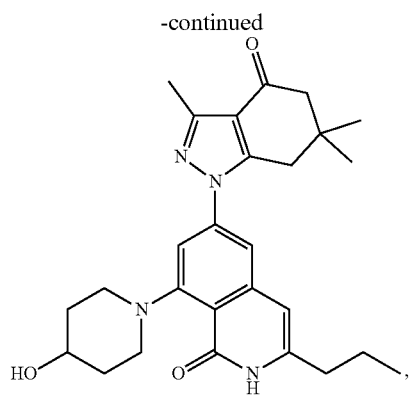
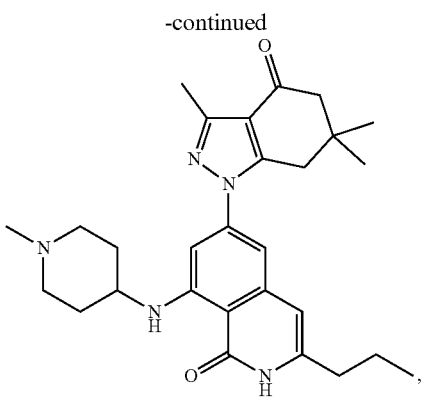
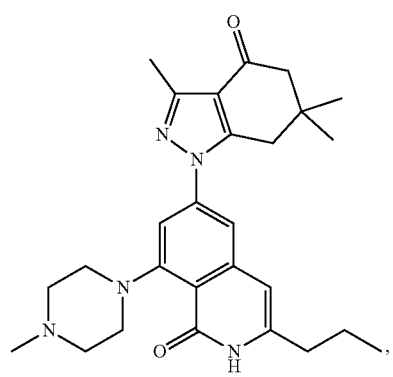
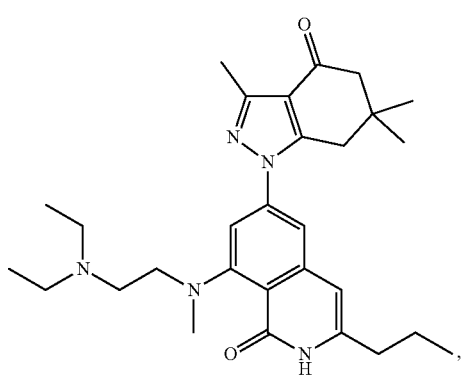
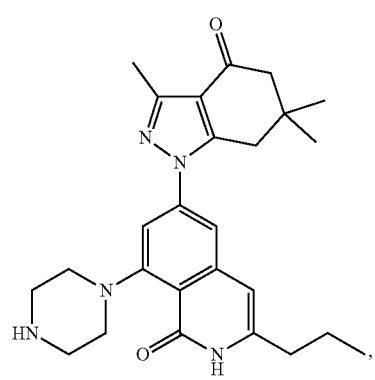
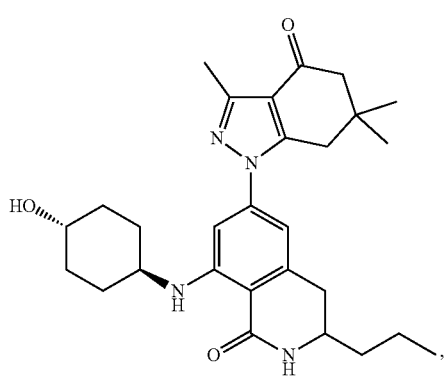
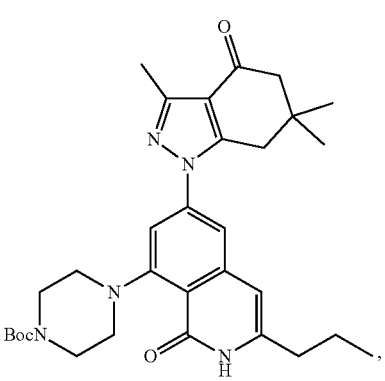
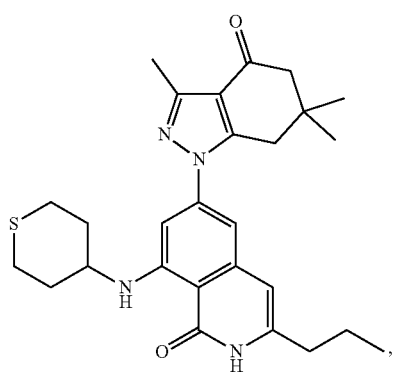

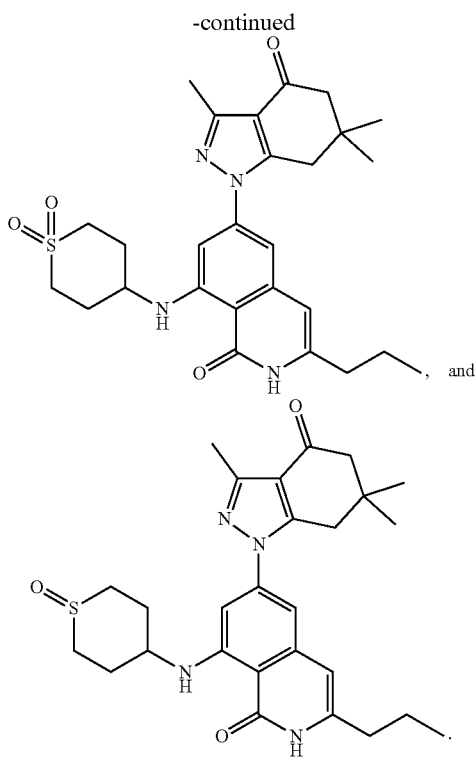

The compounds of the present disclosure may exist as stereoisomers wherein asymmetric or chiral centers are present. A stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers may include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds of the present disclosure may possess tautomeric forms, as well as geometric isomers, and that these also constitute embodiments of the disclosure.

The present disclosure also may include isotopically-labeled compounds, which may be identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. General Synthesis

Abbreviations which have been used in the descriptions of the Schemes that follow are:

| | |
|---|---|
| BOC | tert-butoxycarbonyl |
| DIPEA | diisopropylethylamine |
| DMF | Dimethylformamide |
| DMSO | Dimethyl sulfoxide |
| h or hr | hour |
| psi | pounds per square inch |

Compounds of formula (I) can be synthesized as shown in Schemes 1-3.

Scheme 1

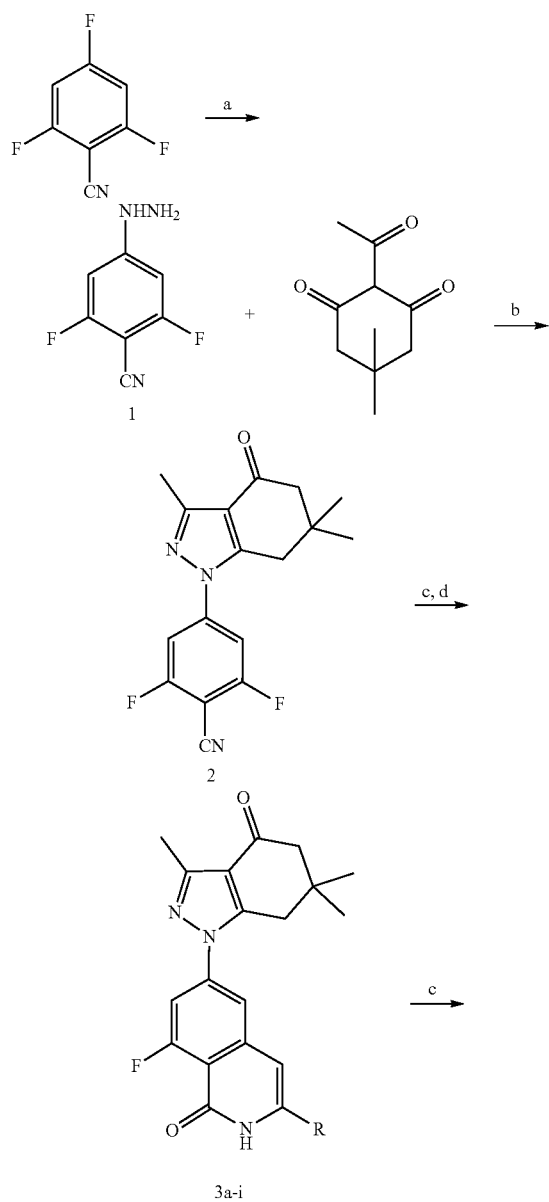

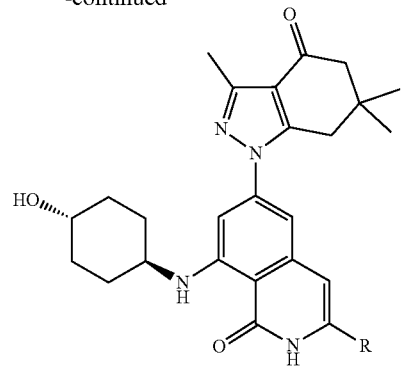

3a, 4a: R = Methyl
3b, 4b: R = Ethyl
3c, 4c: R = Isopropyl
3d, 4d: R = Propyl
3e, 4e: R = Butyl
3f, 4f: R = t-butyl 3g, 4g: R = (isobutyl)

3h, 4h: R = Cyclopropyl
3i, 4i: R = CH$_2$OCH$_3$ a) NH$_2$NH$_2$•H$_2$O, Ethanol, 60° C.
b) 2-Acetyldimedone, Ethanol, reflux
c) β-ketoester, K$_2$CO$_3$, DMF, 70° C.
d) H$_2$SO$_4$:Water:Acetic Acid (2:1:7), 130° C., 6 h.
e) trans-cyclohexanolamine, DIPEA, DMSO, 140° C. 12 h.

As shown in Scheme 1, synthesis of the compounds of formula (I) may commence via installation of the saturated indazolone. 2,4,6-Trifluorobenzonitrile (1) may be treated with hydrazine hydrate and 2-acetyl dimedone to produce 2,6-difluoro-4-(3,6,6-trimethyl-4-oxo-4,5,6,7-tetrahydro-1H-indazol-1-yl)benzonitrile, which can be subsequently exposed to a variety of β-ketoesters containing the desired R-groups in the presence of potassium carbonate to ultimately give the β-ketoester substituted benzonitriles, 3a-i. The resulting amides can undergo condensation and cyclization upon treatment with acetic and sulfuric acids, to yield intermediates 3a-i. The trans-4-aminocyclohexanol moiety can be installed via an S$_N$Ar reaction in the presence of diisopropylethylamine to furnish the final products, 4a-i.

Scheme 2

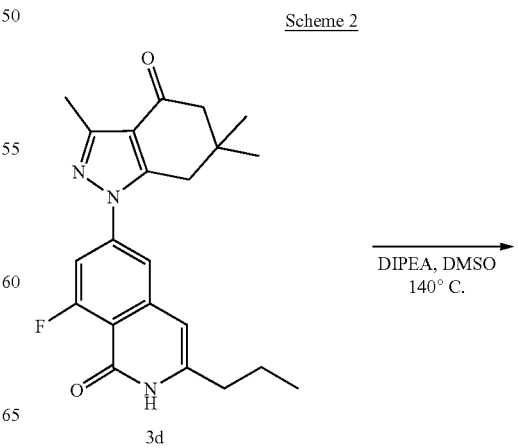

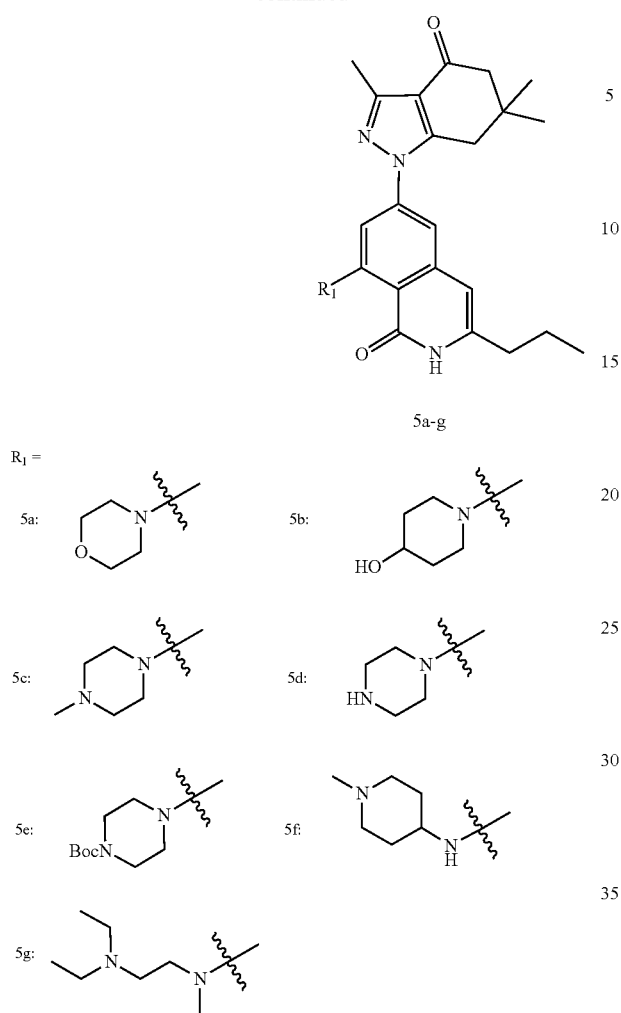

5a-g

R₁ =

5a: morpholine
5b: 4-hydroxypiperidine
5c: 4-methylpiperazine
5d: piperazine
5e: Boc-piperazine
5f: 4-methylamino-1-methylpiperidine
5g: N,N-diethyl-N'-methylethylenediamine As shown in Scheme 2, compounds 5a-g may be prepared from 3d by addition of the amine moieties under reaction conditions promoting an S$_N$Ar reaction in the presence of diisopropylethylamine to furnish the final products, 5a-g.

Scheme 3

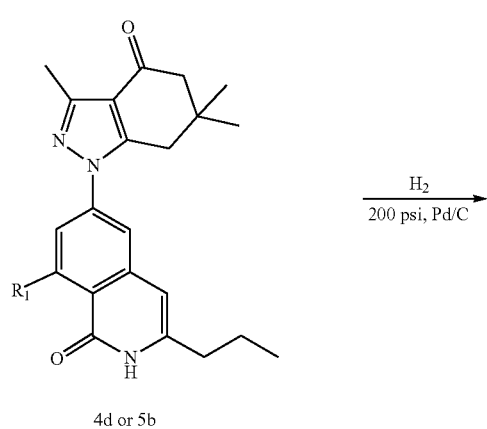

4d or 5b

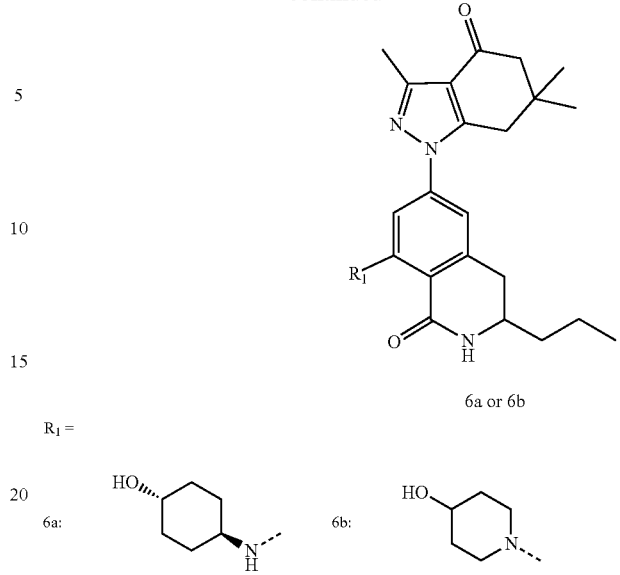

6a or 6b

R₁ =

6a: trans-4-hydroxycyclohexylamine
6b: 4-hydroxypiperidine

As shown in Scheme 3, compounds containing a saturated lactam ring may be prepared from the corresponding compound with an unsaturated lactam ring, as synthesized in Schemes 1 or 2 by Pd/C catalyzed hydrogenation.

The compounds and intermediates may be isolated and purified by methods well-known to those skilled in the art of organic synthesis. Examples of conventional methods for isolating and purifying compounds may include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step may vary depending on the particular reactants employed and substituents present in the reactants used. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature. Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4th ed.), John Wiley & Sons, NY (2006), which is incorporated herein by reference in its entirety. Synthesis of the compounds of the invention may be accomplished by methods analogous to those described in the synthetic schemes described hereinabove and in specific examples.

When an optically active form of a disclosed compound is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it may be obtained by carrying out one of the above procedures using a pure geometric isomer as a starting material, or by resolution of a mixture of the geometric isomers of the compound or intermediates using a standard procedure such as chromatographic separation.

It will be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. METHODS OF USE a. Inhibiting Hsp90

The present disclosure provides methods of inhibiting Hsp90. The methods comprise contacting Hsp90 with an effective amount of a compound of formula (I) wherein $R^1$, $R^2$, $R^3$, $Y^1$, $Y^2$, $Y^3$ and $Y^4$ are as defined herein.

Many of the conventional Hsp90 inhibitors bind the N-terminal nucleotide binding site and inhibit all four Hsp90 isoforms (pan-inhibition) with similar affinity. The Hsp90B isoform is constitutively expressed in the cytoplasm, whereas Hsp90α is inducible and expressed in the cytosol upon exposure to cellular stress. There are two organelle specific isoforms, glucose regulated protein 94 (Grp94) and tumor necrosis factor receptor-associated protein 1 (Trap-1). Glucose regulated protein 94 (Grp94) resides in the endoplasmic reticulum whereas tumor necrosis factor receptor-associated protein 1 (Trap-1) localizes to the mitochondria. Recent studies have shown that the unwanted side effects of the conventional Hsp90 inhibitors are due to inhibition of specific isoforms. Isoform-selective inhibitors may prove useful to identify isoform-dependent substrates and also to overcome the liabilities associated with pan inhibition.

In some embodiments, the compounds of formula (I) inhibit Hsp90β. In some embodiments the compounds of formula (I) have increased affinity for Hsp90β in comparison to the other isoforms. In some embodiments the compounds of formula (I) have increased specificity for Hsp90β in comparison to the other isoforms. The compounds of formula (I) may have >20-fold selectivity for Hsp90β, >50-fold selectivity for Hsp90β, >100-fold selectivity for Hsp90β, >200-fold selectivity for Hsp90β, >300-fold selectivity for Hsp90β or >400-fold selectivity for Hsp90β.

b. Treating Diseases and Disorders

The present disclosure also provides methods of treating a disease or disorder. The methods comprise administering to a subject in need thereof a therapeutically effective amount of the a compound of formula (I) wherein $R^1$, $R^2$, $R^3$, $Y^1$, $Y^2$, $Y^3$ and $Y^4$ are as defined herein or a pharmaceutically acceptable salt thereof, or the pharmaceutical composition comprising a compound of formula (I).

The compounds of the invention are inhibitors of Hsp90 and are thus useful in the treatment of diseases which are mediated by excessive or inappropriate Hsp90 activity including cancers; viral diseases such as hepatitis C (HCV); anti-inflammatory diseases such as rheumatoid arthritis, asthma, MS, type I diabetes, lupus, psoriasis and inflammatory bowel disease; cystic fibrosis; angiogenesis-related diseases; chemotherapy-induced toxicity; protein misfolding or aggregation diseases, for example, scrapie/CJD, Huntington's disease and Alzheimer's disease.

In some embodiments, the disease or disorder is cancer. Many different cancer types and subtypes rely on pathways mediated by the Hsp90 protein for proliferation and tumor development thus inhibitors of the highly conserved Hsp90 protein may be used to treat a wide variety of cancers. In some embodiments, the cancer may be a carcinoma, sarcoma, lymphoma, leukemia, melanoma, mesothelioma, multiple myeloma, or seminoma. In certain embodiments, the cancer is leukemia.

The cancer may be a cancer of the bladder, blood, bone, brain, breast, cervix, colon/rectum, endometrium, head and neck, kidney, liver, lung, muscle tissue, ovary, pancreas, prostate, skin, spleen, stomach, testicle, thyroid or uterus. In certain embodiments, the cancer is of the colon, breast, bladder, prostate or kidney.

The cancers may be cancers which are sensitive to Hsp90 inhibition; including human breast cancers (e.g. primary breast tumors, node-negative breast cancer, invasive duct adenocarcinomas of the breast, non-endometrioid breast cancers), mantle cell lymphomas, colorectal and endometrial cancers.

The cancers may be ErbB2-positive. Cancers which are commonly ErbB2 positive include: breast, prostate, lung, and gastric cancer; chronic myeloid leukemia; androgen receptor dependent prostate cancer; Flt3-dependent acute myeloid leukemia; melanoma associated with BRAF mutation; multiple myeloma; and gastrointestinal stromal tumors (GIST).

c. Administration

Compounds of the present disclosure, or pharmaceutically acceptable salts thereof, may be administered to subjects by a variety of methods. In any of the uses or methods described herein, administration may be by various routes known to those skilled in the art, including without limitation oral, inhalation, intravenous, intramuscular, topical, subcutaneous, systemic, and/or intraperitoneal administration to a subject in need thereof.

The amount of the compound of the present disclosure, or pharmaceutically acceptable salt thereof, required for use in treatment will vary not only with the particular compound or salt selected but also with the route of administration, the nature and/or symptoms of the disease and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein.

In some embodiments, the compounds, or pharmaceutically acceptable salts thereof, or pharmaceutical compositions as disclosed herein may be administered by oral administration or parenteral administration (including, but not limited to, subcutaneous, intramuscular, intravenous, intraperitoneal, intracardiac and intraarticular injections).

In general, however, a suitable dose will often be in the range of from about 0.01 mg/kg to about 100 mg/kg, such as from about 0.05 mg/kg to about 10 mg/kg. For example, a suitable dose may be in the range from about 0.10 mg/kg to about 7.5 mg/kg of body weight per day, such as about 0.10 mg/kg to about 0.50 mg/kg of body weight of the recipient per day, about 0.10 mg/kg to about 1.0 mg/kg of body weight of the recipient per day, about 0.15 mg/kg to about 5.0 mg/kg of body weight of the recipient per day, about 0.2 mg/kg to 4.0 mg/kg of body weight of the recipient per day. The compound may be administered in unit dosage form; for example, containing 1 to 100 mg, 10 to 100 mg or 5 to 50 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of a compound of the present invention, or pharmaceutically acceptable salts thereof, can be determined by comparing their in vitro activity, and in vivo activity in animal models.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, FIPLC assays or bioassays can be used to determine plasma concentrations. Dosage intervals can also be determined using MEC value. Compositions should be administered using a regimen, which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the symptoms to be treated and the route of administration. Further, the dose, and perhaps dose frequency, will also vary according to the age, body weight, and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

A therapeutically effective amount of a compound disclosed herein, or a pharmaceutically acceptable salt thereof, may be administered alone or in combination with a therapeutically effective amount of at least one additional therapeutic agents. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therapies may be used in conjunction with the compounds of the present disclosure. The second therapy may be a combination of a second therapeutic agent or may be a second therapy not connected to administration of another agent. Such second therapies include, but are not limited to, surgery, immunotherapy, radiotherapy, or a second chemotherapeutic agent.

4. PHARMACEUTICAL COMPOSITIONS

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration may have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds may be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

5. EXAMPLES

It will be readily apparent to those skilled in the art that other suitable modifications and adaptations of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

Abbreviations used in the examples that follow are:

| BOC | tert-butoxycarbonyl |
| DCM | dichoromethane |
| DIPEA | diisopropylethylamine |
| DMF | dimethylformamide |
| DMSO | dimethyl sulfoxide |
| ESI | electro-spray ionization |
| h or hr | hour |
| HRMS | high resolution mass spectrometry |
| Hz | Hertz |
| MeOH | methanol |
| ppm | parts per million |
| psi | pounds per square inch |
| rt or r.t. | room temperature |
| TLC | thin layer chromatography |

Example 1: Compound Synthesis

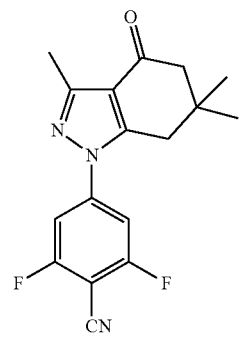

2,6-difluoro-4-(3,6,6-trimethyl-4-oxo-4,5,6,7-tetrahydro-1H-indazol-1-yl)benzonitrile (2)

a) To a solution of 2,4,6-trifluorobenzonitrile (1) (5 g, 31.8 mmol, 1 eq.) in 50 mL of ethanol heated to 60° C., was added hydrazine hydrate (50-60% solution) (3.4 g, 63.6 mmol, ~2 eq.). Upon consumption of 1 (monitored using TLC), the solvent was evaporated from the reaction mixture under vacuum. To the remaining white semisolid mass was added 50 mL water and the organic mass was extracted with ethyl acetate (3×50 mL). The combined organic fractions were combined and washed with brine (100 mL). The organic fraction was separated and dried over sodium sulfate. Subsequently, evaporation of the organic layer provided ~6.5 g of white mixture that was utilized in the next reaction without further purification.

b) The above obtained crude product (6 g, 35.5 mmol, 1 eq.) was suspended in 100 mL ethanol in a 250 mL capacity sealed reaction vessel. 2-acetyldimedone (16.1 g, 88.75 mmol, 2.5 eq), an orange colored oil, was subsequently added to the reaction vessel which was sealed and heated to 100° C. for 6 hr. The reaction vessel was allowed to cool to rt, ethanol was removed in vacuo, and the remaining mass was extracted with ethyl acetate (3×100 mL) and water (200 mL). Organic layers were combined and washed with 100 mL water. Separated organic layer was dried using sodium sulfate and adsorbed onto silica, and purified using column chromatography ($SiO_2$, 3:2 hexanes/ethyl acetate) to afford 2,6-difluoro-4-(3,6,6-trimethyl-4-oxo-4,5,6,7-tetrahydro-1H-indazol-1-yl)benzonitrile (2) (5.8 g, 52%) as light-yellow solid. 1H NMR (500 MHz, Chloroform-d) δ 7.39-7.33 (m, 2H), 2.91 (s, 2H), 2.55 (s, 3H), 2.45 (s, 2H), 1.17 (s, 6H). $^{13}$C NMR (126 MHz, Chloroform-d) δ 192.9, 164.5 (d, J=6.5 Hz), 162.5 (d, J=6.4 Hz), 151.8, 149.4, 144.5-144.1 (m), 118.8, 108.5, 106.2 (d, J=4.1 Hz), 106.0 (d, J=3.9 Hz), 99.9, 52.0, 38.0, 36.0, 28.4 (2), 13.3. HRMS (ESI) m/z [M+H] calculated for $C_{17}H_{16}F_2N_3O$, 316.1261, found 316.1237.

General procedure for 3a-3i: To a solution of benzonitrile (2) (200 mg, 0.64 mmol, 1 eq) in 2 mL DMF in a 10 mL round bottom flask, the desired β-ketoethylester (0.76 mmol, 1.2 eq), and potassium carbonate (106 mg, 0.76 mmol, 1.2 eq) was added and stirred at 70° C. until 2,6-difluoro-4-(3,6,6-trimethyl-4-oxo-4,5,6,7-tetrahydro-1H-indazol-1-yl) benzonitrile was consumed, as determined by TLC. Upon completion, the reaction was acidified to pH 5 with 1N aq. HCl. Subsequently, 10 mL NH$_4$Cl saturated solution was added and extracted using ethyl acetate (3×10 ml). The combined organic fractions were washed with brine and dried over sodium sulfate. The organic fraction was then adsorbed on silica and quick flash column chromatography was performed using 3:7 ethyl acetate/hexane as solvent system. The product fractions were collected, dried and the resulting mass was utilized in the further reaction.

The crude mass obtained (~210 mg) was taken in a 15 ml sealed reaction vessel, to which 1 mL sulfuric acid (36N), 8.5 mL acetic acid and 0.5 mL water were added. The vessel was sealed and heated to 140° C. for 8 h. The reaction was then quenched with addition of the reaction mixture to 100 mL water. The precipitated solid was filtered under vacuum to yield brown colored solid cake that was dried, dissolved in ethyl acetate and adsorbed onto silica for further purification. Upon column chromatography with 5:5 hexane/ethyl acetate, the desired product was isolated as white solid (30-40% yield).

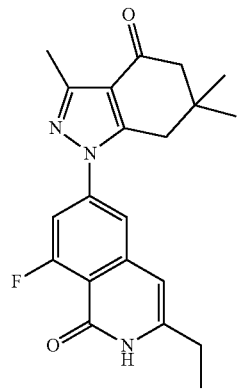

3-ethyl-8-fluoro-6-(3,6,6-trimethyl-4-oxo-4,5,6,7-tetrahydro-1H-indazol-1-yl)isoquinolin-1(2H)-one (3b): 77 mg, Yield: 36%; $^1$H NMR (600 MHz, Chloroform-d) δ 9.51 (s, 1H), 7.41 (d, 65 J=2.0 Hz, 1H), 7.27 (d, J=0.6 Hz, 1H), 6.33 (s, 1H), 2.92 (s, 2H), 2.64 (q, J=7.5 Hz, 2H), 2.57 (s, 3H), 2.44 (s, 2H), 1.36 (t, J=7.5 Hz, 3H), 1.15 (s, 6H). $^{13}$C NMR (151 MHz, Chloroform-d) 6193.3, 162.1, 160.8, 150.8, 149.2, 145.4, 142.5, 142.0, 117.9, 114.6 (d, J=4.1 Hz), 112.3, 107.6 (d, J=25.5 Hz), 102.8, 52.3, 37.7, 36.0, 28.4 (2), 26.4, 13.4, 12.0. HRMS (ESI) m/z [M+Na] calculated for $C_{21}H_{22}FN_3O_2Na$, 390.1594 found 390.1609.

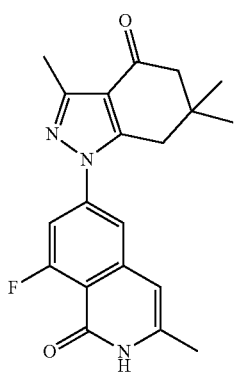 [SMILES: Cc1cc2cc(-n3nc(C)c4c3CC(C)(C)CC4=O)cc(F)c2c(=O)[nH]1]

8-fluoro-3-methyl-6-(3,6,6-trimethyl-4-oxo-4,5,6,7-tetrahydro-1H-indazol-1-yl)isoquinolin-1(2H)-one (3a): 78 mg, Yield 35%; $^1$H NMR (500 MHz, Chloroform-d) δ 10.63 (s, 1H), 7.40-7.35 (m, 1H), 7.29-7.25 (m, 1H), 6.34 (s, 1H), 2.91 (s, 2H), 2.57 (s, 3H), 2.44 (s, 2H), 2.41 (d, J=1.0 Hz, 3H), 1.15 (s, 6H). $^{13}$C NMR (126 MHz, Chloroform-d) δ 193.3, 163.0 (d, J=265.2 Hz), 161.3 (d, J=3.9 Hz), 150.8, 149.2, 142.4, 142.1 (d, J=1.8 Hz), 140.5, 117.8, 114.3 (d, J=4.2 Hz), 112.0 (d, J=6.4 Hz), 107.5 (d, J=25.6 Hz), 103.9 (d, J=2.7 Hz), 52.2, 37.7, 36.0, 28.4 (2), 19.3, 13.4. HRMS (ESI) m/z [M+H] calculated for $C_{20}H_{20}FN_3O_2$, 354.1617, found 354.1626.

8-fluoro-3-isopropyl-6-(3,6,6-trimethyl-4-oxo-4,5,6,7-tetrahydro-1H-indazol-1-yl)isoquinolin-1(2H)-one (3c): 96 mg, Yield: 40%; $^1$H NMR (600 MHz, Chloroform-d) δ 9.31 (s, 1H), 7.41 (d, J=2.0 Hz, 1H), 7.27 (dd, J=11.7, 2.0 Hz, 1H), 6.32 (s, 1H), 2.91 (s, 2H), 2.86-2.79 (m, 1H), 2.57 (s, 3H), 2.44 (s, 2H), 1.36 (d, J=6.9 Hz, 6H), 1.15 (s, 6H). $^{13}$C NMR (151 MHz, Chloroform-d) δ 193.31, 162.99 (d, J=265.3 Hz), 160.6, 150.8, 149.4, 149.2, 142.4 (d, J=11.7 Hz), 142.0, 117.9, 114.8 (d, J=4.3 Hz), 112.4, 107.6 (d, J=25.6 Hz), 100.9 (d, J=2.6 Hz), 52.3, 37.7, 36.0, 32.2, 28.4 (2), 21.2 (2), 13.4. HRMS (ESI) m/z [M+Na] calculated for $C_{22}H_{24}FN_3O_2Na$, 404.1750, found 404.1743.

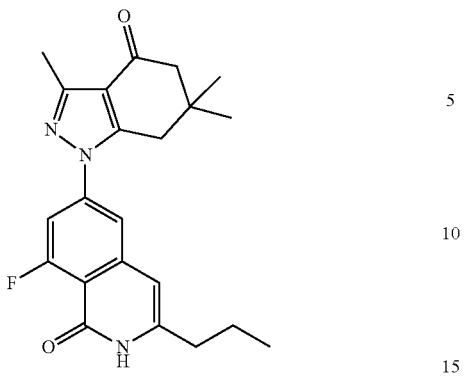

8-fluoro-3-propyl-6-(3,6,6-trimethyl-4-oxo-4,5,6,7-tetrahydro-1H-indazol-1-yl)isoquinolin-1(2H)-one (3d): 113 mg, Yield 45%; $^1$H NMR (500 MHz, Chloroform-d) δ 10.32 (s, 1H), 7.40 (d, J=2.0 Hz, 1H), 7.26 (d, J=14.0 Hz, 1H), 6.37-6.29 (s, 1H), 2.91 (s, 2H), 2.61 (t, J=7.6 Hz, 2H), 2.57 (s, 3H), 2.44 (s, 2H), 1.80 (h, J=7.4 Hz, 2H), 1.15 (s, 6H), 1.04 (t, J=7.4 Hz, 3H). $^{13}$C NMR (126 MHz, Chloroform-d) δ 193.3, 162.9 (d, J=265.2 Hz), 161.1 (d, J=4.5 Hz), 150.8, 149.3, 144.5, 142.8 (d, J=11.9 Hz), 142.0 (d, J=2.4 Hz), 117.8, 114.6 (d, J=4.6 Hz), 112.2 (d, J=7.2 Hz), 107.5 (d, J=25.7 Hz), 103.3 (d, J=3.5 Hz), 52.3, 37.8, 36.0, 35.2, 28.4 (2), 21.4, 13.5, 13.4. HRMS (ESI) m/z [M+Na] calculated for $C_{22}H_{24}FN_3O_2Na$, 404.1750, found 404.1765.

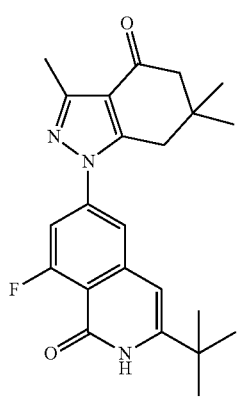 [SMILES: Cc1nn(-c2cc(F)c3c(=O)[nH]c(C(C)(C)C)cc3c2)c2c1C(=O)CC(C)(C)C2]

3-(tert-butyl)-8-fluoro-6-(3,6,6-trimethyl-4-oxo-4,5,6,7-tetrahydro-1H-indazol-1-yl)isoquinolin-1(2H)-one (3f): 95 mg, Yield 38%; $^1$H NMR (600 MHz, Chloroform-d) δ 8.78 (s, 1H), 7.44 (d, J=1.9 Hz, 1H), 7.27 (d, J=0.7 Hz, 1H), 6.37 (s, 1H), 2.91 (s, 2H), 2.56 (S, 3H), 2.44 (s, 2H), 1.38 (S, 9H), 1.15 (s, 6H). $^{13}$C NMR (151 MHz, Chloroform-d) δ 193.3, 161.2 (d, J=254.3 Hz), 155.6, 151.3, 150.8, 149.2, 142.4 (d, J=11.5 Hz) 141.9, 140.8, 117.9, 115.1, 107.7 (d, J=25.8 Hz), 100.3, 52.3, 37.8, 36.0, 34.5, 28.8 (3), 28.4 (2), 13.4. HRMS (ESI) m/z [M+Na] calculated for $C_{23}H_{26}FN_3O_2Na$, 418.1907, found 418.1897.

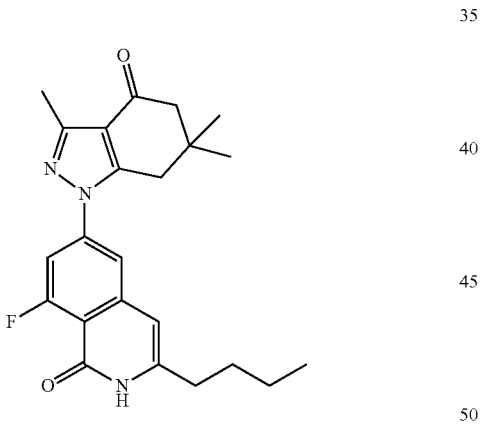

3-butyl-8-fluoro-6-(3,6,6-trimethyl-4-oxo-4,5,6,7-tetrahydro-1H-indazol-1-yl)isoquinolin-1(2H)-one (3e): 100 mg, Yield 40%; $^1$H NMR (600 MHz, Chloroform-d) δ 9.99 (d, J=20.1 Hz, 1H), 7.40 (d, J=1.9 Hz, 1H), 7.25 (dd, J=11.6, 2.0 Hz, 1H), 6.32 (s, 1H), 2.91 (s, 2H), 2.61 (t, J=7.7 Hz, 2H), 2.58-2.55 (m, 3H), 2.44 (s, 2H), 1.73 (p, J=7.7 Hz, 2H), 1.45 (h, J=7.4 Hz, 2H), 1.15 (s, 6H), 1.01-0.95 (m, 3H). $^{13}$C NMR (151 MHz, Chloroform-d) δ 193.3, 163.0 (d, J=265.5 Hz), 161.1 (d, J=3.6 Hz), 150.8, 149.2, 144.6, 142.4 (d, J=11.5 Hz), 142.1, 117.9, 114.6 (d, J=4.1 Hz), 112.3 (d, J=6.3 Hz), 107.5 (d, J=25.5 Hz), 103.2 (d, J=2.6 Hz), 52.3, 37.8, 36.0, 33.1, 30.1, 28.4 (2), 22.1, 13.7, 13.4. HRMS (ESI) m/z [M+Na] calculated for $C_{23}H_{26}FN_3O_2Na$, 418.1907, found 418.1902.

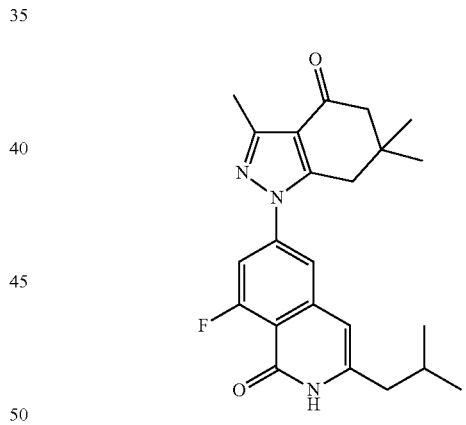

8-fluoro-3-isobutyl-6-(3,6,6-trimethyl-4-oxo-4,5,6,7-tetrahydro-1H-indazol-1-yl)isoquinolin-1(2H)-one (3g): 88 mg, Yield 35%; $^1$H NMR (600 MHz, Chloroform-d) δ 8.74 (s, 1H), 7.43 (d, J=2.0 Hz, 1H), 7.24 (dd, J=11.7, 2.0 Hz, 1H), 6.28 (s, 1H), 2.91 (s, 2H), 2.56 (s, 3H), 2.44 (s, 2H), 2.41 (d, J=7.4 Hz, 2H), 1.15 (s, 6H), 1.02 (d, J=6.6 Hz, 6H). $^{13}$C NMR (151 MHz, Chloroform-d) δ 197.0, 171.0, 161.3 (d, J=3.9 Hz), 150.8, 149.2, 148.7, 142.5 (d, J=11.7 Hz), 142.1 (d, J=1.8 Hz), 139.2, 122.4, 114.3 (d, J=4.2 Hz), 112.0 (d, J=6.4 Hz), 107.5 (d, J=25.6 Hz), 103.9 (d, J=2.7 Hz), 53.4, 42.8, 37.7, 36.0, 28.4, 22.2 (2), 14.2 (2). HRMS (ESI) m/z [M+Na] calculated for $C_{23}H_{26}FN_3O_2Na$, 418.1907, found 418.1913.

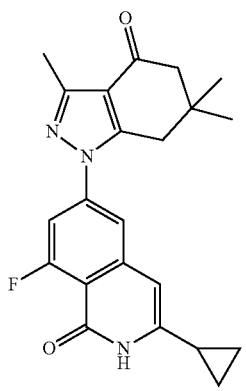 [SMILES: Cc1nn(-c2cc(F)c3c(=O)[nH]c(C4CC4)cc3c2)c2c1C(=O)CC(C)(C)C2]

3-cyclopropyl-8-fluoro-6-(3,6,6-trimethyl-4-oxo-4,5,6,7-tetrahydro-1H-indazol-1-yl)isoquinolin-1(2H)-one (3h): 80 mg, Yield 33%; $^1$H NMR (600 MHz, Chloroform-d) δ 9.43 (s, 1H), 7.38-7.35 (m, 1H), 7.23 (dd, J=11.8, 2.0 Hz, 1H), 6.24-6.20 (m, 1H), 2.90 (s, 2H), 2.56 (s, 3H), 2.43 (s, 2H), 1.90-1.83 (m, 1H), 1.14 (s, 6H), 1.10-1.08 (m, 2H), 0.93-0.90 (m, 2H). $^{13}$C NMR (151 MHz, Chloroform-d) δ 193.3, 163.0 (d, J=265.1 Hz), 160.6, 150.8, 149.2, 145.7, 142.5, 142.0, 117.9, 114.4 (d, J=4.2 Hz), 112.2 (d, J=6.3 Hz), 107.4 (d, J=25.5 Hz), 101.1 (d, J=2.7 Hz), 52.3, 37.8, 35.9, 28.4 (2), 13.5, 13.4, 7.4 (2). HRMS (ESI) m/z [M+Na] calculated for $C_{22}H_{22}FN_3O_2Na$, 402.1594, found 402.1603.

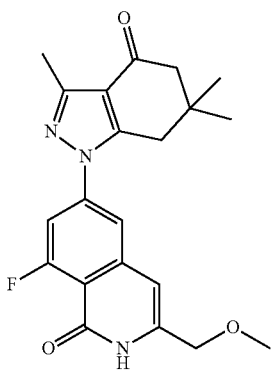 [SMILES: COCc1cc2cc(-n3nc(C)c4c3CC(C)(C)CC4=O)cc(F)c2c(=O)[nH]1]

8-fluoro-3-(methoxymethyl)-6-(3,6,6-trimethyl-4-oxo-4,5,6,7-tetrahydro-1H-indazol-1-yl)isoquinolin-1(2H)-one (3i): 80 mg, Yield 33%; $^1$H NMR (600 MHz, Chloroform-d) δ 8.74 (s, 1H), 7.38 (d, J=2.0 Hz, 1H), 7.22 (dd, J=11.7, 2.0 Hz, 1H), 6.30 (s, 1H), 4.30 (s, 2H), 3.39 (s, 3H), 2.83 (s, 2H), 2.49 (s, 3H), 2.36 (s, 2H), 1.07 (s, 6H). $^{13}$C NMR (126 MHz, Chloroform-d) δ 193.2, 162.9 (d, J=265.1 Hz), 159.7, 150.9, 149.2, 142.6, 141.2 (d, J=2.2 Hz), 139.5, 117.9, 114.9 (d, J=4.6 Hz), 113.3 (d, J=6.2 Hz), 108.2 (d, J=25.7 Hz), 102.6 (d, J=3.3 Hz), 70.0, 58.7, 52.2 37.8, 35.9, 28.4 (2), 13.4. HRMS (ESI) m/z [M+H] calculated for $C_{21}H_{23}FN_3O_3$, 384.1723, found 384.1716.

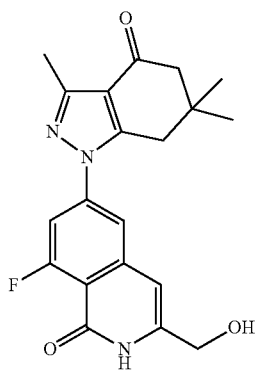 [SMILES: Cc1nn(-c2cc(F)c3c(=O)[nH]c(CO)cc3c2)c2c1C(=O)CC(C)(C)C2]

8-fluoro-3-(hydroxymethyl)-6-(3,6,6-trimethyl-4-oxo-4,5,6,7-tetrahydro-1H-indazol-1-yl)isoquinolin-1(2H)-one (3j): To a solution of 8-fluoro-3-(methoxymethyl)-6-(3,6,6-trimethyl-4-oxo-4,5,6,7-tetrahydro-1H-indazol-1-yl)isoquinolin-1(2H)-one (3i) (100 mg, 0.26 mmol, 1 eq) in 3 mL DCM cooled to 0° C. was added 0.8 mL of 1M BBr$_3$ solution in DCM (0.78 mmol, 3 eq) dropwise, the reaction completion was monitored using TLC. After 2 h, the reaction was quenched dropwise using 2 mL saturated sodium bicarbonate solution, resulting biphasic mixture was extracted using ethyl acetate (10 mL×2). The organic fractions were collected, washed with water and dried over sodium sulfate. Organic fraction was adsorbed onto silica for column chromatography purification using (4:6 ethyl acetate/hexanes) to furnish 55 mg (0.155 mmol, Yield 60%) of 8-fluoro-3-(hydroxymethyl)-6-(3,6,6-trimethyl-4-oxo-4,5,6,7-tetrahydro-1H-indazol-1-yl)isoquinolin-1(2H)-one (3j) as white solid. $^1$H NMR (600 MHz, Chloroform-d) δ 10.28 (s, 1H), 7.35 (d, J=1.9 Hz, 1H), 7.24 (dd, J=11.8, 2.0 Hz, 1H), 6.36 (s, 1H), 4.59 (s, 2H), 2.83 (s, 2H), 2.49 (s, 3H), 2.36 (s, 2H), 1.07 (s, 6H). $^{13}$C NMR (126 MHz, Chloroform-d) δ 193.25, 166.29 (d, J=265.1 Hz) 151.0, 149.3, 142.3, 141.4, 118.0, 114.9 (d, J=4.6 Hz), 112.7, 108.2 (d, J=25.4 Hz), 102.7 (d, J=2.9 Hz), 100.8, 99.9, 61.1, 52.2, 37.7, 35.9, 28.4(2), 13.4. HRMS (ESI) m/z [M+H] calculated for $C_{20}H_{21}FN_3O_3$, 370.1567, found 370.1581.

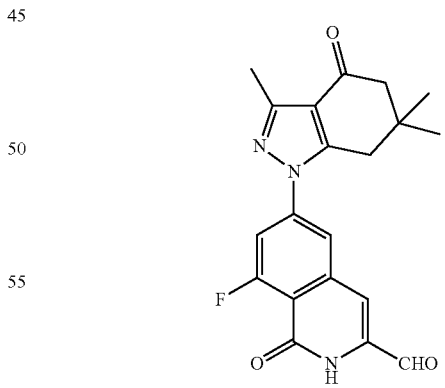

8-fluoro-1-oxo-6-(3,6,6-trimethyl-4-oxo-4,5,6,7-tetrahydro-1H-indazol-1-yl)-1,2-dihydroisoquinoline-3-carbaldehyde (3k): To a solution of 3j (30 mg, 0.081 mmol, 1 eq) in 3 mL DCM in a 15 mL sealed reaction vessel, was added activated MnO$_2$ (70 mg, 0.81 mmol, 10 eq). The reaction vessel was sealed and heated to 45° C. for 6 h. Upon completion, the reaction mixture was cooled, filtered through a plug of celite, and a quick flash column chromatography (5:5 ethyl acetate/hexanes) afforded 8-fluoro-1-oxo-6-(3,6,6-trimethyl-4-oxo-4,5,6,7-tetrahydro-1H-indazol-1-yl)-1,2-dihydroisoquinoline-3-carbaldehyde (3k) (28 mg, 0.076 mmol, 94%) as white solid. $^1$H NMR (500 MHz, Chloroform-d) δ 9.63 (s, 1H), 8.91 (s, 1H), 7.77 (s, 1H), 7.53 (dd, J=11.6, 2.0 Hz, 1H), 7.14 (d, J=1.7 Hz, 1H), 2.96 (s, 2H), 2.58 (s, 3H), 2.46 (s, 2H), 1.17 (s, 6H). $^{13}$C NMR (126 MHz, Chloroform-d) δ 193.1, 183.6, 161.3 (d, J=265.2 Hz), 151.4, 143.1, 149.3, 139.1, 136.3, 124.1, 118.4, 117.2 (d, J=4.8 Hz), 116.2 (d, J=6.2 Hz), 116.0 (d, J=3.7 Hz), 111.5 (d, J=26.0 Hz), 52.2, 37.9, 36.0, 28.5 (2), 13.4. HRMS (ESI) m/z [M+H] calculated for $C_{20}H_{24}NO_3$, 326.1756, found 326.1781.

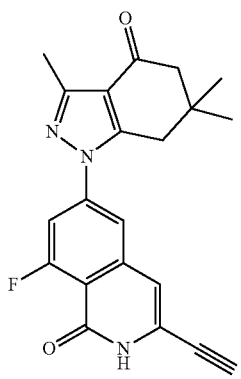 [SMILES: C#Cc1cc2cc(-n3nc(C)c4c3CC(C)(C)CC4=O)cc(F)c2c(=O)[nH]1]

3-ethynyl-8-fluoro-6-(3,6,6-trimethyl-4-oxo-4,5,6,7-tetrahydro-1H-indazol-1-yl)isoquinolin-1(2H)-one (3l): Dimethyl-1-diazo-2-oxopropylphosphonate (60 μL, 0.40 mmol, 1.2 eq.) was added to a stirred solution of aldehyde 3k (50 mg, 0.13 mmol, 1.0 eq.) and potassium carbonate (36 mg, 0.26 mmol, 2.0 eq) in 3 mL methanol. The resulting mixture was stirred for 24 h at rt. Subsequently, methanol was evaporated in vacuo and remaining mass was diluted with water and ethyl acetate 10 mL each. The organic layer was washed with saturated sodium bicarbonate solution (10 mL), dried over anhydrous sodium sulfate, filtered and concentrated. The residue was purified by flash chromatography (SiO2, 1:3 ethyl acetate/hexanes) to afford 3-ethynyl-8-fluoro-6-(3,6,6-trimethyl-4-oxo-4,5,6,7-tetrahydro-1H-indazol-1-yl)isoquinolin-1(2H)-one (3l) (40 mg, 0.11 mmol, 85%). $^1$H NMR (400 MHz, Chloroform-d) 68.97 (s, 1H), 7.48 (s, 1H), 7.38 (dd, J=11.7, 1.7 Hz, 1H), 6.78 (d, J=1.8 Hz, 1H), 3.41 (s, 1H), 2.92 (s, 2H), 2.57 (s, 3H), 2.45 (s, 2H), 1.15 (s, 6H). $^{13}$C NMR (101 MHz, Chloroform-d) δ 193.2, 159.1, 151.1, 149.2, 142.9, 140.4, 135.9, 135.1, 123.5, 118.1, 115.2, 111.3, 109.4 (d, J=25.9 Hz), 82.7, 52.2, 37.8, 36.0, 29.7, 28.5 (2), 13.4. HRMS (ESI) m/z [M+H] calculated for $C_{21}H_{26}NO_3$, 340.1912, found 340.1916.

General procedure for preparation of 4a-k and 5a-g: A solution of the desired intermediate 3a-l (0.07 mmol, 1 eq) in 1 mL DMSO was taken in a 5 mL sealed reaction vessel, the corresponding amine (trans-4-aminocyclohexanol for 4a-k) (0.212 mmol, 3 eq) then diisopropylethylamine (DIPEA)(0.212 mmol, 3 eq) was introduced. The reaction vessel was then sealed and heated to 140° C. for 12 h, cooled and water (25 mL) was added. The aqueous layer was extracted with ethyl acetate (25 mL×3), the organic fractions were combined and washed with brine (25 mL) and dried over sodium sulfate. Purification with column chromatography (SiO2, 4:96 methanol:DCM for 4a-k, 5a, 5b, 5e and 5:1:94 methanol:7M NH3 in methanol:DCM for 5c, 5d, 5f, 5g) resulted in the desired products which were further purified by preparative TLC to give the desired compounds 4a-k, 5a-g as light yellow solids.

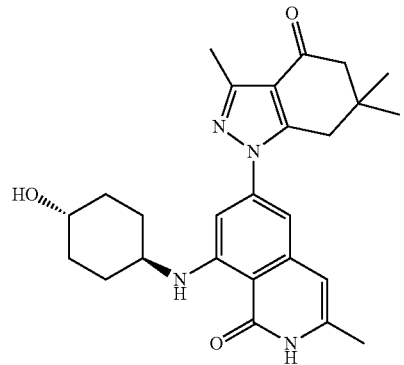 [SMILES: Cc1cc2cc(-n3nc(C)c4c3CC(C)(C)CC4=O)cc(N[C@H]3CC[C@H](O)CC3)c2c(=O)[nH]1]

8-(((1r,4r)-4-hydroxycyclohexyl)amino)-3-methyl-6-(3,6,6-trimethyl-4-oxo-4,5,6,7-tetrahydro-1H-indazol-1-yl)isoquinolin-1(2H)-one (4a): 22 mg, Yield 70%; $^1$H NMR (400 MHz, Chloroform-d) δ 9.16 (d, J=7.5 Hz, 1H), 9.05 (s, 1H), 6.51-6.40 (m, 2H), 6.09 (s, 1H), 3.74-3.59 (m, 2H), 3.31 (d, J=24.2 Hz, 1H), 2.78 (s, 2H), 2.49 (s, 3H), 2.34 (s, 2H), 2.19 (s, 3H), 2.17-2.08 (m, 2H), 2.04-1.95 (m, 2H), 1.38 (q, J=11.1, 9.9 Hz, 4H), 1.04 (s, 6H). $^{13}$C NMR (101 MHz, CDCl3) δ 193.4, 185.3, 169.7, 165.5, 151.4, 150.0, 149.1, 143.5, 143.2, 142.1, 137.4, 107.3, 105.7, 104.8, 100.3, 69.7, 52.4, 50.2, 37.8, 35.8, 33.5, 29.9, 28.4 (2), 19.0, 13.4. HRMS (ESI) m/z [M+H] calculated for $C_{26}H_{33}N_4O_3$, 449.2553, found 449.2566.

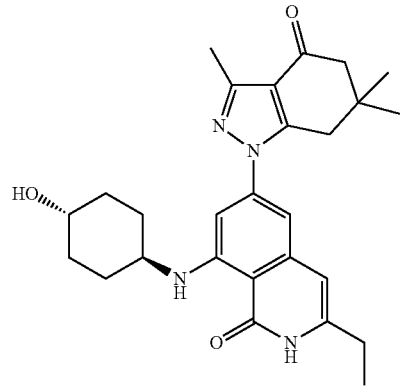 [SMILES: CCc1cc2cc(-n3nc(C)c4c3CC(C)(C)CC4=O)cc(N[C@H]3CC[C@H](O)CC3)c2c(=O)[nH]1]

3-ethyl-8-(((1r,4r)-4-hydroxycyclohexyl)amino)-6-(3,6,6-trimethyl-4-oxo-4,5,6,7-tetrahydro-1H-indazol-1-yl)isoquinolin-1(2H)-one (4b): 19 mg, Yield 58%; $^1$H NMR (500 MHz, Chloroform-d) δ 9.77 (s, 1H), 9.45 (s, 1H), 6.67 (d, J=28.0 Hz, 2H), 6.26-6.16 (m, 1H), 3.77 (dd, J=8.7, 4.4 Hz, 1H), 3.44 (s, 1H), 2.89 (s, 2H), 2.62-2.55 (m, 5H), 2.43 (s, 2H), 2.30-2.17 (m, 2H), 2.10 (d, J=10.4 Hz, 3H), 1.54-1.42 (m, 4H), 1.32 (q, J=7.6 Hz, 3H), 1.14 (s, 6H). $^{13}$C NMR (126 MHz, CDCl3) δ 193.4, 165.6, 150.9, 150.1, 149.5, 149.1, 143.4, 143.1, 142.1, 119.4, 117.3, 104.3, 99.9, 88.4, 69.6, 52.4, 37.8, 35.8 (2), 33.5 (2), 29.7, 29.7, 28.4 (2), 26.1, 13.5, 12.4. HRMS (ESI) m/z [M+H] calculated for $C_{28}H_{38}N_5O_2$, 476.3026, found 476.3049.

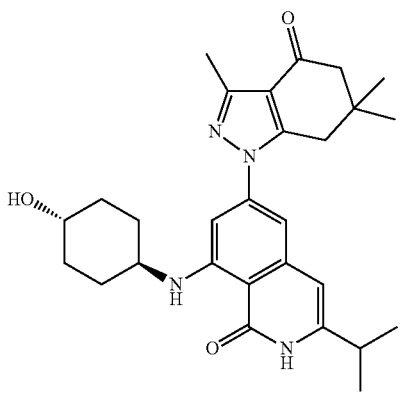 [SMILES: Cc1nn(-c2cc(N[C@H]3CC[C@H](O)CC3)c3c(=O)[nH]c(C(C)C)cc3c2)c2c1C(=O)CC(C)(C)C2]

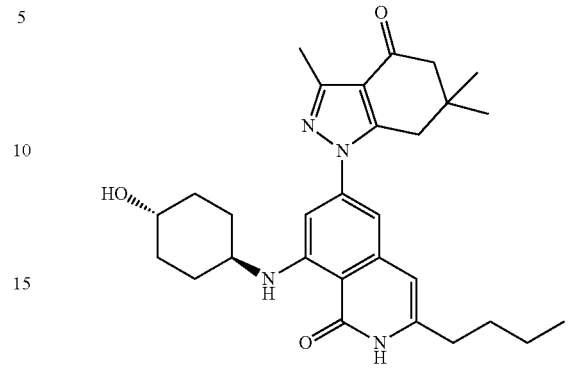

13.5, 13.5. HRMS (ESI) m/z [M+Na] calculated for $C_{28}H_{36}N_4O_3Na$, 499.2685, found 499.2688.

8-(((1r,4r)-4-hydroxycyclohexyl)amino)-3-isopropyl-6-(3,6,6-trimethyl-4-oxo-4,5,6,7-tetrahydro-1H-indazol-1-yl)isoquinolin-1(2H)-one (4c): 21 mg, Yield 65%; $^1$H NMR (500 MHz, Chloroform-d) δ 11.01-10.60 (m, 1H), 9.29 (d, J=7.4 Hz, 1H), 6.59 (d, J=2.0 Hz, 1H), 6.52 (d, J=1.9 Hz, 1H), 6.21 (d, J=1.8 Hz, 1H), 3.79-3.70 (m, 1H), 3.47-3.38 (m, 1H), 2.88-2.77 (m, 3H), 2.56 (s, 3H), 2.41 (s, 2H), 2.25-2.18 (m, 2H), 2.10-2.04 (m, 2H), 1.52-1.38 (m, 4H), 1.34 (d, J=6.9 Hz, 6H), 1.11 (s, 6H). $^{13}$C NMR (126 MHz, Chloroform-d) δ 193.6, 166.8-165.9 (m), 151.3 (d, J=15.4 Hz), 149.9, 149.2, 147.6 (d, J=17.2 Hz), 143.1, 142.2, 117.1, 107.6 (d, J=2.7 Hz), 105.1 (d, J=2.7 Hz), 102.9 (t, J=2.6 Hz), 100.1, 69.7, 52.4, 50.1 (d, J=11.0 Hz), 37.7, 35.9, 33.6 (2), 31.9 (d, J=6.7 Hz), 30.2 (2), 28.4 (2), 21.4 (2), 13.48. HRMS (ESI) m/z [M+Na] calculated for $C_{28}H_{37}N_4O_3Na$, 499.2685, found 499.2672.

3-butyl-8-(((1r,4r)-4-hydroxycyclohexyl)amino)-6-(3,6,6-trimethyl-4-oxo-4,5,6,7-tetrahydro-1H-indazol-1-yl)isoquinolin-1(2H)-one (4e): 20 mg, Yield 58%; $^1$H NMR (500 MHz, Chloroform-d) δ 10.21 (s, 1H), 9.27 (d, J=7.5 Hz, 1H), 6.55 (dd, J=39.0, 1.9 Hz, 2H), 6.20 (d, J=2.0 Hz, 1H), 3.79-3.72 (m, 1H), 3.47-3.37 (m, 1H), 2.87 (s, 2H), 2.60-2.52 (m, 5H), 2.42 (s, 2H), 2.26-2.19 (m, 2H), 2.11-2.05 (m, 2H), 1.74-1.64 (m, 2H), 1.54-1.32 (m, 6H), 1.12 (s, 6H), 0.96 (t, J=7.3 Hz, 3H). $^{13}$C NMR (126 MHz, Chloroform-d) δ 193.5, 166.1, 151.4, 149.9, 149.1, 143.1, 142.2, 142.1, 117.2, 107.5, 105.2, 104.9, 100.1, 69.8, 52.4, 50.2, 37.7, 35.8, 33.7 (2), 32.6, 30.1 (2), 30.0, 28.4 (2), 22.1, 13.9, 13.5. HRMS (ESI) m/z [M+H] calculated for $C_{29}H_{39}N_4O_3$, 491.3022, found 491.3011.

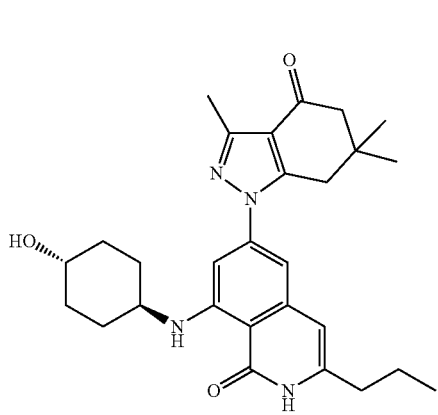 [SMILES: CCCc1cc2cc(-n3nc(C)c4c3CC(C)(C)CC4=O)cc(N[C@H]3CC[C@H](O)CC3)c2c(=O)[nH]1]

8-(((1r,4r)-4-hydroxycyclohexyl)amino)-3-propyl-6-(3,6,6-trimethyl-4-oxo-4,5,6,7-tetrahydro-1H-indazol-1-yl)isoquinolin-1(2H)-one (4d): 22 mg, Yield 65%; $^1$H NMR (500 MHz, Chloroform-d) δ 10.44 (s, 1H), 9.29 (d, J=7.4 Hz, 1H), 6.56 (dd, J=41.9, 1.9 Hz, 2H), 6.21 (d, J=1.9 Hz, 1H), 3.80-3.73 (m, 1H), 3.47-3.38 (m, 1H), 2.87 (s, 2H), 2.58 (s, 3H), 2.54 (t, J=7.5 Hz, 2H), 2.43 (s, 2H), 2.28-2.20 (m, 2H), 2.12-2.03 (m, 2H), 1.76 (h, J=7.4 Hz, 2H), 1.55-1.36 (m, 4H), 1.13 (s, 6H), 1.01 (t, J=7.3 Hz, 3H). $^{13}$C NMR (126 MHz, Chloroform-d) δ 193.5, 166.3, 151.4, 149.9, 149.1, 143.1, 142.2, 141.9, 117.2, 107.5, 105.4, 104.9, 100.0, 69.8, 52.4, 50.2, 37.7, 35.9, 34.8, 33.6 (2), 30.1 (2), 28.4 (2), 21.3, 3-(tert-butyl)-8-(((1r,4r)-4-hydroxycyclohexyl)amino)-6-(3,6,6-trimethyl-4-oxo-4,5,6,7-tetrahydro-1H-indazol-1-yl)isoquinolin-1(2H)-one (4f): 22 mg, Yield 65%; $^1$H NMR (500 MHz, Chloroform-d) δ 9.53 (s, 1H), 9.28 (d, J=6.9 Hz, 1H), 6.68-6.51 (m, 2H), 6.27 (d, J=2.1 Hz, 1H), 3.80-3.73 (m, 1H), 3.47-3.43 (m, 1H), 2.88 (s, 2H), 2.58 (s, 3H), 2.43 (s, 2H), 2.25-2.18 (m, 2H), 2.13-2.06 (m, 2H), 1.53-1.40 (m, 4H), 1.38 (s, 9H), 1.13 (s, 6H). $^{13}$C NMR (126 MHz, Chloroform-d) δ 193.5, 165.7, 150.9, 150.0, 149.3, 149.1, 143.2, 141.9, 117.2, 107.6, 105.8, 102.3, 100.7, 69.8, 52.4, 50.6, 37.8, 35.9, 34.3, 33.7 (2), 30.1 (2), 28.9 (3), 28.4 (2), 13.5. HRMS (ESI) m/z [M+Na] calculated for $C_{29}H_{38}N_4O_3Na$, 513.2842, found 513.2821.

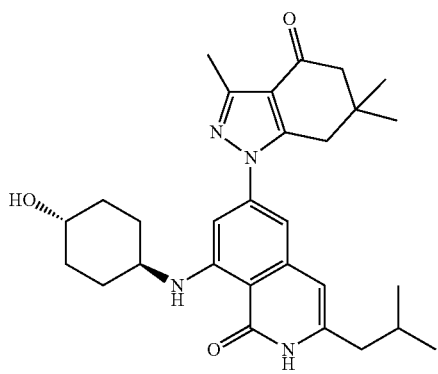 [SMILES: Cc1nn(-c2cc(N[C@H]3CC[C@H](O)CC3)c3c(=O)[nH]c(CC(C)C)cc3c2)c2c1C(=O)CC(C)(C)C2]

8-(((1r,4r)-4-hydroxycyclohexyl)amino)-3-isobutyl-6-(3,6,6-trimethyl-4-oxo-4,5,6,7-tetrahydro-1H-indazol-1-yl)isoquinolin-1(2H)-one (4g): 19 mg, Yield 55%; $^1$H NMR (500 MHz, Chloroform-d) δ 9.57 (s, 1H), 9.24 (d, J=7.5 Hz, 1H), 6.60 (d, J=1.9 Hz, 1H), 6.50 (d, J=1.9 Hz, 1H), 6.17 (d, J=2.0 Hz, 1H), 3.80-3.72 (m, 1H), 3.46-3.37 (m, 1H), 2.87 (s, 2H), 2.63 (s, 4H), 2.42 (s, 2H), 2.39 (d, J=7.4 Hz, 2H), 2.23 (dd, J=9.4, 5.0 Hz, 2H), 2.11-1.97 (m, 3H), 1.53-1.39 (m, 4H), 1.12 (s, 6H), 0.99 (d, J=6.6 Hz, 6H). $^{13}$C NMR (126 MHz, Chloroform-d) δ 193.5, 165.9, 151.4, 150.0, 149.1, 143.1, 142.0, 141.0, 117.2, 107.5, 106.1, 105.0, 100.1, 69.8, 52.4, 50.3, 42.4, 37.7, 35.8, 33.7 (2), 30.1 (2), 28.4, 27.9 (2), 22.3 (2), 13.5. HRMS (ESI) m/z [M+H] calculated for $C_{29}H_{39}N_4O_3$, 491.3022, found 491.3019.

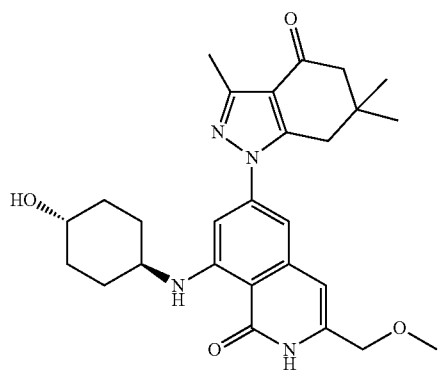

8-(((1r,4r)-4-hydroxycyclohexyl)amino)-3-(methoxymethyl)-6-(3,6,6-trimethyl-4-oxo-4,5,6,7-tetrahydro-1H-indazol-1-yl)isoquinolin-1(2H)-one (4i): 20 mg, Yield 60%; $^1$H NMR (400 MHz, Chloroform-d) δ 9.27 (d, J=7.5 Hz, 1H), 8.63 (s, 1H), 6.62 (d, J=1.8 Hz, 1H), 6.56 (s, 1H), 6.25 (s, 1H), 4.32 (s, 2H), 3.42 (s, 3H), 2.86 (s, 2H), 2.57 (s, 3H), 2.42 (s, 2H), 2.21 (s, 2H), 2.07 (s, 2H), 1.49 (q, J=11.9, 10.3 Hz, 4H), 1.12 (s, 6H). $^{13}$C NMR (101 MHz, CDCl$_3$) δ 193.3, 164.9, 151.5, 150.0, 149.0, 143.2, 141.2, 137.1, 117.3, 108.4, 105.3, 105.1, 101.0, 70.2, 69.7, 58.4, 52.4, 50.3, 37.8, 35.8, 33.5 (2), 29.9 (2), 28.4 (2), 13.4. HRMS (ESI) m/z [M+H] calculated for $C_{27}H_{35}N_4O_4$, 479.2658, found 479.2665.

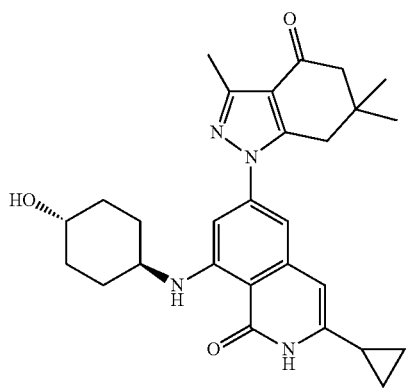 [SMILES: Cc1nn(-c2cc(N[C@H]3CC[C@H](O)CC3)c3c(=O)[nH]c(C4CC4)cc3c2)c2c1C(=O)CC(C)(C)C2]

3-cyclopropyl-8-(((1r,4r)-4-hydroxycyclohexyl)amino)-6-(3,6,6-trimethyl-4-oxo-4,5,6,7-tetrahydro-1H-indazol-1-yl)isoquinolin-1(2H)-one (4h): 22 mg, Yield 66%; $^1$H NMR (500 MHz, Chloroform-d) δ 9.67 (s, 1H), 9.26 (d, J=7.2 Hz, 1H), 6.58 (d, J=1.9 Hz, 1H), 6.53 (d, J=2.0 Hz, 1H), 6.15 (d, J=1.9 Hz, 1H), 3.80-3.73 (m, 1H), 3.48-3.39 (m, 1H), 2.88 (s, 2H), 2.59 (s, 3H), 2.44 (s, 2H), 2.26-2.18 (m, 2H), 2.12-2.04 (m, 2H), 1.87-1.78 (m, 1H), 1.55-1.38 (m, 4H), 1.14 (s, 6H), 1.04-0.99 (m, 2H), 0.95-0.90 (m, 2H). $^{13}$C NMR (126 MHz, Chloroform-d) δ 193.5, 165.7, 150.0, 149.1, 143.2, 143.2, 142.0, 117.2, 107.5, 105.0, 103.4, 100.2, 69.8, 52.4, 50.3, 37.7, 35.8, 33.7 (2), 30.0 (2), 28.4 (2), 13.5, 13.4, 7.1 (2). HRMS (ESI) m/z [M+H] calculated for $C_{28}H_{35}N_4O_3$, 475.2709, found 475.2698.

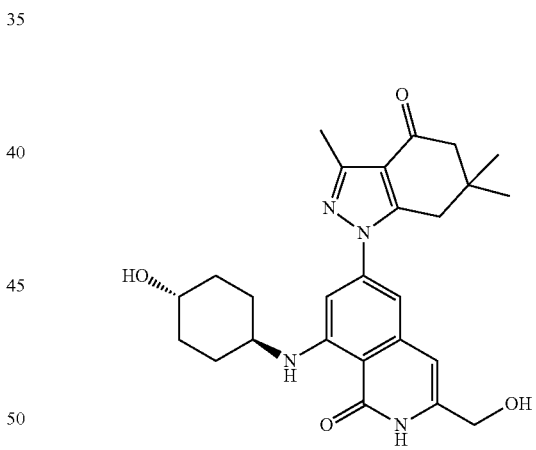

8-(((1r,4r)-4-hydroxycyclohexyl)amino)-3-(hydroxymethyl)-6-(3,6,6-trimethyl-4-oxo-4,5,6,7-tetrahydro-1H-indazol-1-yl)isoquinolin-1(2H)-one (4j): 20 mg, Yield 63%; $^1$H NMR (400 MHz, Chloroform-d) δ 9.31 (s, 1H), 9.19 (d, J=7.4 Hz, 1H), 6.53 (dd, J=16.9, 1.8 Hz, 2H), 6.22 (s, 1H), 4.49 (s, 2H), 3.79-3.64 (m, 1H), 3.40 (d, J=16.0 Hz, 1H), 2.83 (s, 2H), 2.55 (s, 3H), 2.40 (s, 2H), 2.19 (d, J=11.2 Hz, 2H), 2.09-2.00 (m, 2H), 1.44 (dd, J=18.9, 9.5 Hz, 4H), 1.10 (s, 6H). $^{13}$C NMR (101 MHz, CDCl$_3$) δ 193.6, 172.2, 151.4, 150.1, 149.3, 143.1, 141.5, 139.9, 117.2, 108.2, 105.4, 103.9, 100.8, 69.5, 60.7, 52.3, 50.2, 37.7, 35.8, 33.4 (2), 29.9 (2), 28.3 (2), 13.3. HRMS (ESI) m/z [M+H] calculated for $C_{26}H_{33}N_4O_4$, 465.2502, found 465.2501.

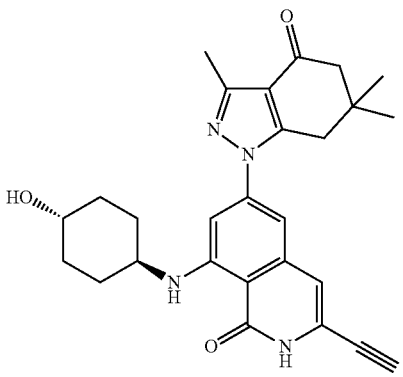 [SMILES: C#Cc1cc2cc(-n3nc(C)c4c3CC(C)(C)CC4=O)cc(N[C@H]3CC[C@H](O)CC3)c2c(=O)[nH]1]

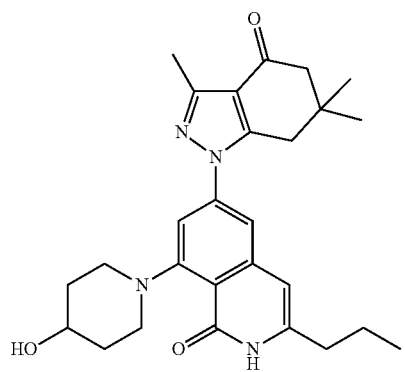

3-ethynyl-8-(((1r,4r)-4-hydroxycyclohexyl)amino)-6-(3,6,6-trimethyl-4-oxo-4,5,6,7-tetrahydro-1H-indazol-1-yl)isoquinolin-1(2H)-one (4k): 11 mg, Yield 35%; $^1$H NMR (400 MHz, Chloroform-d) δ 9.09 (d, J=7.2 Hz, 1H), 8.06 (s, 1H), 6.57-6.52 (m, 3H), 3.69 (s, 2H), 3.31 (d, J=22.1 Hz, 2H), 3.23 (s, 1H), 2.78 (s, 2H), 2.49 (s, 3H), 2.35 (s, 2H), 2.13 (s, 2H), 1.98 (s, 2H), 1.39 (d, J=4.7 Hz, 4H), 1.05 (s, 6H). $^{13}$C NMR (101 MHz, CDCl$_3$) δ 199.1, 167.6, 167.3, 157.5, 153.7, 152.0, 148.1, 132.0, 131.3, 126.4, 121.3, 107.4, 97.5, 77.2, 76.8, 72.7, 52.5, 48.7, 42.8, 36.5, 36.2, 34.3 (2), 31.2 (2), 23.5 (2). HRMS (ESI) m/z [M+H] calculated for C$_{27}$H$_{31}$N$_4$O$_3$, 459.2396, found 459.2375.

8-(4-hydroxypiperidin-1-yl)-3-propyl-6-(3,6,6-trimethyl-4-oxo-4,5,6,7-tetrahydro-1Hindazol-1-yl)isoquinolin-1(2H)-one (5b): 18 mg, Yield 55%; $^1$H NMR (500 MHz, Chloroform-d) δ 9.03 (s, 1H), 6.98 (d, J=3.3 Hz, 2H), 6.15 (s, 1H), 3.86 (s, 1H), 3.41 (s, 2H), 2.87 (s, 2H), 2.78 (s, 2H), 2.52-2.44 (m, 5H), 2.35 (s, 2H), 2.12-2.03 (m, 2H), 1.92-1.81 (m, 2H), 1.67 (h, J=7.4 Hz, 2H), 1.05 (s, 6H), 0.95 (t, J=7.4 Hz, 3H). $^{13}$C NMR (126 MHz, CDCl$_3$) δ 193.5, 162.0, 155.8, 150.3, 149.1, 142.9, 142.4, 141.8, 117.4, 115.5, 112.4, 110.1, 104.2, 53.4, 52.4 (2), 37.6, 35.9, 34.9 (2), 30.9, 29.7, 28.4 (2), 21.1, 13.5, 13.5. HRMS (ESI) m/z [M+H] calculated for C$_{27}$H$_{35}$N$_4$O$_3$, 463.2709, found 463.2710.

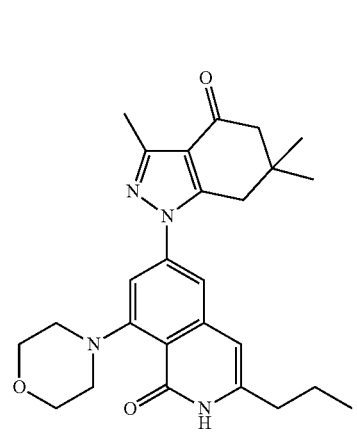 [SMILES: CCCc1cc2cc(-n3nc(C)c4c3CC(C)(C)CC4=O)cc(N3CCOCC3)c2c(=O)[nH]1]

8-morpholino-3-propyl-6-(3,6,6-trimethyl-4-oxo-4,5,6,7-tetrahydro-1H-indazol-1-yl)isoquinolin-1(2H)-one (5a): 20 mg, Yield 65%; $^1$H NMR (400 MHz, Chloroform-d) δ 9.53 (s, 1H), 7.07 (dd, J=18.7, 1.9 Hz, 2H), 6.25 (s, 1H), 4.00 (t, J=4.5 Hz, 4H), 3.22 (s, 4H), 2.86 (s, 2H), 2.57 (s, 5H), 2.43 (s, 2H), 1.76 (h, J=7.4 Hz, 2H), 1.12 (s, 6H), 1.03 (t, J=7.3 Hz, 3H). $^{13}$C NMR (126 MHz, CDCl$_3$) δ 193.4, 162.1, 155.4, 150.4, 149.1, 143.1, 142.8, 141.9, 117.5, 115.4, 112.9, 109.7, 104.3, 67.2 (2), 53.4 (2), 52.4, 37.6, 35.9, 34.8, 28.4 (2), 21.2, 13.5, 13.5. HRMS (ESI) m/z [M+H] calculated for C$_{26}$H$_{33}$N$_4$O$_3$, 449.2553, found 449.2557.

8-(4-methylpiperazin-1-yl)-3-propyl-6-(3,6,6-trimethyl-4-oxo-4,5,6,7-tetrahydro-1Hindazol-1-yl)isoquinolin-1(2H)-one (5c): 18 mg, Yield 55%; $^1$H NMR (400 MHz, Chloroform-d) δ 9.56 (s, 1H), 9.35 (d, J=7.3 Hz, 1H), 6.55 (dd, J=26.8, 2.0 Hz, 2H), 6.19 (d, J=1.9 Hz, 1H), 2.87 (s, 2H), 2.80 (s, 1H), 2.57 (s, 3H), 2.52 (t, J=7.4 Hz, 2H), 2.43 (s, 2H), 2.33 (s, 3H), 2.26 (t, J=10.5 Hz, 2H), 2.16-2.08 (m, 2H), 1.79-1.58 (m, 7H), 1.13 (s, 6H), 1.01 (t, J=7.4 Hz, 3H). $^{13}$C NMR (101 MHz, CDCl$_3$) δ193.5, 165.8, 151.2, 149.9, 149.0, 143.1, 142.1, 141.6, 140.8, 107.7, 105.3, 105.0, 100.2, 52.4, 46.3, 37.7, 35.8, 34.9 (2), 32.1, 31.6, 31.4, 28.4 (2), 21.2 (2), 13.5, 13.4. HRMS (ESI) m/z [M+Na] calculated for C$_{28}$H$_{37}$N$_5$O$_2$Na, 498.2845, found 498.2823.

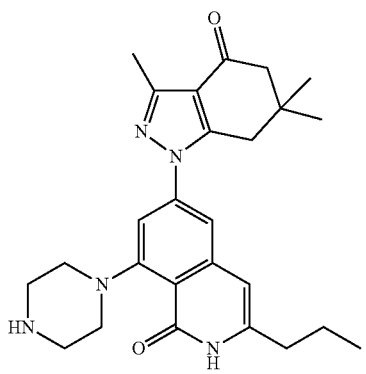 [SMILES: CCCc1cc2cc(-n3nc(C)c4c3CC(C)(C)CC4=O)cc(N3CCNCC3)c2c(=O)[nH]1]

8-(piperazin-1-yl)-3-propyl-6-(3,6,6-trimethyl-4-oxo-4,5,6,7-tetrahydro-1H-indazol-1-yl)isoquinolin-1(2H)-one (5d): 14 mg, Yield 45%; $^1$H NMR (400 MHz, Chloroform-d) δ 9.59 (s, 1H), 6.99 (dd, J=26.4, 2.1 Hz, 2H), 6.17 (s, 1H), 3.13 (s, 6H), 2.79 (s, 2H), 2.50 (s, 5H), 2.35 (s, 2H), 2.27-2.01 (m, 2H), 1.68 (h, J=7.4 Hz, 2H), 1.05 (s, 6H), 0.95 (t, J=7.3 Hz, 3H). $^{13}$C NMR (126 MHz, CDCl$_3$) δ 193.4, 161.7, 155.8, 150.3, 149.1, 143.0, 142.2, 141.9, 117.4, 115.5, 112.7, 109.8, 104.3, 54.3, 52.4 (2), 46.1 (2), 37.6, 35.9, 34.9, 28.5 (2), 21.2, 13.5, 13.5. HRMS (ESI) m/z [M+H] calculated for C$_{26}$H$_{34}$N$_5$O$_2$, 448.2713, found 448.2706.

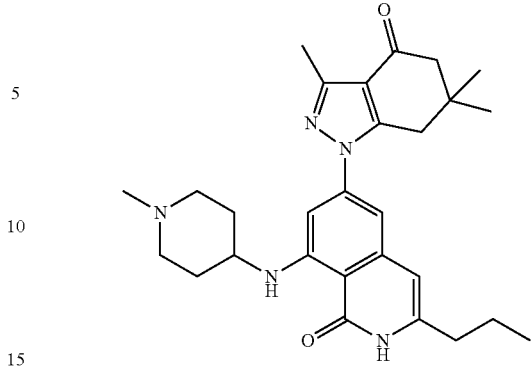

8-((1-methylpiperidin-4-yl)amino)-3-propyl-6-(3,6,6-trimethyl-4-oxo-4,5,6,7-tetrahydro-1Hindazol-1-yl)isoquinolin-1(2H)-one (5f): 13 mg, Yield 40%; $^1$H NMR (400 MHz, Chloroform-d) δ 9.56 (s, 1H), 9.35 (d, J=7.3 Hz, 1H), 6.55 (dd, J=26.8, 2.0 Hz, 2H), 6.19 (d, J=1.9 Hz, 1H), 2.87 (s, 2H), 2.80 (s, 1H), 2.57 (s, 3H), 2.52 (t, J=7.4 Hz, 2H), 2.43 (s, 2H), 2.33 (s, 3H), 2.26 (t, J=10.5 Hz, 2H), 2.16-2.08 (m, 2H), 1.79-1.58 (m, 7H), 1.13 (s, 6H), 1.01 (t, J=7.4 Hz, 3H). $^{13}$C NMR (101 MHz, CDCl$_3$) δ193.5, 165.8, 151.3, 149.9, 149.1, 143.1, 142.1, 141.6, 140.8, 107.6, 105.3, 105.0, 100.2, 52.4, 46.3, 37.7, 35.8, 34.9 (2), 32.1, 31.6, 31.4, 28.4 (2), 21.2 (2), 13.5, 13.4. HRMS (ESI) m/z [M+Na] calculated for C$_{28}$H$_{37}$N$_5$O$_2$Na, 498.2845, found 498.2823.

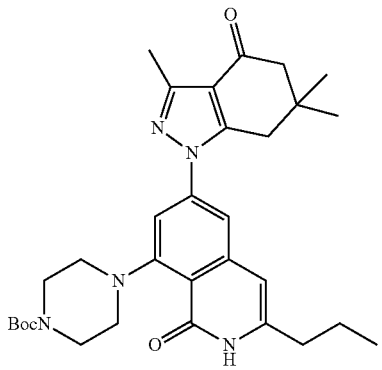 [SMILES: CCCc1cc2cc(-n3nc(C)c4c3CC(C)(C)CC4=O)cc(N3CCN(C(=O)OC(C)(C)C)CC3)c2c(=O)[nH]1]

tert-butyl 4-(1-oxo-3-propyl-6-(3,6,6-trimethyl-4-oxo-4,5,6,7-tetrahydro-1H-indazol-1-yl)-1,2-dihydroisoquinolin-8-yl)piperazine-1-carboxylate (5e): 20 mg, Yield 53%; $^1$H NMR (500 MHz, Chloroform-d) δ 8.93 (s, 1H), 7.01 (d, J=2.0 Hz, 1H), 6.96 (d, J=2.1 Hz, 1H), 6.16 (d, J=2.0 Hz, 1H), 3.75 (s, 4H), 3.08 (s, 4H), 2.79 (s, 2H), 2.51-2.43 (m, 5H), 2.35 (s, 2H), 1.66 (h, J=7.4 Hz, 2H), 1.42 (s, 9H), 1.05 (s, 6H), 0.94 (t, J=7.3 Hz, 3H). $^{13}$C NMR (126 MHz, CDCl$_3$) δ 193.4, 161.8, 155.4, 154.9, 150.4, 149.1, 143.0, 142.5, 141.9, 117.5, 115.6, 112.9, 110.0, 104.2, 79.8, 53.0 (2), 52.4 (2), 37.6, 35.9, 34.9, 31.6, 28.5 (4), 21.1, 13.5, 13.5. HRMS (ESI) m/z [M+H] calculated for C$_{31}$H$_{42}$N$_5$O$_4$, 548.3237, found 548.3226.

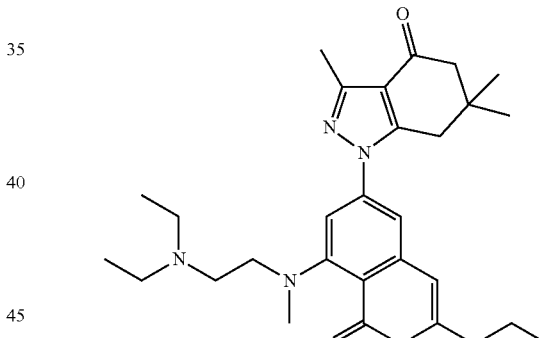

8-((2-(diethylamino)ethyl)(methyl)amino)-3-propyl-6-(3,6,6-trimethyl-4-oxo-4,5,6,7-tetrahydro-1H-indazol-1-yl)isoquinolin-1(2H)-one (5g): 14 mg, Yield 45%; $^1$H NMR (500 MHz, Chloroform-d) δ 9.22 (s, 1H), 7.02 (dd, J=16.0, 2.0 Hz, 2H), 6.21 (s, 1H), 3.44-3.37 (m, 2H), 3.02 (s, 3H), 2.86 (s, 2H), 2.77 (t, J=7.4 Hz, 2H), 2.57 (s, 3H), 2.56-2.48 (m, 6H), 2.42 (s, 2H), 1.81-1.71 (m, 2H), 1.12 (s, 6H), 1.03 (t, J=7.3 Hz, 3H), 0.97 (t, J=7.1 Hz, 6H). $^{13}$C NMR (126 MHz, CDCl$_3$) δ 193.5, 162.0, 155.2, 150.1, 149.1, 142.9, 141.5, 117.3, 114.5, 111.4, 110.0, 104.3, 55.5, 52.4, 50.4, 47.3 (2), 41.7, 37.5, 35.9, 35.0, 29.9, 28.4 (2), 21.2, 13.6, 13.5 (2), 11.7. HRMS (ESI) m/z [M+H] calculated for C$_{29}$H$_{42}$N$_5$O$_2$, 492.3338, found 492.3352.

General Procedure for the synthesis of 6a and 6b: To a solution of 4d or 5b (0.1 mmol, 1 eq) in 10 mL ethanol was introduced Palladium (10% on activated carbon) (10 mol %) in a pressure reactor vessel. After multiple cycles of degassing under vacuum, hydrogen gas was introduced at 200 psi and the reactor vessel was heated to 90° C. for 24 h. Upon completion, the reaction mixture was passed through a plug of Celite and solvent was removed under vacuum. Subsequently, preparative TLC was performed (SiO$_2$, 5% MeOH in dichloromethane) to obtain the desired compounds.

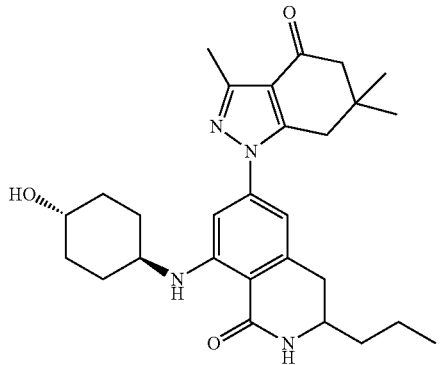 [SMILES: CCCC1Cc2cc(-n3nc(C)c4c3CC(C)(C)CC4=O)cc(N[C@H]3CC[C@H](O)CC3)c2C(=O)N1]

8-(((1r,4r)-4-hydroxycyclohexyl)amino)-3-propyl-6-(3,6,6-trimethyl-4-oxo-4,5,6,7-tetrahydro-1H-indazol-1-yl)-3,4-dihydroisoquinolin-1(2H)-one (6a): White amorphous solid, 20 mg, Yield 42%. $^1$H NMR (400 MHz, Chloroform-d) δ 8.78 (d, J=7.5 Hz, 1H), 6.53 (dd, J=26.1, 2.0 Hz, 2H), 5.72 (s, 1H), 3.75 (dt, J=9.6, 4.9 Hz, 1H), 3.60 (m, J=8.4, 6.8, 5.0, 2.7 Hz, 1H), 3.40-3.27 (m, 1H), 2.91 (dd, J=15.4, 4.2 Hz, 1H), 2.83 (s, 2H), 2.74 (dd, J=15.3, 10.5 Hz, 1H), 2.55 (s, 3H), 2.41 (s, 2H), 2.23-1.98 (m, 4H), 1.64-1.52 (m, 2H), 1.50-1.36 (m, 6H), 1.12 (s, 6H), 0.97 (t, J=7.2 Hz, 3H). $^{13}$C NMR (101 MHz, CDCl$_3$) δ 193.4, 168.7, 150.7, 150.0, 148.9, 142.3, 142.0, 117.2, 108.5, 107.9, 104.1, 69.6, 53.4, 52.3, 50.5, 50.2, 37.7, 37.2, 35.8, 35.6, 33.6, 30.2, 30.1 (2), 28.4, 18.6, 13.9, 13.4.

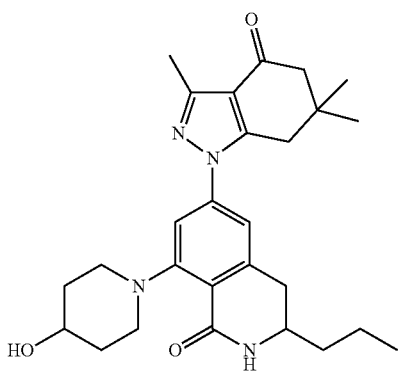

8-(4-hydroxypiperidin-1-yl)-3-propyl-6-(3,6,6-trimethyl-4-oxo-4,5,6,7-tetrahydro-1Hindazol-1-yl)-3,4-dihydroisoquinolin-1(2H)-one (6b): White amorphous solid, 24 mg, Yield 47%. $^1$H NMR (400 MHz, Chloroform-d) δ 6.89 (dd, J=36.5, 2.1 Hz, 2H), 6.01-5.90 (m, 1H), 3.88 (dd, J=8.5, 4.6 Hz, 1H), 3.66-3.54 (m, J=10.5, 6.6, 3.2 Hz, 1H), 3.50-3.32 (m, 3H), 3.05-2.88 (m, 3H), 2.82-2.71 (m, 3H), 2.54 (s, 3H), 2.42-2.36 (m, 2H), 2.16-1.98 (m, 1H), 1.99-1.74 (m, 2H), 1.65-1.52 (m, 2H), 1.51-1.37 (m, J=14.3, 7.2, 5.1 Hz, 2H), 1.10 (d, J=6.6 Hz, 6H), 0.97 (t, J=7.2 Hz, 3H). $^{13}$C NMR (101 MHz, CDCl$_3$) δ 193.4, 165.2, 153.8, 150.1, 149.0, 143.0, 141.1, 118.1, 117.2, 114.0, 111.8, 67.4, 52.3, 50.2, 50.1, 49.5, 37.4, 36.9, 36.8, 35.9, 34.3, 34.2, 28.5, 28.3, 18.8, 13.9, 13.4.

Example 2

Figure 1A:
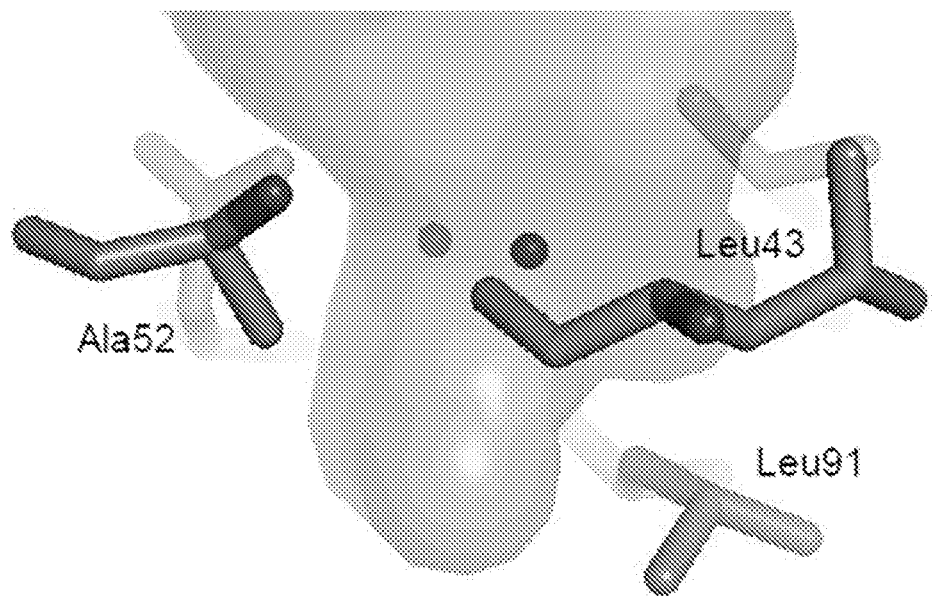
Figure 1B:
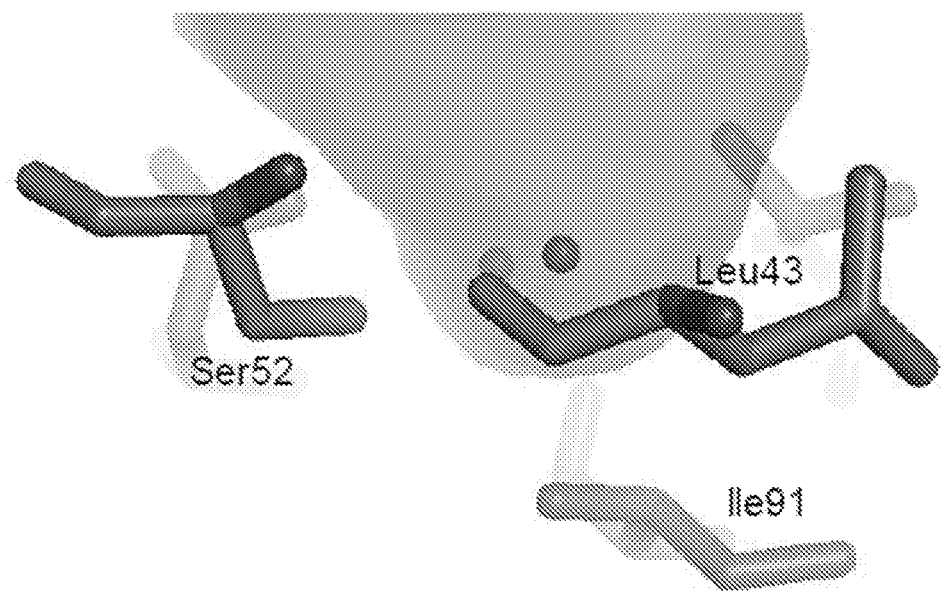
Figure 1C:
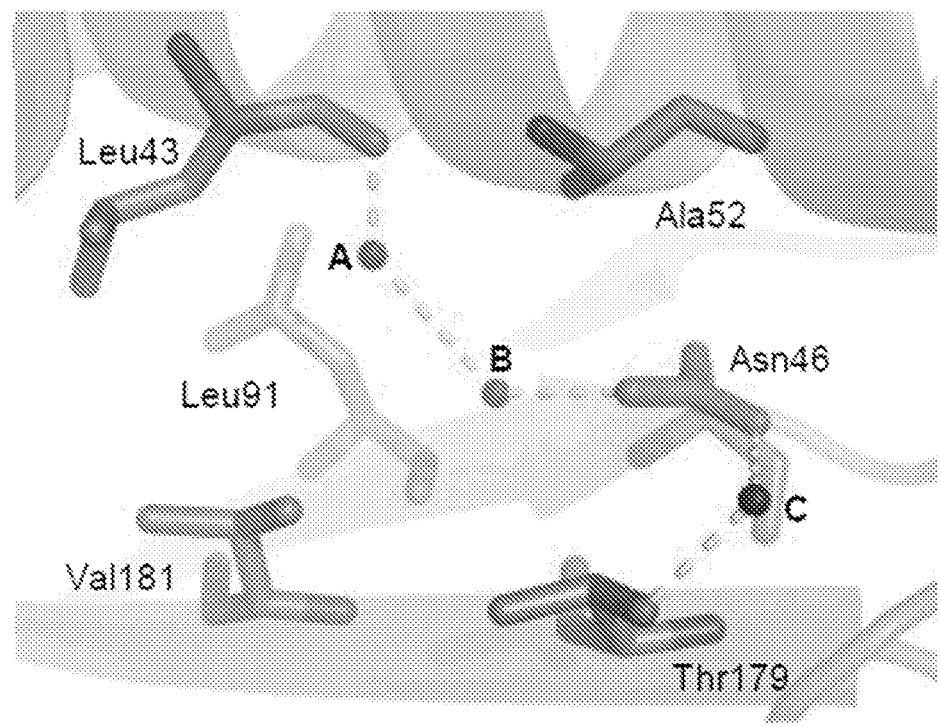
Figure 1D:
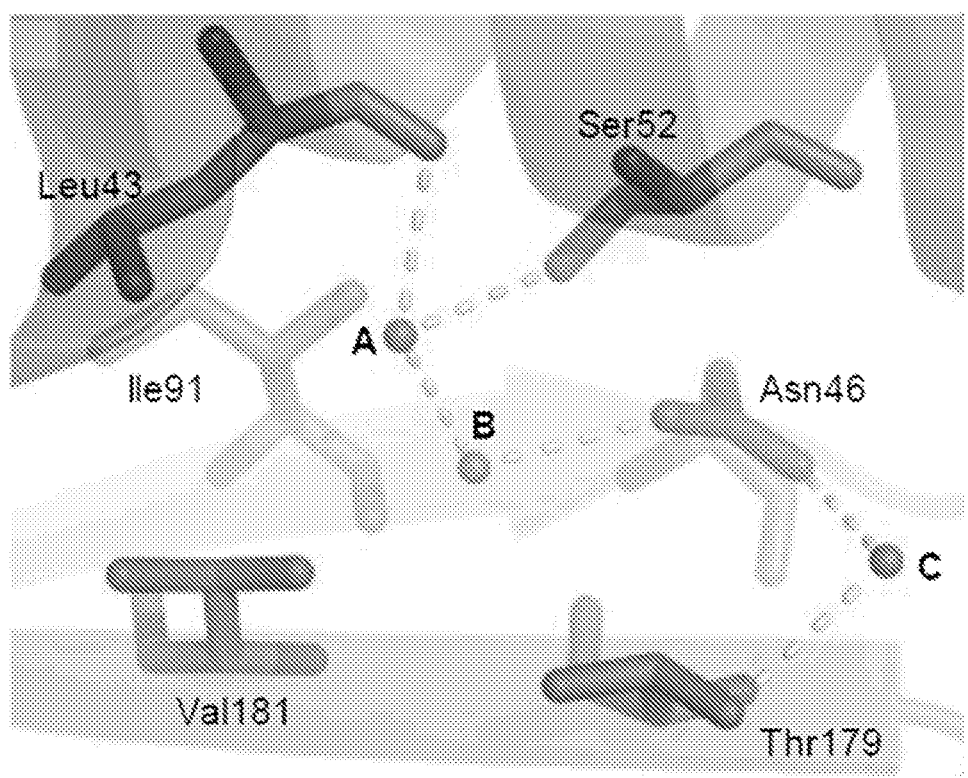
Figure 2:
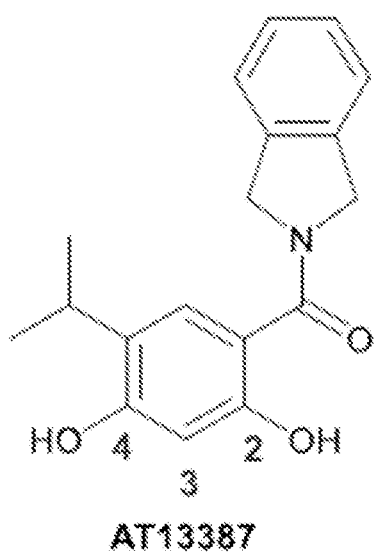
FIG. 2 is a two-dimensional representation of the Hsp90β binding pocket with known pan-inhibitor AT13387.
Figure 2:
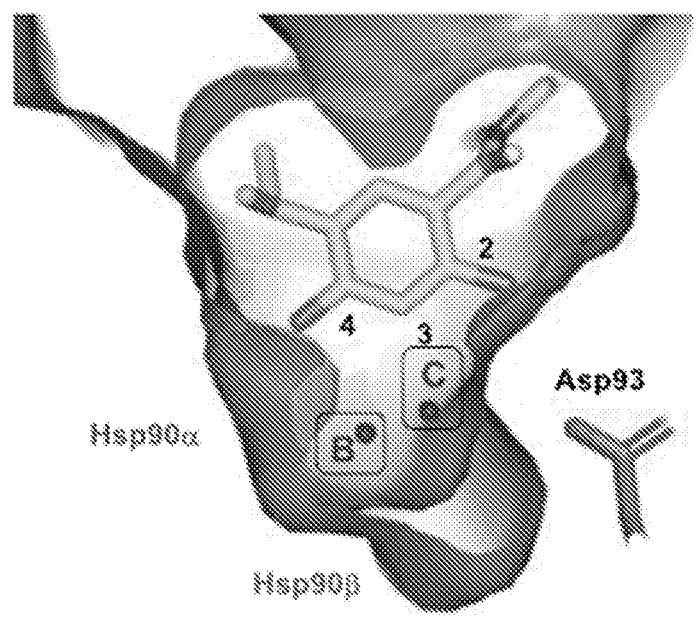
Figure 2:
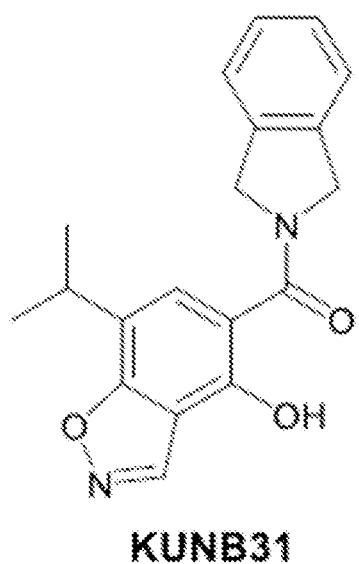
Figure 2:
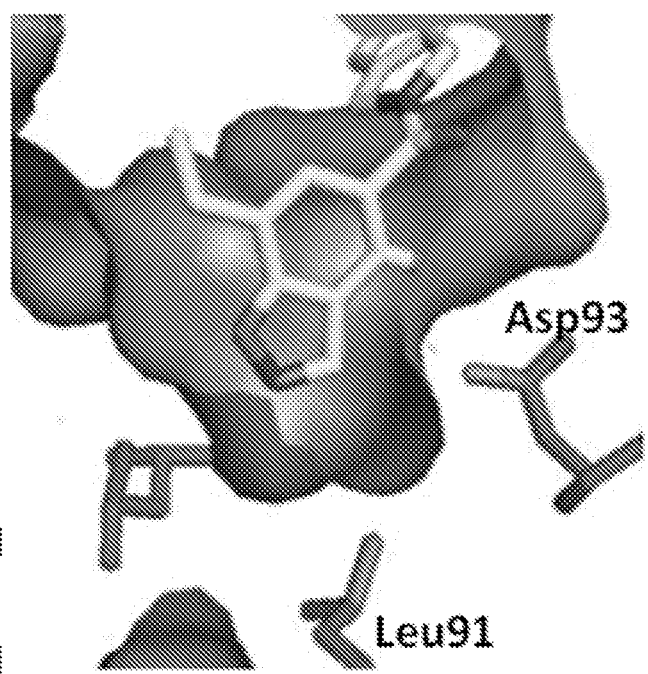

Sequence alignment of the residues that form the Hsp90α and Hsp90β N-terminal ATP-binding pockets revealed Hsp90β to contain Ala52 and Leu91 in lieu of Ser52 and Ile91, which are present in Hsp90α (FIG. 1A and FIG. 1). Substitution of these two amino acids results in a small and extended binding pocket in Hsp90α (FIG. 1A and FIG. 1), due to the increased flexibility of Leu91, which allows it to pack into the binding pocket, unlike Ile91 in Hsp90α (FIG. 1A). In addition, all four Hsp90 isoforms contain a water-mediated hydrogen bond network at the bottom of the binding pocket to facilitate Hsp90's interactions with ligands, as shown in FIG. 2. In silico overlay of the Hsp90α and Hsp90β co-crystal structures indicate these water molecules play a different role in each isoform. Ser52 is replaced with Ala52 in Hsp90β and forms a hydrogen bond with bound water molecule A, whereas Ala52 does not participate in the hydrogen bonding network. Therefore, it was hypothesized that Hsp90β-selective inhibitors could be developed via the introduction of substituents that sterically clash with Ile91 in Hsp90α and consequently, disrupt the water-mediated hydrogen bonding network.

Displacement of water molecule A can occur via modifications to the 4-position of the resorcinol-based scaffold, KUNB31 (FIG. 2). Substitutions at the 4-position do not increase selectivity for Hsp90β, but instead, increase affinity by displacing the conserved water molecules and establishing direct hydrogen bonding interactions with Hsp90. In contrast, displacement of water molecule B via modifications at the 3-position confers selectivity, but decreases binding affinity. Substituents at the 3-position of the resorcinol ring also create unfavorable steric interactions with the bulkier side chains present in Hsp90α (Ser52, Ile 91), and appear to increase the entropy of binding through displacement of water molecule B. KUNB31 is a ring-constrained variant that consists of substitutions at the 3- and 4-positions and was designed to minimize the entropic penalty upon binding Hsp90β, while simultaneously displacing water molecules A and B (FIG. 1C). KUNB31 was found to manifest an apparent Kd of 180 nM against Hsp90β and 50-fold selectivity versus other Hsp90 isoforms. Through solution of the co-crystal structure, it was confirmed that KUNB31 displaced both water molecules, and validated this approach toward the development of Hsp900-selective inhibitors. Based on these observations, a new scaffold was pursued in an effort to improve both affinity and selectivity for Hsp90β.

Example 3

Figure 3:
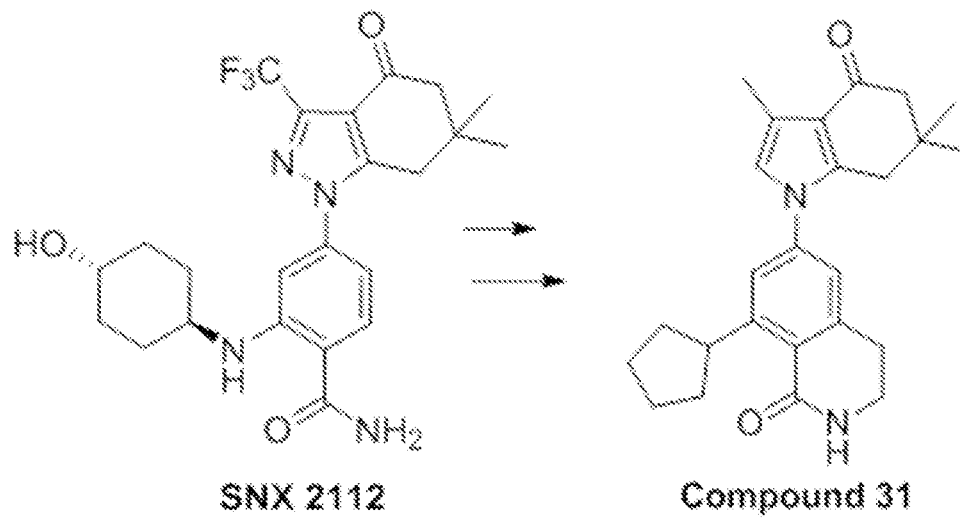
FIG. 3 shows the structures and the binding affinities (Kd) of the benzamide-based Hsp90 inhibitors, and the proposed binding mode generated in silico.
Figure 3:
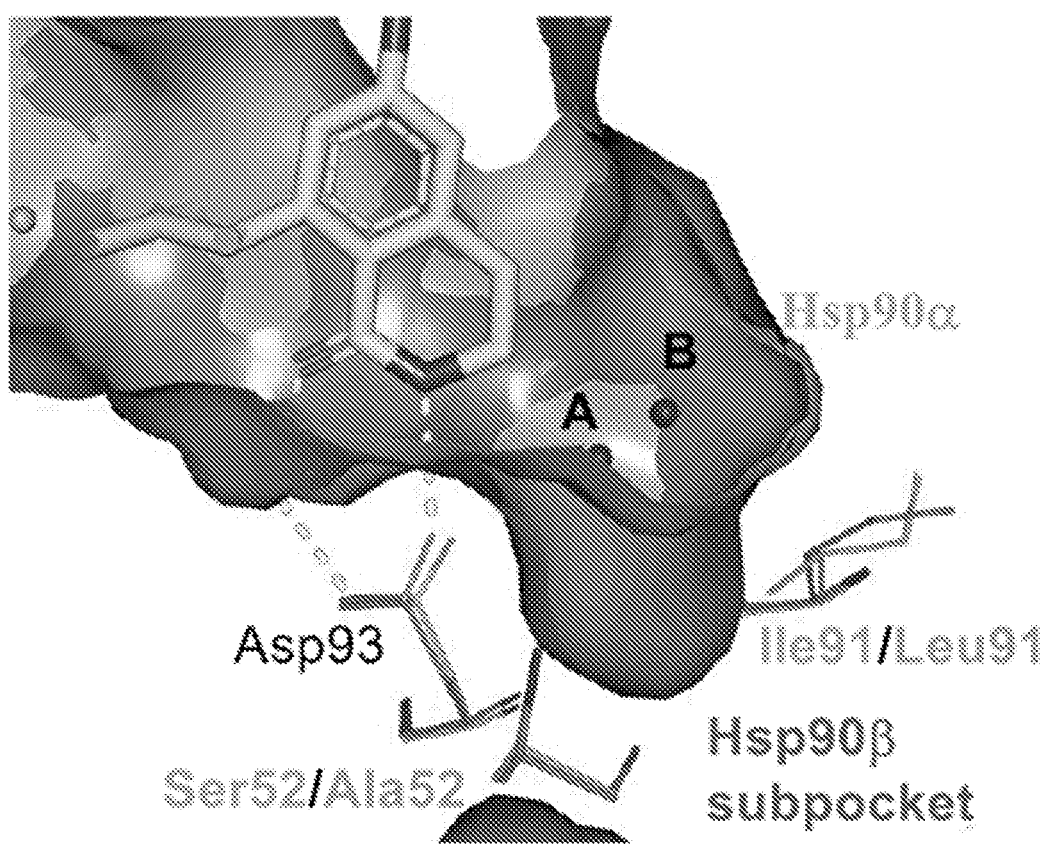

SNX 2112 is a benzamide-containing Hsp90 inhibitor that was previously reported (FIG. 3) and shown to exhibit equipotent affinity for both Hsp90α and Hsp90β (FIG. 3). Subsequent optimization by Vertex Pharmaceuticals led to compound 31, which manifests selective inhibition of both Hsp90α and Hsp90β without affinity for Grp94 and Trap1. The co-crystal structure of compound 31 (PDB code: 4OOB) bound to Hsp90α was over-laid with the Hsp90β co-crystal structure (PDB code: 1UYM), which revealed compound 31 does not interfere with the conserved water molecules found in the Hsp90α/pockets (depicted as spheres in FIG. 1A and FIG. 1B, labeled as A and B in FIG. 3). Compound 31 contains a ring-constrained benzamide group, which appears to lock the amide into a rigid conformation that facilitates interaction with Asp93. Molecular modeling studies with compound 31 suggested that modifications to the 2'-position (FIG. 3 and FIG. 4) could displace the conserved water molecules and extend into the Hsp90β subpocket and produce Hsp90β selective inhibition.

Figure 4:
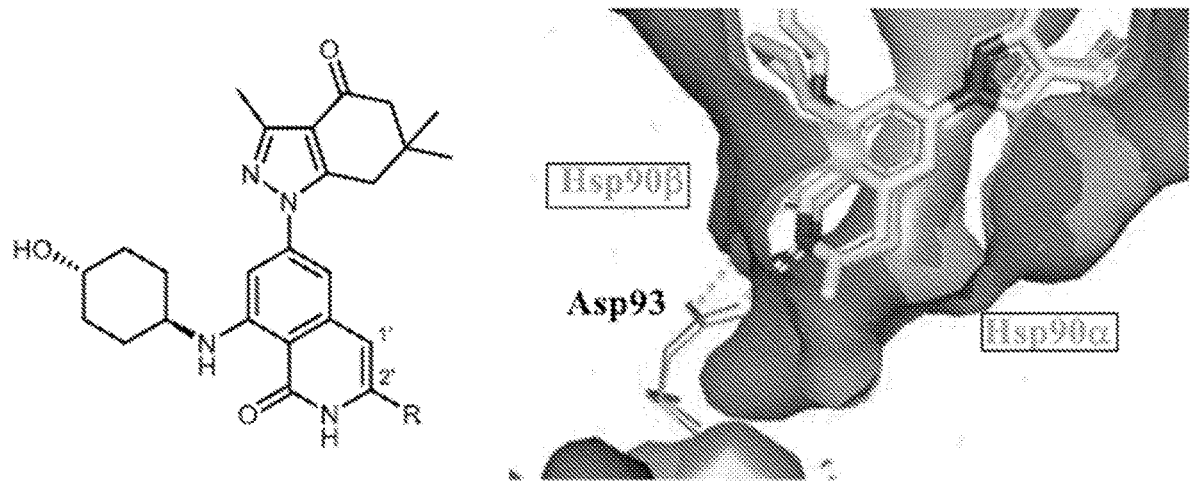
FIG. 4 shows an in silico generated overlay of compound 4a, left, with compound 31.

In addition to modifications at the 2-position, the cyclopentyl group was replaced with a trans-4-cylcohexanolamine to enhance alignment and increase solubility. The tetrahydroindazolone fragment was also incorporated in lieu of the pyrazolone present in compound 31, and did not affect affinity. The unsaturated alkene was used to explore the spatial constraints of the Hsp90β subpocket, as computational studies supported that its introduction would allow the benzamide to maintain key interactions with Asp93 and Thr184 (FIG. 3). The 2'-position appeared to project moieties toward the Hsp900-specific subpocket, allowing the inclusion of appendages to investigate this subpocket as depicted in FIG. 4. Given the hydrophobic nature of the Hsp90β subpocket, linear aliphatic chains were attached to the 2'-position for the development of initial analogs. In addition, methyl ethers and alcohols were also attached to the 2'-position to probe for beneficial interactions with Leu-48 (in both a and p) and/or Ser-52 in Hsp90α.

Figure 5:
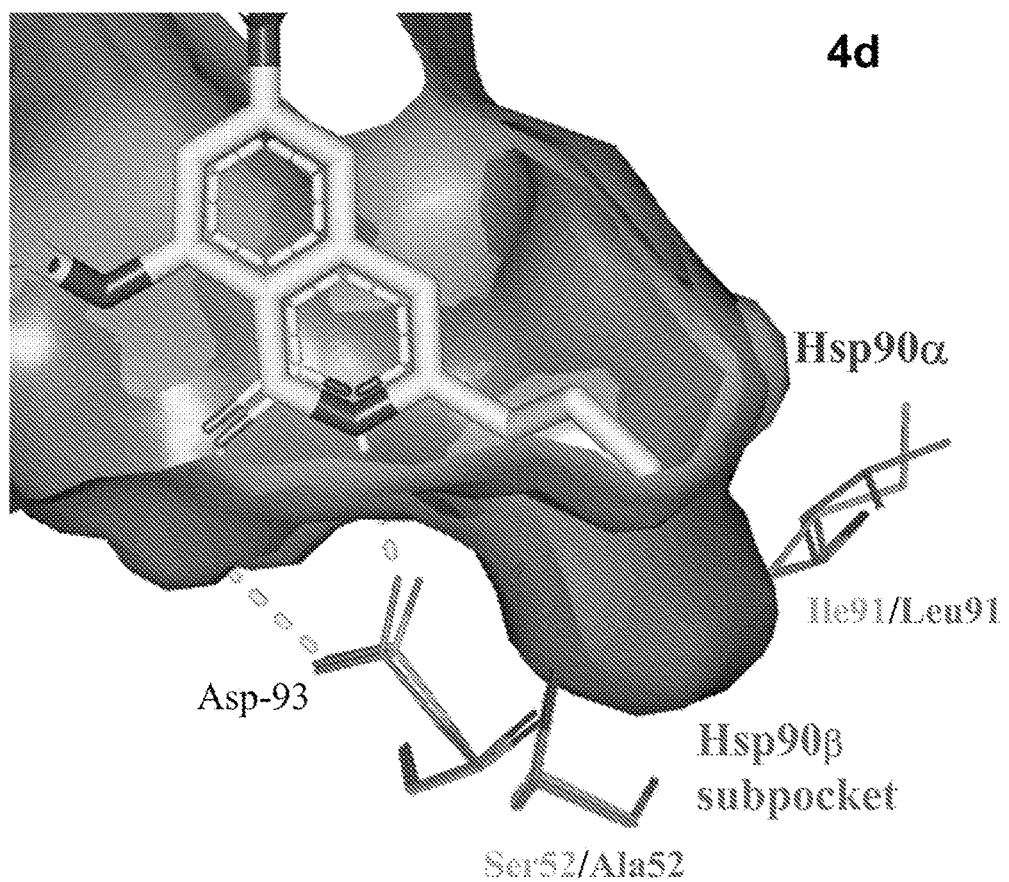
FIG. 5 shows compound 4d modeled in the Hsp90α and Hsp90β binding pockets.
Figure 6:
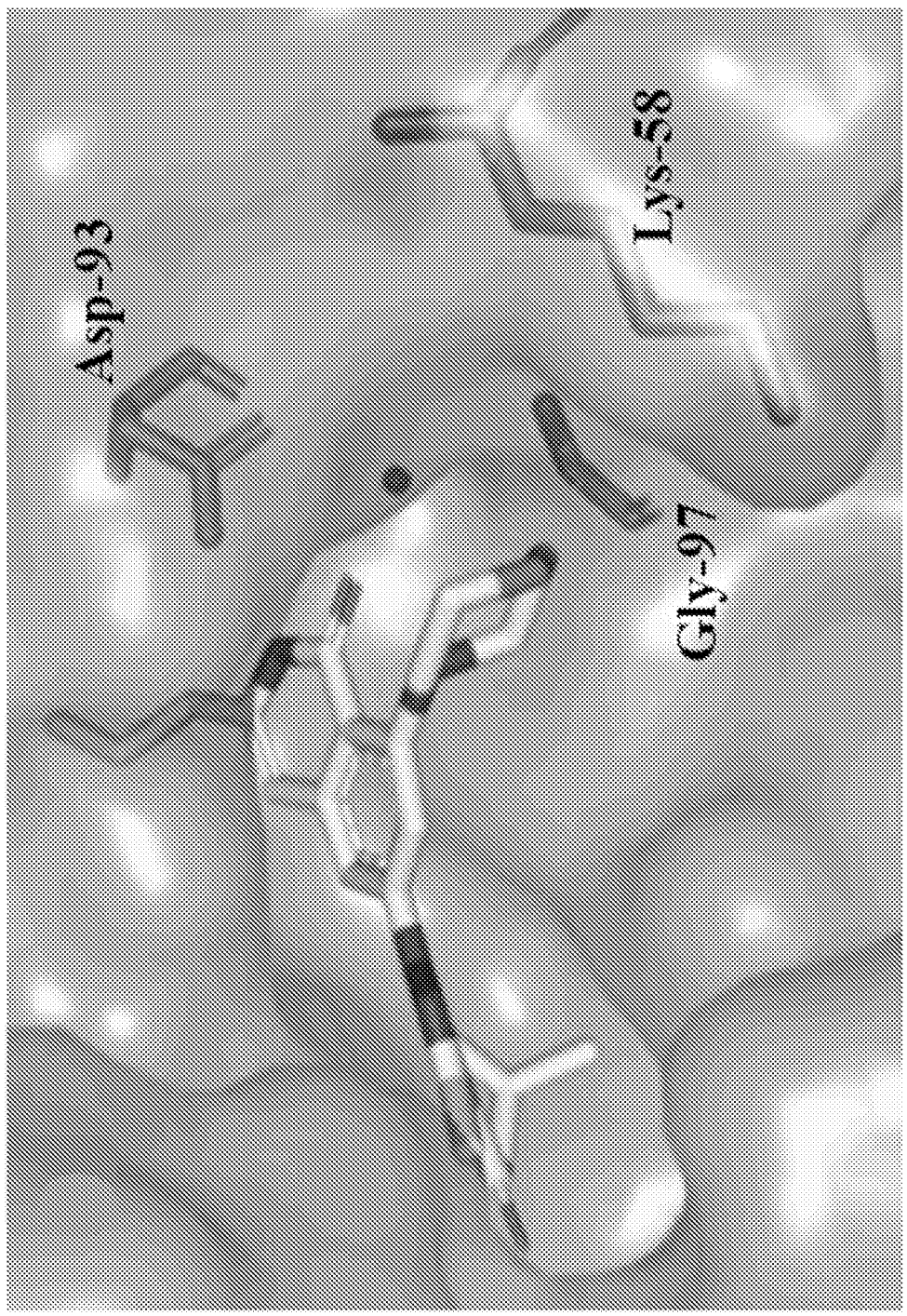
FIG. 6 shows a compound 5a docking to the Hsp90β ATP binding site.

Once prepared, the compounds were evaluated for their binding affinities against the cytosolic isoforms, Hsp90α and Hsp90β by measuring their ability to competitively displace FITC labeled Geldanamycin (GDA) in a fluorescence polarization assay (apparent Kd's listed in Table 1). The first compound in the series, 4a, contained a methyl at the 2'-position and exhibited 3-fold selectivity for Hsp90β, suggesting that further modification could enhance selectivity. Elongation of the chain to include an ethyl appendage (4b), enhanced affinity for both Hsp90α and Hsp90β, which occurs by occupation of the subpocket in both isoforms. An isopropyl group was installed to generate 4c, which maintained similar affinity and selectivity as 4b, establishing that a branched aliphatic chain can be accommodated within these subpockets. However, increasing the chain length to the propyl derivative (4d) led to an improvement in both affinity and selectivity, as 4d manifested ~40 nM Kd for Hsp90β and ~21-fold selectivity over Hsp90α (FIG. 5). In addition, 4d exhibited a decreased binding affinity towards Trap-1 and Grp94 (>5 μM for both isoforms). Encouraged by these results, a butyl chain was incorporated to probe the depth of the Hsp90β subpocket. A compound that contained an n-butyl group (4e) was found to exhibit excellent selectivity for Hsp90β (>300-fold versus Hsp90α), but a reduced affinity (Kd=186 nM). Since the isopropyl group was accommodated in both Hsp90α and Hsp90β, a t-butyl appendage was attached (4e) to determine whether the pocket could accommodate spherical bulk. Compound 4e did not bind either isoform. Compound 4g was synthesized to contain an isobutyl group, which maintained selectivity, but led to a decrease in affinity. A cyclopropyl group was also evaluated (4h) and a loss of potency was observed as compared to 4c. Surprisingly, compounds 4i and 4j displayed a loss of selectivity for Hsp90β over Hsp90α, and contained polar appendages. The alkyne (4k) was investigated to determine whether a linear substituent could project into the subpocket and affect selectivity. Disappointingly, the acetylene group was found to occupy both Hsp90 isoforms without discrimination.

TABLE 1

Apparent Kd values of compounds 4a-k for Hsp90α and Hsp90β determined using fluorescence polarization (FP) assay.

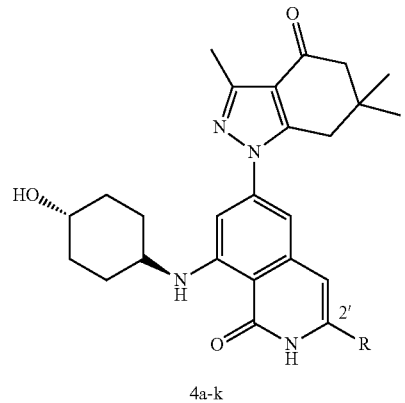

4a-k

| Compound | R group | Hsp90α Kd (μM) | Hsp90β Kd (μM) |
|---|---|---|---|
| 4a | Methyl | 0.294 ± 0.023 | 0.101 ± 0.003 |
| 4b | Ethyl | 0.180 ± 0.036 | 0.068 ± 0.008 |
| 4c | Isopropyl | 0.173 ± 0.036 | 0.051 ± 0.008 |
| 4d | Propyl | 0.886 ± 0.040 | 0.040 ± 0.003 |
| 4e | Butyl | >50 | 0.156 ± 0.018 |
| 4f | t-Butyl | >50 | >50 |
| 4g | ⟨isobutyl⟩ | >50 | 0.264 ± 0.030 |
| 4h | Cyclopropyl | 1.88 ± 0.28 | 0.946 ± 0.038 |
| 4i | —CH₂OCH₃ | 0.306 ± 0.023 | 0.159 ± 0.003 |
| 4j | —CH₂OH | 0.824 ± 0.104 | 0.233 ± 0.018 |
| 4k | ⟨alkyne⟩ | 0.381 ± 0.003 | 0.337 ± 0.015 |

Example 4

Figure 7:
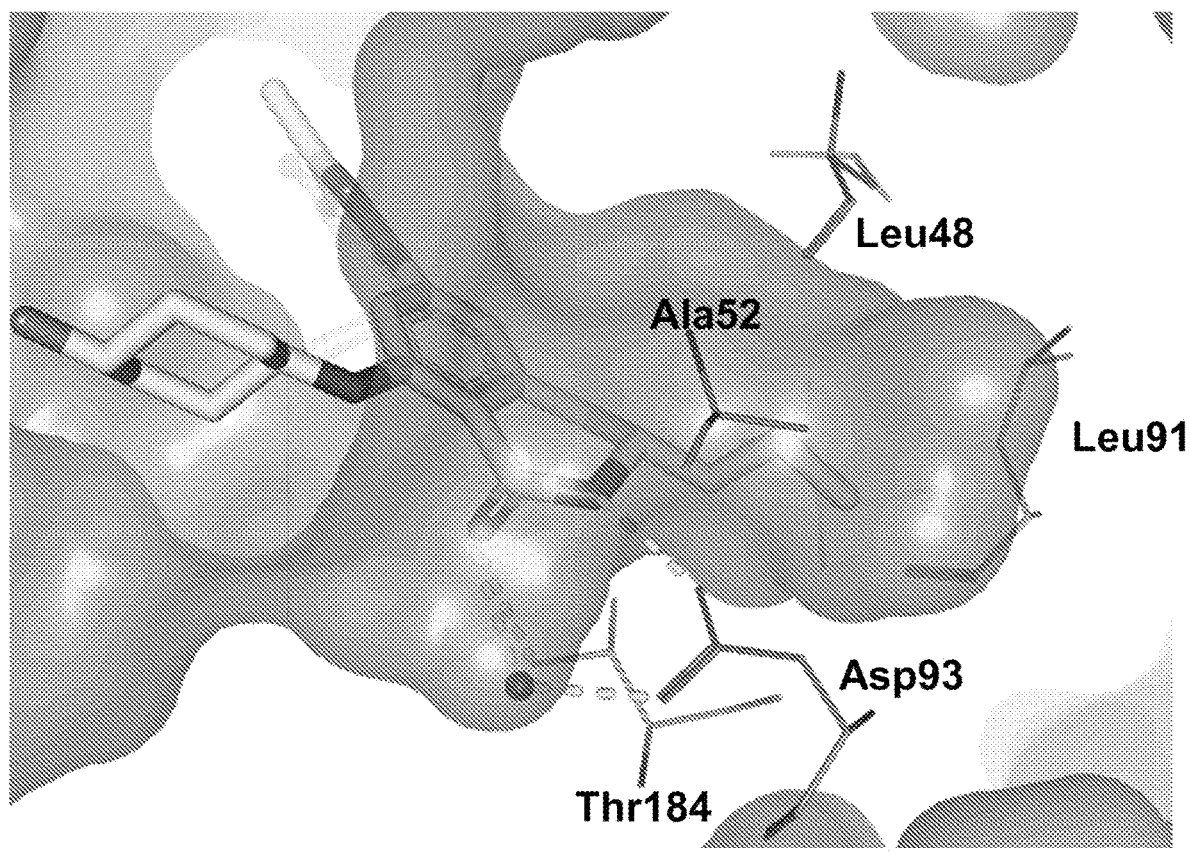
FIG. 7 shows the proposed binding modes of compound 5a in the Hsp90β binding site.

Computational studies with 4d suggested that the trans-4-aminocyclohexanol may alter the conformation (FIG. 7) and potentially, affinity and selectivity. The computationally derived binding modes for 5a are presented in FIG. 7 and suggest a slight rotation of the isoquinolin-1(2H)-one ring, which appears to result from disfavored interactions between the morpholine ring and the protein surface. This conformational change appears to align the 2'-appendage at an angle that is not optimized for selectivity nor affinity for Hsp90β. An additional reason to replace the trans-4-aminocyclohexanol is to disrupt the planarity that is caused by the intramolecular hydrogen bond between the aniline and carbonyl moieties (5a, FIG. 7), which is likely to also effect solubility. Therefore, replacements were investigated to include various functional groups, including ionizable tertiary amines to improve solubility. Compounds 5a-g were prepared from 3d.

Upon their preparation, compounds 5a-g were evaluated for their binding affinity against the cytosolic Hsp90 isoforms (Table 2). The binding profile of the morpholine containing compound, 5a, was consistent with the proposed hypothesis and exhibited excellent selectivity for Hsp90β with a Kd of ~121 nM. The binding profile for 5a mirrored 4e, which contains an n-butyl group at the 2'-position. This data suggests that with 5a, the propyl chain aligns in Hsp90β in a manner similar to the butyl chain of 4e, and thus, increases selectivity. Compound 5b, which contains an alcohol, was proposed to interact with the amino acids at the gate of the binding pocket, such as Gly-97 and Lys-58. Alcohol 5b was found to exhibit a ~91 nM Kd for Hsp90β with >400-fold selectivity over Hsp90α, and supports the proposed binding model. Incorporation of N-methyl piperazine (5c), led to a decrease in affinity and selectivity as compared to 5a and 5b, which is likely to result from unfavorable interactions with Lys-58, which is present in both isoforms.

Figure 8:
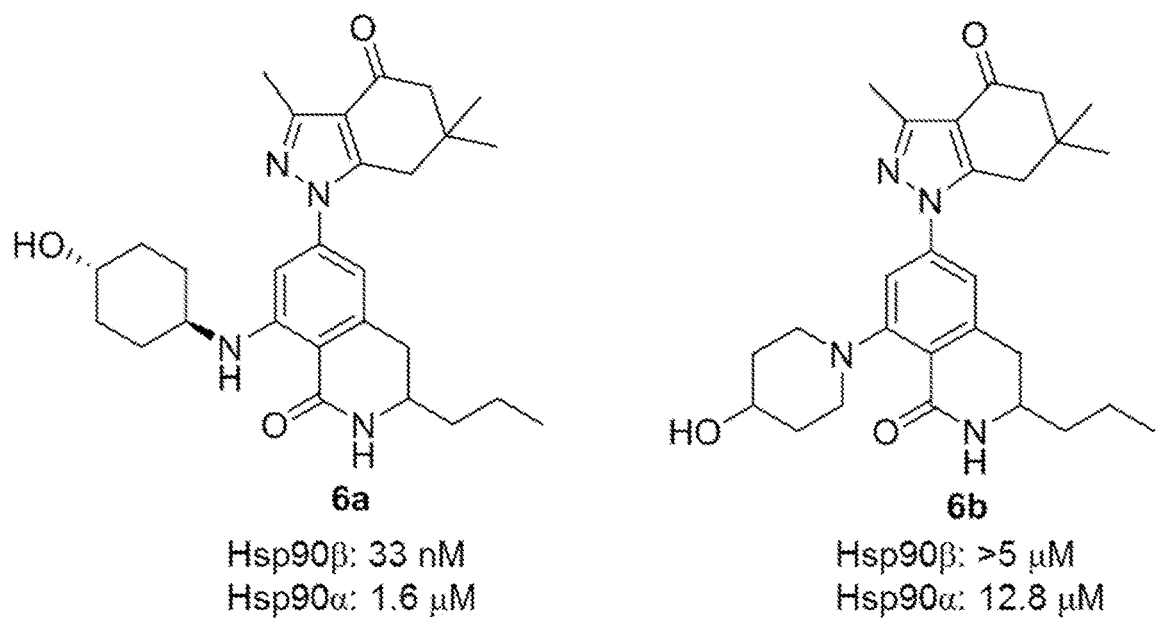
FIG. 8 shows the structures and apparent Kd values of compounds 6a and 6b against Hsp90α and Hsp90β determined using fluorescence polarization (FP) assay.

Similarly, compounds 5d-g manifested reduced affinity for Hsp90β. Based on the proposed binding model it appears that the carbonyl electrons could participate in stronger hydrogen bonding interactions if the lactam was more flexible. In addition, this flexibility would allow appendages at the 2-position to project more efficiently into the Hsp90β-specific subpocket. Therefore, the saturated lactams 6a and 6b were pursued as shown in FIG. 8. Upon evaluation, 6a was shown to exhibit increased binding affinity as well as enhanced selectivity versus Hsp90α, while 6b lost both selectivity and affinity (FIG. 8).

TABLE 2

Apparent Kd values of compounds 5a-g for Hsp90α and Hsp90β determined using fluorescence polarization (FP) assay.

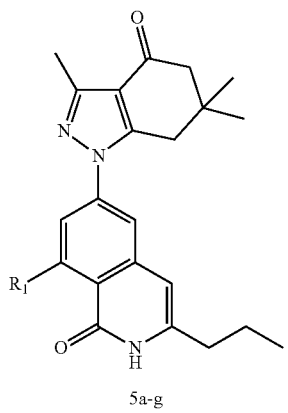

5a-g

| Compound | R group | Hsp90α $K_d$ (µM) | Hsp90β $K_d$ (µM) |
|---|---|---|---|
| 5a | morpholine | >50 | 0.121 ± 0.017 |
| 5b | 4-hydroxypiperidine | 38.00 ± 1.10 | 0.091 ± 0.010 |
| 5c | N-methylpiperazine | 8.52 ± 0.24 | 0.426 ± 0.053 |
| 5d | piperazine | >50 | 4.47 ± 0.278 |
| 5e | N-Boc-piperazine | >50 | 0.463 ± 0.031 |

TABLE 2-continued

Apparent Kd values of compounds 5a-g for Hsp90α and Hsp90β
determined using fluorescence polarization (FP) assay.

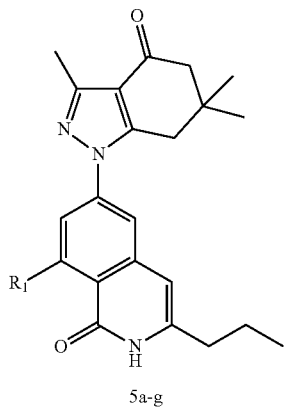

5a-g

| Compound | R group | Hsp90α $K_d$ (µM) | Hsp90β $K_d$ (µM) |
|---|---|---|---|
| 5f | (N-methylpiperidin-4-yl)amino | 17.083 ± 0.66 | 0.513 ± 0.067 |
| 5g | (2-(diethylamino)ethyl)(methyl)amino | >50 | 4.46 ± 0.188 |

Example 5

Compound 4d was evaluated for its growth inhibitory activity against the NCI-60 cancer cell line panel, and shown to manifest potent inhibition of select cancers. Interestingly, 4d exhibited $GI_{50}$'s below 100 nM against several cancers, including, leukemia, colon, breast and renal carcinoma. For example, HT29 cells were sensitive to 4d, which manifested a $GI_{50}$ of 26 nM, while other colon cancer cells were also strongly inhibited and $GI_{50}$'s ranged from 50-80 nM. Compound 4d was also evaluated for inhibitory activity against urological cancers, such as bladder and prostate cancer. As noted in Table 3, 4d was found to manifest $GI_{50}$ values of ~508 nM and ~196 nM against UM-UC-3 and T24 bladder cancer cells, respectively. Whereas, the efficacy of 4d against prostate cancer cells ranged between 1-2.5 µM (Table 3).

TABLE 3

$GI_{50}$ values of 4d against urological cancer cells.

| | Cell Line | $GI_{50}$ |
|---|---|---|
| Bladder Cancer | UM-UC3 | 5.084e-007 |
| | T24 | 1.969e-007 |
| Prostate Cancer | PC3-MM2 | 1.240e-006 |
| | LNCap-LN3 | 1.183e-006 |
| | C4-2b | 1.031e-006 |
| | LAPC4 | 2.565e-006 |

Compound 6a was also evaluated for its inhibitory activity against a variety of cancer cell lines (Table 4). 6a manifested submicromolar $IC_{50}$ values against the screened cancer cell lines, particularly against MOLM-13.

TABLE 4

$IC_{50}$ values of 6a against various cancer cell lines.

| | Cell line | $IC_{50}$ |
|---|---|---|
| Colon Cancer | HCT-116 | 265.2 nM |
| Leukemia | MOLM-13 | 39.4 nM |
| | K562 | 497.8 nM |
| Bladder Cancer | UM-UC3 | 1.05 µM |
| | HTB-9 | 811 nM |
| | HTB-5 | 935 nM |
| | HT1376 | 716 nM |

Example 6

Figure 9:
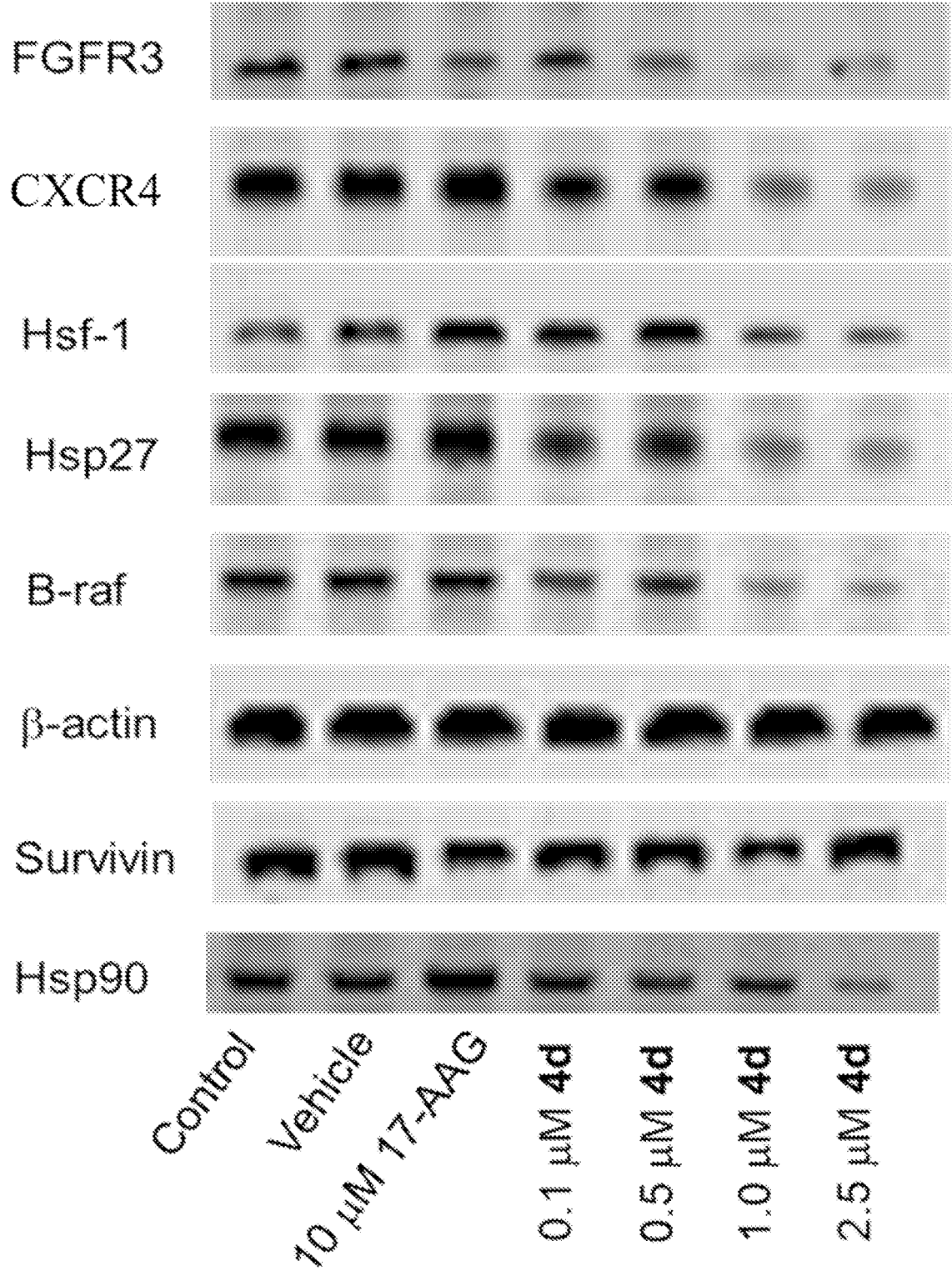
FIG. 9 shows the western blot analysis of client proteins with 4d in UM-UC-3 cells. 10 µM GDA was included as positive control and vehicle (DMSO) as negative control.

Since Hsp90 inhibition induces the degradation of Hsp90-dependent substrates via the ubiquitin-proteosome pathway, the levels of both kinase and non-kinase Hsp90 clients were assessed via western blot analysis. Known Hsp90 clients, Fibroblast growth factor receptor 3 (FGFR3) (highly mutated and/or overexpressed in nonmuscle-invasive urothelial carcinomas), CXCR4, and B-Raf, along with HSR elements Hsf-1 and Hsp27, were analyzed following the administration of 4d to UM-UC-3 cells. After a 24-hour incubation with 4d, Hsp90-dependent client proteins were reduced at concentrations that mirrored the cellular $IC_{50}$ value, clearly linking cell viability to Hsp90β inhibition (FIG. 9). A marked dose-dependent reduction in FGFR3 level was observed along with Hsp90β-dependent clients, CXCR4 and B-raf. Heat shock related proteins Hsp27 and Hsf-1, also declined upon increasing doses of 4d, which mirrored the trend previously observed with the Hsp90β- selective compound, KUNB31. Survivin, which is an Hsp90α dependent substrate was not affected, providing direct evidence for isoform-selective inhibition in a cellular context.

The saturated derivative, 6a, exhibited similar effects and induced the degradation of Hsf-1, Hsp70 and Hsp90 after 24 h exposure to HCT-116 cells (FIG. 10B). In addition, 6a induced the degradation of known Hsp90β-dependent clients; CDK4, CDK6, cIAP1, and CXCR4 (FIG. 10A). Whereas the total levels of Akt-1, and Raf-1, an Hsp90α dependent substrate, were not affected. These results provide further evidence for isoform-selective inhibition in the cell. Further, HEK293 cells expressing the hERG channel were treated with 6a to confirm Hsp90β-selective inhibition would not inhibit proper maturation and trafficking of the hERG channel (FIG. 10C). The hERG channel, an Hsp90α-dependent substrate was not affected by treatment of 6a, and confirms isoform-selective inhibition of Hsp90 may evade liabilities associated with pan-Hsp90 inhibition.

Example 7

Since compound 5b was the most selective Hsp90β inhibitor, it was evaluated in SkBr3 cells for its effectiveness on the maturation of proteins that drive oncogenesis. Hsp90α knockdown via Hsp90α siRNA was carried out to distinguish the roles of Hsp90α and Hsp90β on maturation of the known Hsp90 client, ErbB2 (HER2). HER2 belongs to the epidermal growth factor receptor family of proteins (EGFR), and exhibits intrinsic receptor tyrosine kinase activity that is over-expressed in ~30% of breast cancers and many other cancers. It is hypothesized in the literature that plasma membrane bound HER2 in SkBr3 cells is dependent upon Grp94, however, the cytosolic HER2 population is still maintained by Hsp90. Compound 5b was utilized as a chemical tool to inhibit Hsp90β which revealed HER2 to be dependent upon both cytosolic isoforms, as the inhibition of Hsp90β with 5b was not effective at reducing HER2 maturation (FIG. 11, control siRNA, 18 h reading). However, upon knockdown of Hsp90α with siRNA in the presence of 5b, the levels of HER2 were significantly reduced. Therefore, HER2 maturation exhibits redundant dependency upon both Hsp90 isoforms and therefore, a functional loss of Hsp90β can be compensated for by Hsp90α for HER2. Unlike the pan-inhibitor, GDA, 5b did not induce the heat shock response even at 10 µM (FIG. 11, control siRNA, 18 h), which is an attribute of Hsp90β-selective inhibitors. In addition, known Hsp90β dependent clients such as CDK4 and c-IAP1 were degraded in a dose-dependent manner upon increasing concentrations of 5b, but were unaffected by Hsp90α knockdown.

For reasons of completeness, various aspects of the invention are set out in the following numbered clauses:

Clause 1. A compound of formula (I),

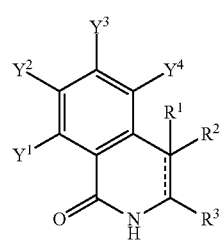

(I)

or a pharmaceutically acceptable salt thereof, wherein
the dashed line (-----) represents an optional double bond;
$R^1$ and $R^2$ are independently selected from hydrogen, halogen and cyano, with the proviso that $R^2$ is absent when the optional double bond is present;
$R^3$ is selected from $C_1$-$C_6$ alkyl, $C_3$-$C_8$ cycloalkyl, $C_1$-$C_6$ heteroalkyl, $C_3$-$C_8$ heterocycle, $C_1$-$C_6$ hydroxyalkyl, $C_2$-$C_6$ alkynyl, $C_2$-$C_6$ heteroalkynyl, $C_2$-$C_6$ alkenyl, $C_2$-$C_6$ heteroalkenyl, $C_1$-$C_6$ haloalkyl and alkylamino;
$Y^1$ is $C_1$-$C_6$ alkyl, $C_3$-$C_8$ cycloalkyl, $C_1$-$C_6$ heteroalkyl, $C_3$-$C_8$ heterocycloalkyl, halo, $C_1$-$C_6$ haloalkyl, —$NR^9R^{10}$ or —$SR^{11}$;
$R^9$ and $R^{10}$ are independently selected from hydrogen, $C_1$-$C_6$ alkyl, $C_3$-$C_8$ cycloalkyl, aryl, heteroaryl, $C_3$-$C_8$ heterocycle, $C_2$-$C_6$ alkenyl and $C_1$-$C_6$ heteroalkyl, wherein $R^9$ and $R^{10}$, together with the atoms to which they are attached, are optionally taken together to form an aryl, heteroaryl, cycloalkyl or heterocyclic ring;
$R^{11}$ is selected from $C_1$-$C_6$ alkyl, $C_3$-$C_8$ cycloalkyl, $C_1$-$C_6$ heteroalkyl, $C_3$-$C_8$ heterocycloalkyl, $C_1$-$C_6$ hydroxyalkyl, $C_2$-$C_6$ alkynyl, $C_2$-$C_6$ heteroalkynyl, $C_2$-$C_6$ alkenyl, $C_2$-$C_6$ heteroalkenyl, $C_1$-$C_6$ haloalkyl and aminoalkyl;
$Y^2$ is hydrogen, $C_1$-$C_6$ alkyl, $C_3$-$C_8$ cycloalkyl, $C_1$-$C_6$ heteroalkyl, $C_3$-$C_8$ heterocycle, halo, $C_1$-$C_6$ haloalkyl, amino or alkylamino;
$Y^3$ is $C_3$-$C_{14}$ heterocycle or $C_3$-$C_{14}$ heteroaryl;
$Y^4$ is hydrogen, $C_1$-$C_6$ alkyl, $C_1$-$C_6$ heteroalkyl, halo or $C_1$-$C_6$ haloalkyl; and wherein each aryl, heteroaryl, cycloalkyl or heterocycle is independently unsubstituted or substituted with 1, 2, or 3 substituents independently selected from $C_1$-$C_4$ alkyl, hydroxy, $C_1$-$C_4$ alkoxy, halo, oxo, $C_1$-$C_4$ haloalkyl, and $C_1$-$C_4$ hydroxyalkyl.

Clause 2. The compound of clause 1, or a pharmaceutically salt thereof, wherein $R^1$ and $R^2$ are hydrogen, with the proviso that $R^2$ is absent when the optional double bond is present.

Clause 3. The compound of clause 1 or clause 2, or a pharmaceutically acceptable salt thereof, wherein $R^3$ is $C_1$-$C_6$ alkyl, $C_1$-$C_6$ heteroalkyl, $C_2$-$C_6$ alkynyl or $C_1$-$C_6$ hydroxyalkyl.

Clause 4. The compound of any one of clauses 1-3, or a pharmaceutically acceptable salt thereof, wherein $R^3$ is propyl.

Clause 5. The compound of any one of clauses 1-4, or a pharmaceutically acceptable salt thereof, wherein $Y^1$ is —$NR^9R^{10}$ wherein $R^9$ and $R^{10}$ are independently selected from hydrogen, $C_1$-$C_6$ alkyl, $C_3$-$C_8$ cycloalkyl, aryl, heteroaryl, $C_3$-$C_8$ heterocycle, $C_2$-$C_6$ alkenyl, $C_1$-$C_6$ heteroalkyl, or together with the atoms to which they are attached, are optionally taken together to form an aryl, heteroaryl, cycloalkyl or heterocyclic ring.

Clause 6. The compound of any one of clauses 1-5, or a pharmaceutically acceptable salt thereof, wherein $Y^1$ is selected from the group consisting of

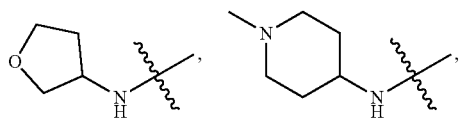

-continued

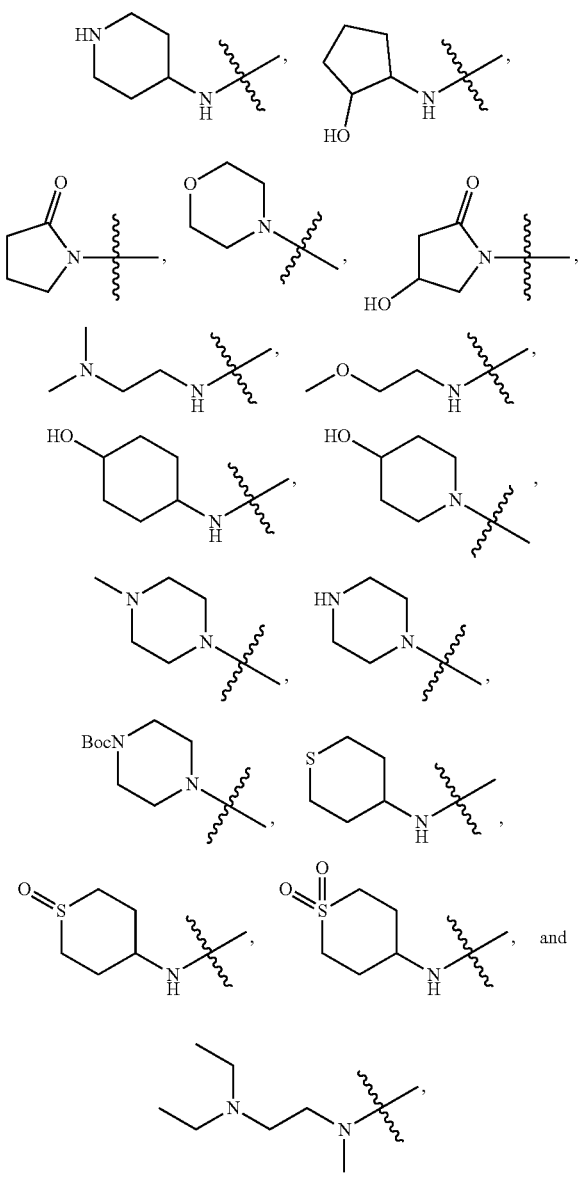

wherein

is the point of attachment to formula (I).

Clause 7. The compound of any one of clauses 1-6, or a pharmaceutically acceptable salt thereof, wherein $Y^1$ is

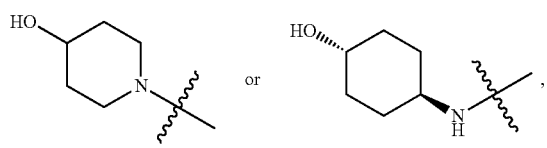 [SMILES: *N1CCC(O)CC1 ; *N[C@H]1CC[C@H](O)CC1]

wherein

is the point of attachment to formula (I).

Clause 8. The compound of any one of clauses 1-7, or a pharmaceutically acceptable salt thereof, wherein $Y^2$ is hydrogen.

Clause 9. The compound of any one of clauses 1-8, or a pharmaceutically acceptable salt thereof, wherein $Y^4$ is hydrogen.

Clause 10. The compound of any one of clauses 1-9, or a pharmaceutically acceptable salt thereof, wherein $Y^3$ is selected from the group consisting of carbazole, tetrahydrocarbazole, indole, indazole, tetrahydroindole, tetrahydroindazole, pyrrolopyridine and pyrazolopyridine, wherein each aryl, heteroaryl, cycloalkyl or heterocyclic ring is independently unsubstituted or substituted with 1, 2, or 3 substituents independently selected from $C_1$-$C_4$ alkyl, hydroxy, $C_1$-$C_4$ alkoxy, halo, oxo, hydroxylamine, $C_1$-$C_4$ haloalkyl, and $C_1$-$C_4$ hydroxyalkyl.

Clause 11. The compound of any one of clauses 1-10, or a pharmaceutically acceptable salt thereof, wherein $Y^3$ is

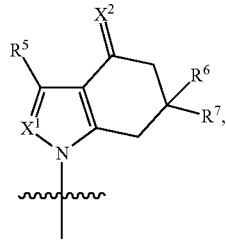

wherein
$X^1$ is N or $CR^4$;
$R^4$ is hydrogen, $C_1$-$C_6$ haloalkyl, $C_1$-$C_6$ alkyl, or $C_1$-$C_6$ heteroalkyl;
$R^5$ is hydrogen, $C_1$-$C_6$ alkyl, $C_1$-$C_6$ haloalkyl or $COOR^8$;
$R^8$ is $C_1$-$C_4$ alkyl;
wherein $R^4$ and $R^5$, together with the atoms to which they are attached, are optionally taken together to form an aryl, heteroaryl, cycloalkyl or heterocyclic ring, wherein each aryl, heteroaryl, cycloalkyl or heterocycle is independently unsubstituted or substituted with 1, 2, or 3 substituents independently selected from $C_1$-$C_4$ alkyl, hydroxy, $C_1$-$C_4$ alkoxy, halo, oxo, $C_1$-$C_4$ haloalkyl, and $C_1$-$C_4$ hydroxyalkyl;
$X^2$ is —O or —NOH;
$R^6$ and $R^7$ are independently selected from $C_1$-$C_4$ alkyl, $C_1$-$C_4$ haloalkyl and hydrogen; and
wherein

is the point of attachment to formula (I).

Clause 12. The compound of clause 11, or a pharmaceutically acceptable salt thereof, wherein $R^6$ and $R^7$ are independently selected from $C_1$-$C_4$ alkyl.

Clause 13. The compound of any one of clauses 11-12, or a pharmaceutically acceptable salt thereof, wherein $R^6$ and $R^7$ are methyl.

Clause 14. The compound of any one of clauses 11-13, or a pharmaceutically acceptable salt thereof, wherein $X^2$ is —O.

Clause 15. The compound of any one of clauses 11-14, or a pharmaceutically acceptable salt thereof, wherein $R^5$ is hydrogen or $C_1$-$C_6$ alkyl.

Clause The compound of any one of clauses 11-15, or a pharmaceutically acceptable salt thereof, wherein $R^5$ is hydrogen or methyl.

Clause 17. The compound of any one of clauses 11-16, or a pharmaceutically acceptable salt thereof, wherein $X^1$ is N.

Clause 18. The compound of any one of clauses 11-16, or a pharmaceutically acceptable salt thereof, wherein $X^1$ is $CR^4$.

Clause 19. The compound of any one of clauses 11-16 or clause 18, or a pharmaceutically acceptable salt thereof, wherein $R^4$ is hydrogen.

Clause 20. The compound of any one of clauses 1-19, or a pharmaceutically acceptable salt thereof, selected from the group consisting of:

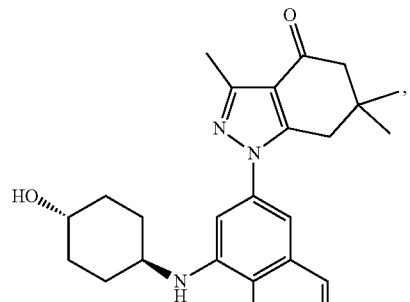

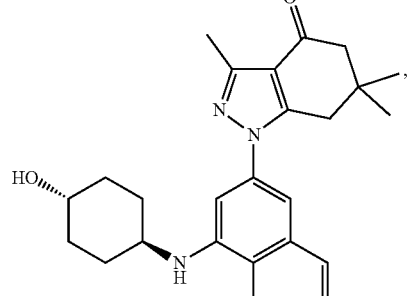

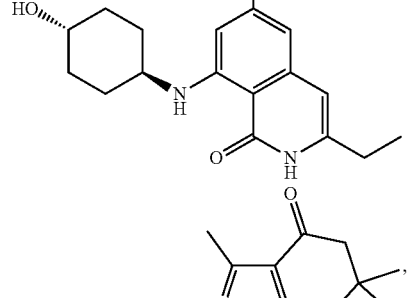

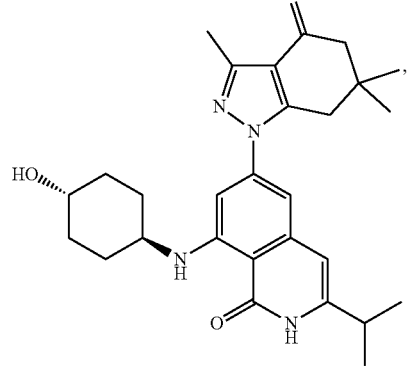

-continued

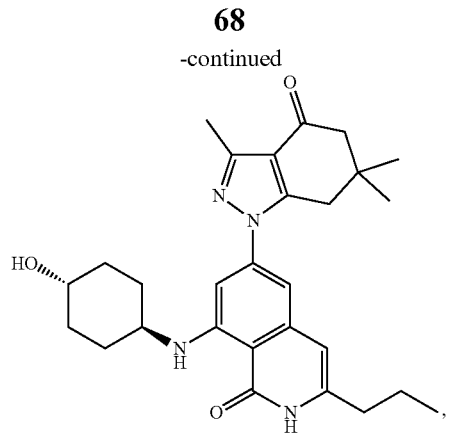

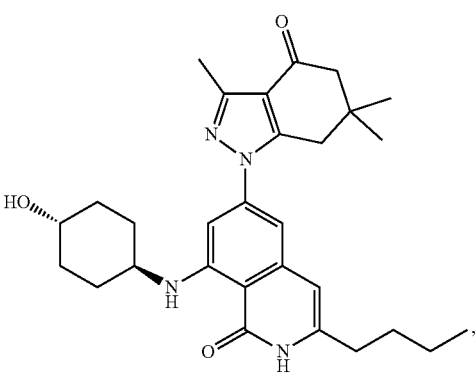

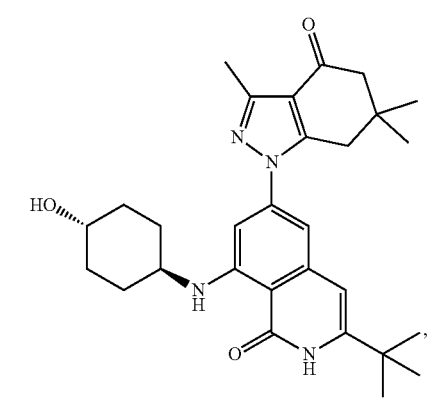

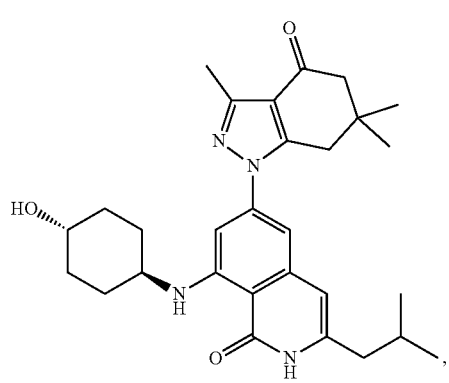

69
-continued
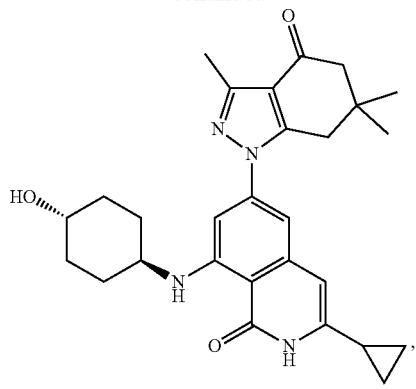
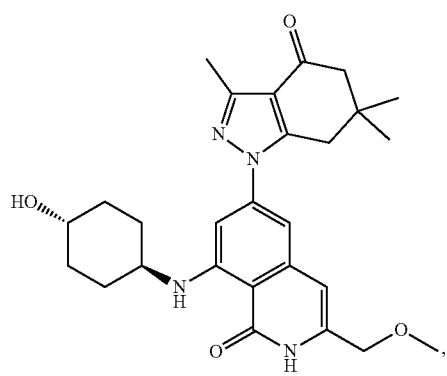
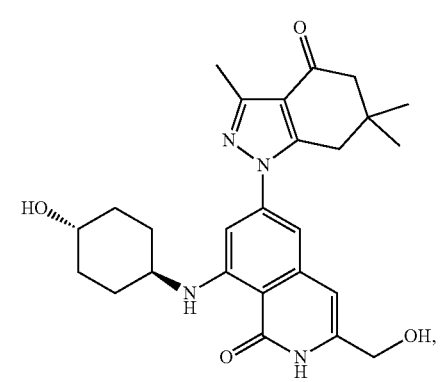
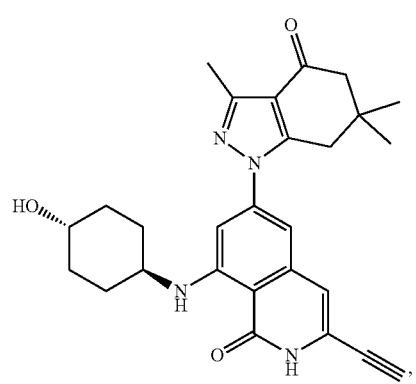
70
-continued
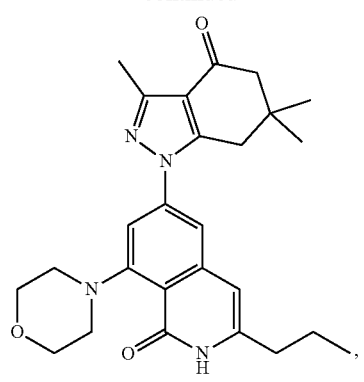
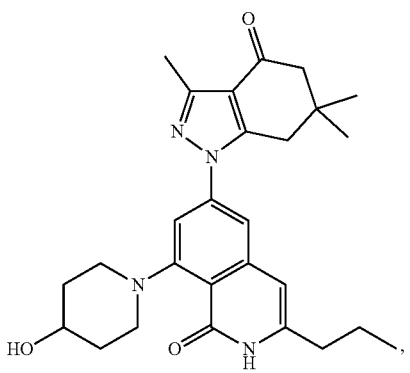
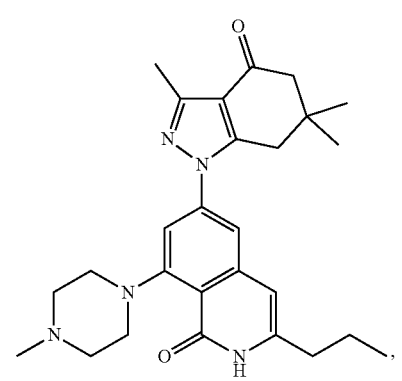
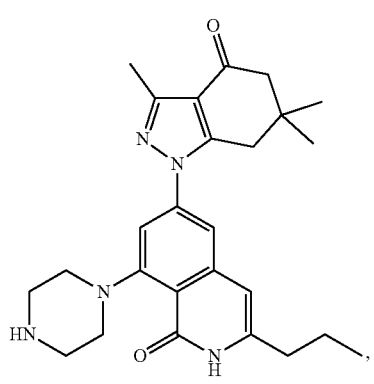

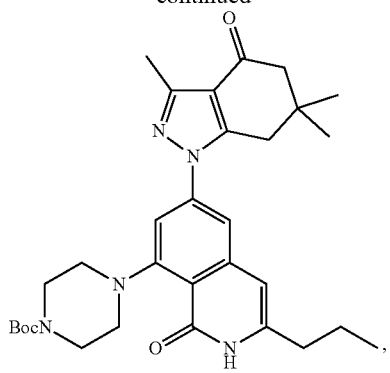

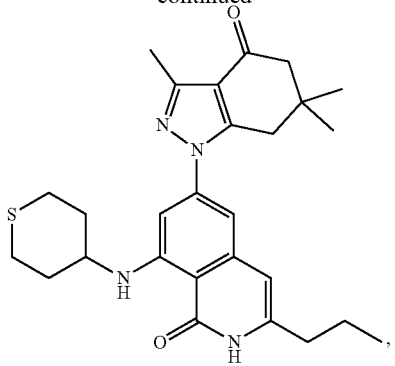

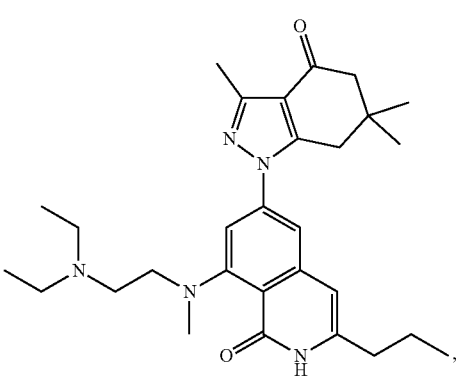

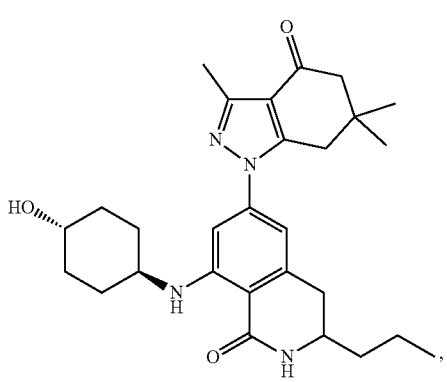

Clause 21. A pharmaceutical composition comprising the compound of any of clauses 1-20, or a pharmaceutically acceptable salt thereof, and a pharmaceutically acceptable carrier.

Clause 22. A method of inhibiting Hsp90 comprising contacting Hsp90 with an effective amount of the compound of any of clauses 1-20.

Clause 23. A method of clause 22, wherein the Hsp90 is Hsp90β.

Clause 24. A method of treating a disease or disorder in a subject in need thereof, comprising administering to a subject in need thereof a therapeutically effective amount of the compound of any of clauses 1-20, or a pharmaceutically acceptable salt thereof, or the pharmaceutical composition of clause 21.

Clause 25. The method of clause 24, wherein the disease or disorder is cancer, viral disease, anti-inflammatory disease, angiogenesis-related disease, chemotherapy-induced toxicity or a protein misfolding or aggregation disease.

Clause 26. The method of clause 25, wherein the disease or disorder is cancer.

Clause 27. The method of clauses 25 or 26, wherein the cancer is a carcinoma, sarcoma, lymphoma, leukemia, melanoma, mesothelioma, multiple myeloma, or seminoma.

Clause 28. The method of any one of clauses 25-27, wherein the cancer is leukemia.

Clause 29. The method of any one of clauses 25-27, wherein the cancer is a cancer of the bladder, blood, bone, brain, breast, cervix, colon/rectum, endometrium, head and neck, kidney, liver, lung, muscle tissue, ovary, pancreas, prostate, skin, spleen, stomach, testicle, thyroid or uterus.

Clause 30. The method of clause 29, wherein the cancer is of the colon, breast, bladder, prostate or kidney.

What is claimed is:

1. A compound of formula (I),

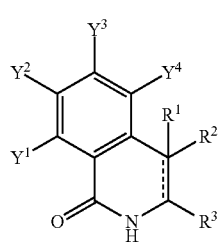

(I)

or a pharmaceutically acceptable salt thereof, wherein the dashed line (-----) represents an optional double bond;
$R^1$ and $R^2$ are independently selected from hydrogen, halogen and cyano, with the proviso that $R^2$ is absent when the optional double bond is present;
$R^3$ is selected from $C_1$-$C_6$ alkyl, $C_3$-$C_8$ cycloalkyl, $C_1$-$C_6$ heteroalkyl, $C_3$-$C_8$ heterocycle, $C_1$-$C_6$ hydroxyalkyl, $C_2$-$C_6$ alkynyl, $C_1$-$C_6$ heteroalkynyl, $C_1$-$C_6$ alkenyl, $C_1$-$C_6$ heteroalkenyl, $C_1$-$C_6$ haloalkyl and alkylamino;
$Y^1$ is $C_1$-$C_6$ alkyl, $C_3$-$C_8$ cycloalkyl, $C_1$-$C_6$ heteroalkyl, $C_3$-$C_8$ heterocycloalkyl, halo, $C_1$-$C_6$ haloalkyl, —$NR^9R^{10}$ or —$SR^{11}$;
$R^9$ and $R^{10}$ are independently selected from hydrogen, $C_1$-$C_6$ alkyl, $C_3$-$C_8$ cycloalkyl, aryl, heteroaryl, $C_3$-$C_8$ heterocycle, $C_1$-$C_6$ alkenyl and $C_1$-$C_6$ heteroalkyl, wherein $R^9$ and $R^{10}$, together with the atoms to which they are attached, are optionally taken together to form an aryl, heteroaryl, cycloalkyl or heterocyclic ring;
$R^{11}$ is selected from $C_1$-$C_6$ alkyl, $C_3$-$C_8$ cycloalkyl, $C_1$-$C_6$ heteroalkyl, $C_3$-$C_8$ heterocycloalkyl, $C_1$-$C_6$ hydroxyalkyl, $C_1$-$C_6$ alkynyl, $C_1$-$C_6$ heteroalkynyl, $C_1$-$C_6$ alkenyl, $C_1$-$C_6$ heteroalkenyl, $C_1$-$C_6$ haloalkyl and aminoalkyl;
$Y^2$ is hydrogen, $C_1$-$C_6$ alkyl, $C_3$-$C_8$ cycloalkyl, $C_1$-$C_6$ heteroalkyl, $C_3$-$C_8$ heterocycle, halo, $C_1$-$C_6$ haloalkyl, amino or alkylamino;
$Y^3$ is $C_3$-$C_{14}$ heterocycle or $C_3$-$C_{14}$ heteroaryl;
$Y^4$ is hydrogen, $C_1$-$C_6$ alkyl, $C_1$-$C_6$ heteroalkyl, halo or $C_1$-$C_6$ haloalkyl; and
wherein each aryl, heteroaryl, cycloalkyl or heterocycle is independently unsubstituted or substituted with 1, 2, or 3 substituents independently selected from $C_1$-$C_4$ alkyl, hydroxy, $C_1$-$C_4$ alkoxy, halo, oxo, $C_1$-$C_4$ haloalkyl, and $C_1$-$C_4$ hydroxyalkyl.

2. The compound of claim 1, or a pharmaceutically acceptable salt thereof, wherein $R^1$ and $R^2$ are hydrogen, with the proviso that $R^2$ is absent when the optional double bond is present.

3. The compound of claim 1, or a pharmaceutically acceptable salt thereof, wherein $R^3$ is $C_1$-$C_6$ alkyl, $C_1$-$C_6$ heteroalkyl, $C_2$-$C_6$ alkynyl or $C_1$-$C_6$ hydroxyalkyl.

4. The compound of claim 1, or a pharmaceutically acceptable salt thereof, wherein $R^3$ is propyl.

5. The compound of claim 1, or a pharmaceutically acceptable salt thereof, wherein $Y^1$ is —$NR^9R^{10}$ wherein $R^9$ and $R^{10}$ are independently selected from hydrogen, $C_1$-$C_6$ alkyl, $C_3$-$C_8$ cycloalkyl, aryl, heteroaryl, $C_3$-$C_8$ heterocycle, $C_2$-$C_6$ alkenyl, $C_1$-$C_6$ heteroalkyl, or together with the atoms to which they are attached, are optionally taken together to form an aryl, heteroaryl, cycloalkyl or heterocyclic ring.

6. The compound of claim 1, or a pharmaceutically acceptable salt thereof, wherein $Y^1$ is selected from the group consisting of

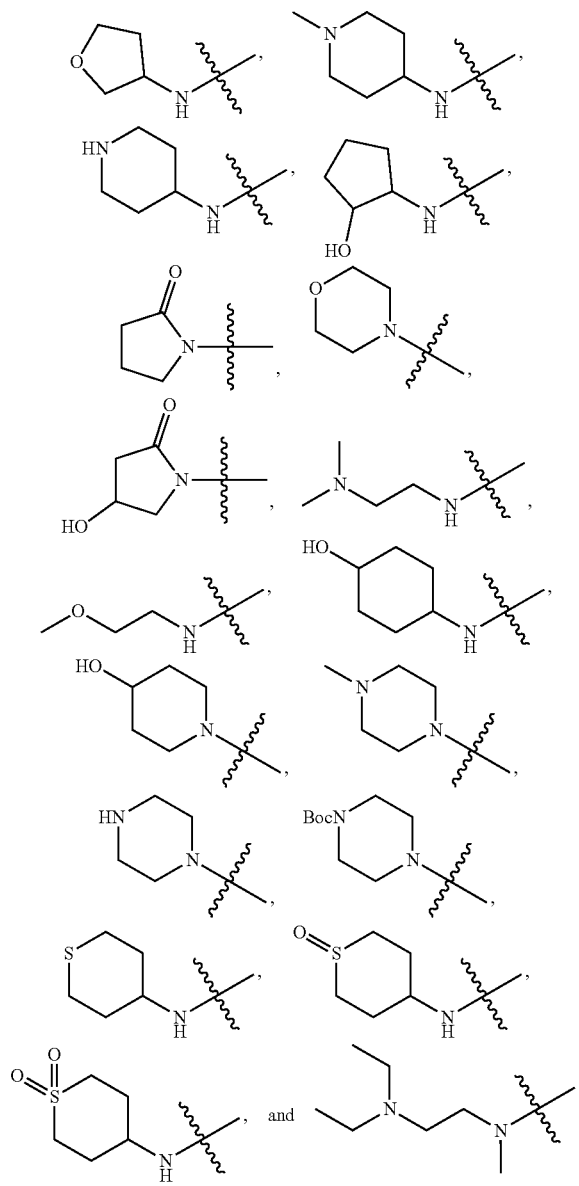

wherein

is the point of attachment to formula (I).

7. The compound of claim 1, or a pharmaceutically acceptable salt thereof, wherein $Y^1$ is

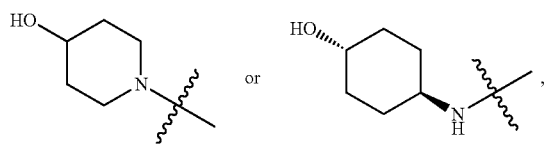 [SMILES: *N1CCC(O)CC1 ; *N[C@H]1CC[C@H](O)CC1]

wherein

is the point of attachment to formula (I).

8. The compound of claim 1, or a pharmaceutically acceptable salt thereof, wherein $Y^2$ is hydrogen.

9. The compound of claim 1, or a pharmaceutically acceptable salt thereof, wherein $Y^4$ is hydrogen.

10. The compound of claim 1, or a pharmaceutically acceptable salt thereof, wherein $Y^3$ is selected from the group consisting of carbazole, tetrahydrocarbazole, indole, indazole, tetrahydroindole, tetrahydroindazole, pyrrolopyridine and pyrazolopyridine, wherein each aryl, heteroaryl, cycloalkyl or heterocyclic ring is independently unsubstituted or substituted with 1, 2, or 3 substituents independently selected from $C_1$-$C_4$ alkyl, hydroxy, $C_1$-$C_4$ alkoxy, halo, oxo, hydroxylamine, $C_1$-$C_4$ haloalkyl, and $C_1$-$C_4$ hydroxyalkyl.

11. The compound of claim 1, or a pharmaceutically acceptable salt thereof, wherein $Y^3$ is

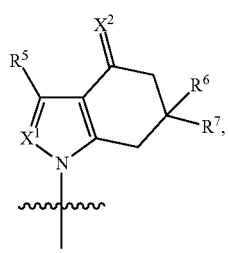

wherein

X is N or $CR^4$;

$R^4$ is hydrogen, $C_1$-$C_6$ haloalkyl, $C_1$-$C_6$ alkyl, or $C_1$-$C_6$ heteroalkyl;

$R^5$ is hydrogen, $C_1$-$C_6$ alkyl, $C_1$-$C_6$ haloalkyl or $COOR^8$;

$R^8$ is $C_1$-$C_4$ alkyl;

wherein $R^4$ and $R^5$, together with the atoms to which they are attached, are optionally taken together to form an aryl, heteroaryl, cycloalkyl or heterocyclic ring, wherein each aryl, heteroaryl, cycloalkyl or heterocycle is independently unsubstituted or substituted with 1, 2, or 3 substituents independently selected from $C_1$-$C_4$ alkyl, hydroxy, $C_1$-$C_4$ alkoxy, halo, oxo, $C_1$-$C_4$ haloalkyl, and $C_1$-$C_4$ hydroxyalkyl;

$X^2$ is —O or —NOH;

$R^6$ and $R^7$ are independently selected from $C_1$-$C_4$ alkyl, $C_1$-$C_4$ haloalkyl and hydrogen; and wherein

is the point of attachment to formula (I).

12. The compound of claim 11, or a pharmaceutically acceptable salt thereof, wherein $R^6$ and $R^7$ are independently selected from $C_1$-$C_4$ alkyl.

13. The compound of claim 11, or a pharmaceutically acceptable salt thereof, wherein $R^6$ and $R^7$ are methyl.

14. The compound of claim 11, or a pharmaceutically acceptable salt thereof, wherein $X^2$ is —O.

15. The compound of claim 11, or a pharmaceutically acceptable salt thereof, wherein $R^5$ is hydrogen or $C_1$-$C_6$ alkyl.

16. The compound of claim 11, or a pharmaceutically acceptable salt thereof, wherein $R^5$ is hydrogen or methyl.

17. The compound of claim 11, or a pharmaceutically acceptable salt thereof, wherein $X^1$ is N.

18. The compound of claim 11, or a pharmaceutically acceptable salt thereof, wherein $X^1$ is $CR^4$.

19. The compound of claim 18, or a pharmaceutically acceptable salt thereof, wherein $R^4$ is hydrogen.

20. The compound of claim 1, or a pharmaceutically acceptable salt thereof, selected from the group consisting of:

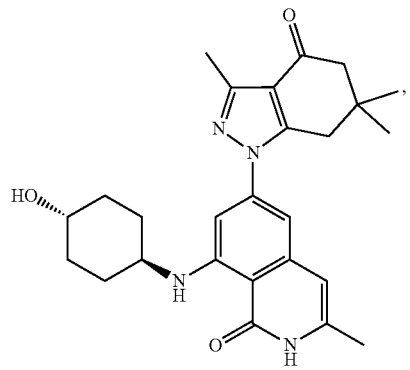

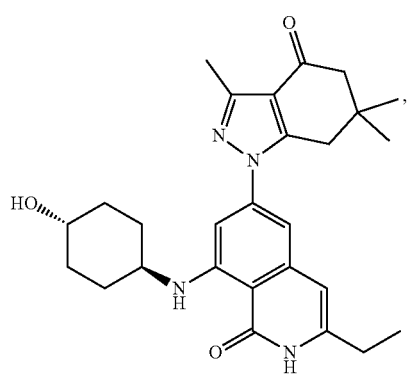

-continued
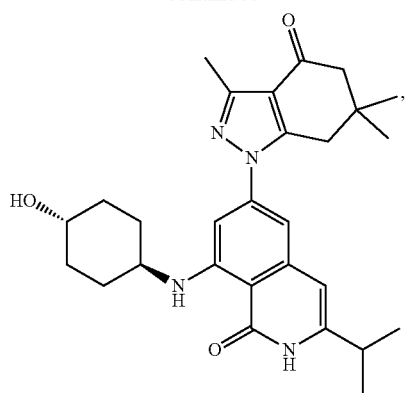
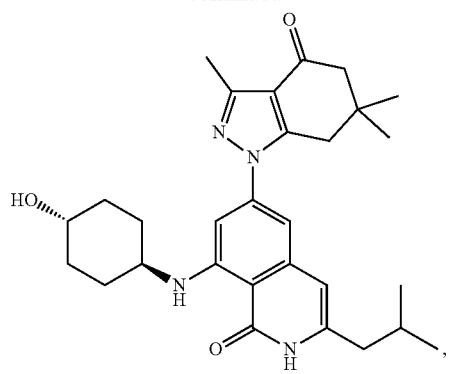
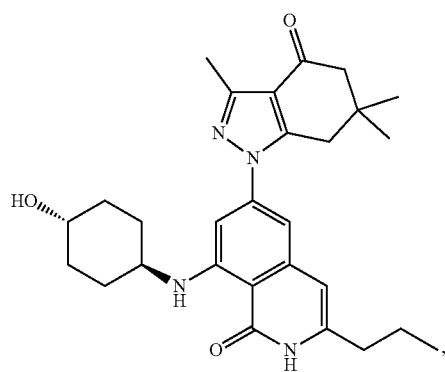
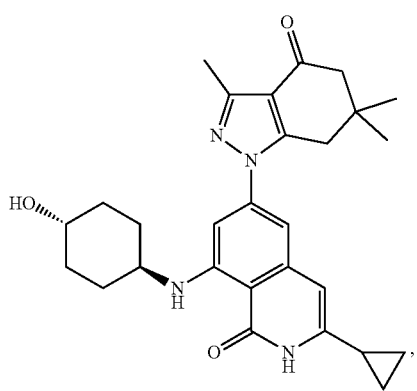
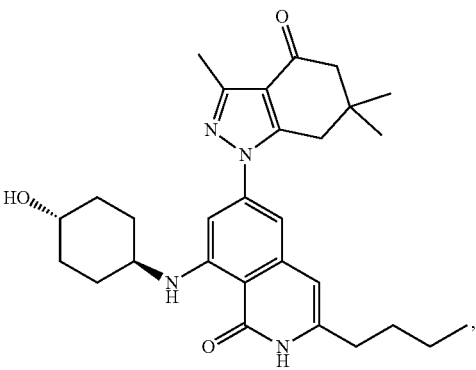
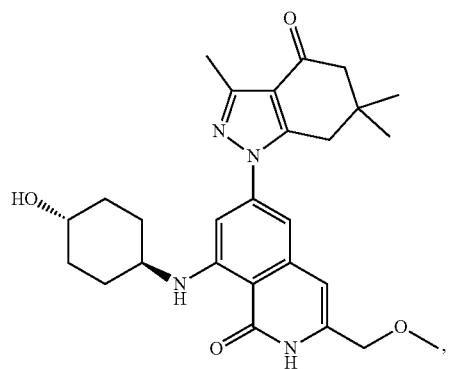
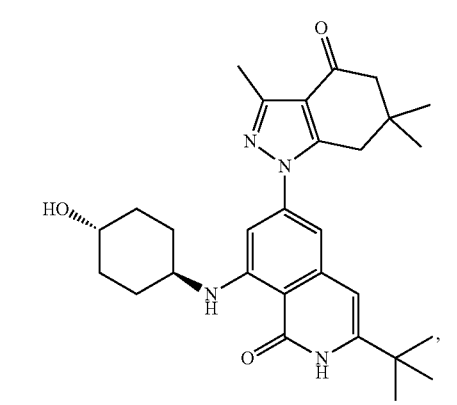
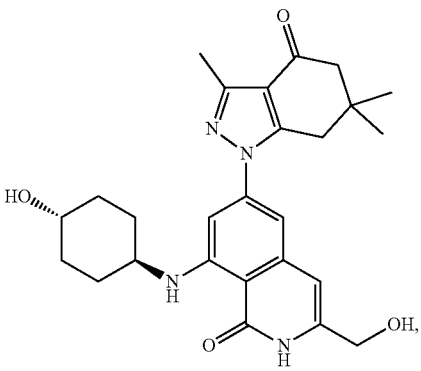

79
-continued
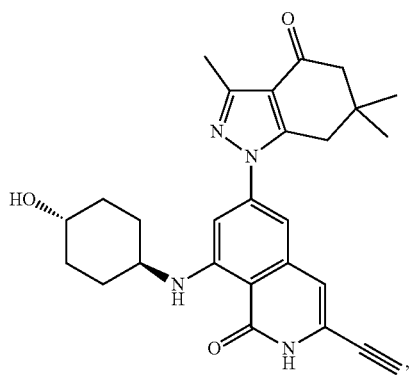
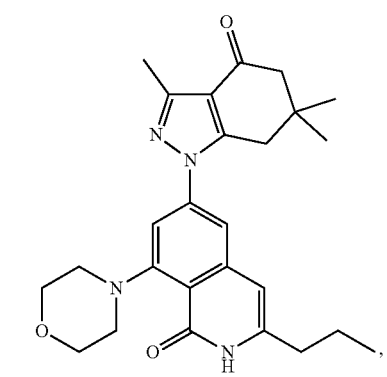
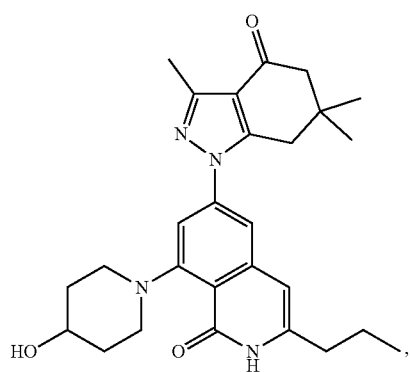
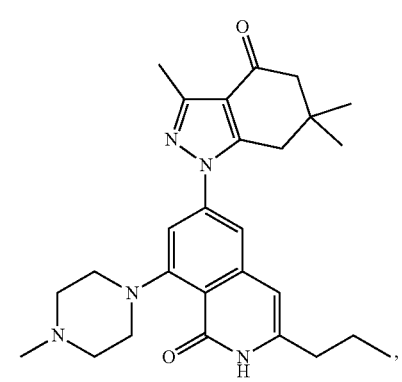
80
-continued
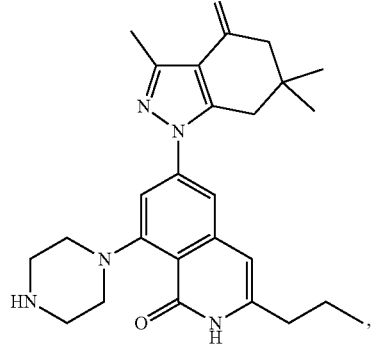
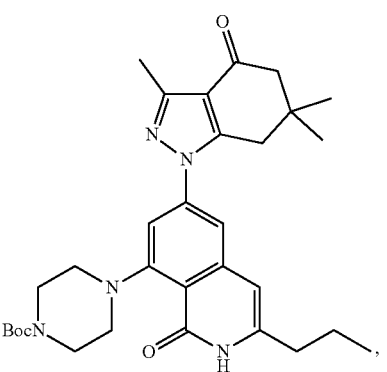
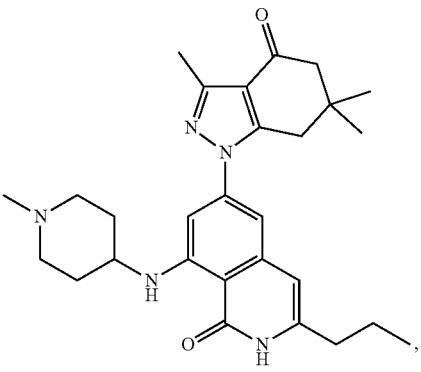
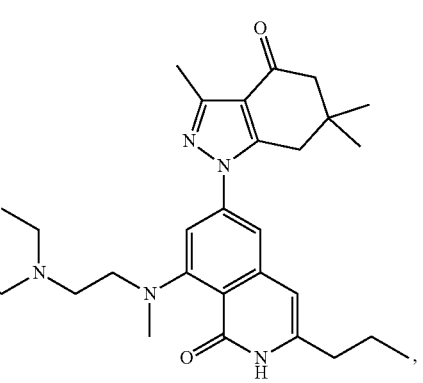

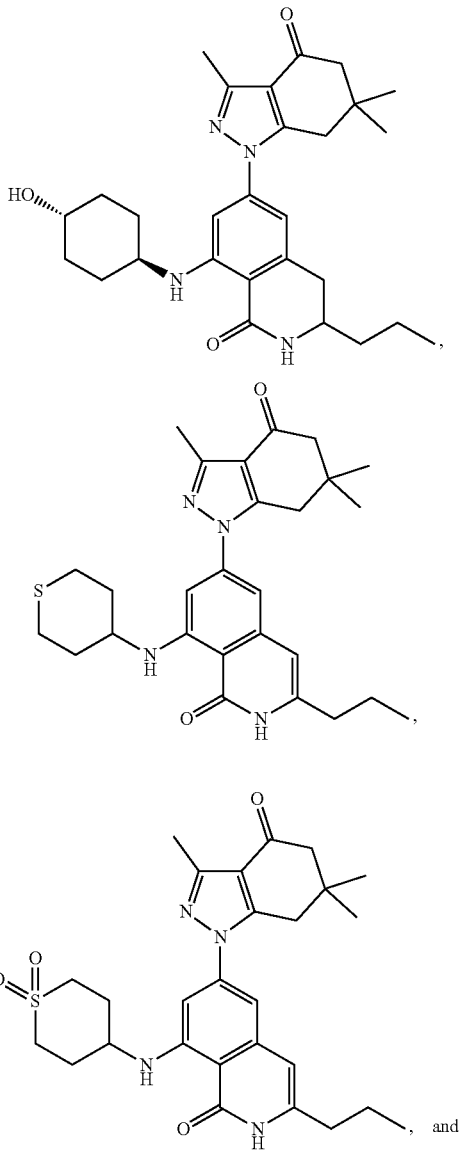

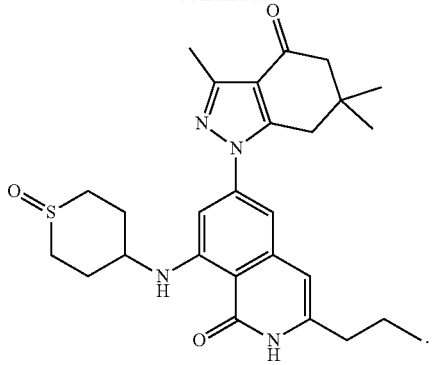

21. A pharmaceutical composition comprising the compound of any of claims 1-20, or a pharmaceutically acceptable salt thereof, and a pharmaceutically acceptable carrier.

22. A method of inhibiting Hsp90 comprising contacting Hsp90 with an effective amount of the compound of any of claims 1-20.

23. A method of claim 22, wherein the Hsp90 is Hsp90.

24. A method of treating a disease or disorder in a subject in need thereof, comprising administering to a subject in need thereof a therapeutically effective amount of the compound of any of claims 1-20, or a pharmaceutically acceptable salt thereof, or the pharmaceutical composition of claim 21, wherein the disease or disorder is cancer, viral disease, anti-inflammatory disease, angiogenesis-related disease, chemotherapy-induced toxicity or a protein misfolding or aggregation disease.

25. The method of claim 24, wherein the disease or disorder is cancer.

26. The method of claim 24, wherein the cancer is a carcinoma, sarcoma, lymphoma, leukemia, melanoma, mesothelioma, multiple myeloma, or seminoma.

27. The method of claim 24, wherein the cancer is leukemia.

28. The method of claim 24, wherein the cancer is a cancer of the bladder, blood, bone, brain, breast, cervix, colon/rectum, endometrium, head and neck, kidney, liver, lung, muscle tissue, ovary, pancreas, prostate, skin, spleen, stomach, testicle, thyroid or uterus.

29. The method of claim 28, wherein the cancer is of the colon, breast, bladder, prostate or kidney.

* * * * *